US008034787B2

(12) United States Patent
Dubois et al.

(10) Patent No.: US 8,034,787 B2
(45) Date of Patent: Oct. 11, 2011

(54) ENZYME-CLEAVABLE PRODRUG COMPOUNDS

(75) Inventors: Vincent Dubois, Fleurus (BE); Ann Marie Fernandez, Brussels (BE); Sanjeev Gangwar, Foster City, CA (US); Evan Lewis, Daly City, CA (US); Thomas J. Lobl, Foster City, CA (US); Matthew H. Nieder, Burlingame, CA (US); Lesley B. Pickford, Menlo Park, CA (US); Andre Trouet, Herentals (BE); Geoffrey T. Yarranton, Burlingame, CA (US)

(73) Assignee: Medarex, Inc., Princeton, NJ (US)

(*) Notice: Subject to any disclaimer, the term of this patent is extended or adjusted under 35 U.S.C. 154(b) by 548 days.

(21) Appl. No.: 12/228,636

(22) Filed: Aug. 14, 2008

(65) Prior Publication Data

US 2009/0110753 A1  Apr. 30, 2009

Related U.S. Application Data

(60) Division of application No. 09/879,442, filed on Jun. 11, 2001, now Pat. No. 7,425,541, and a continuation-in-part of application No. PCT/US99/30393, filed on Dec. 10, 1999.

(60) Provisional application No. 60/290,448, filed on May 11, 2001, provisional application No. 60/211,887, filed on Jun. 14, 2000, provisional application No. 60/119,312, filed on Feb. 8, 1999, provisional application No. 60/111,793, filed on Dec. 11, 1998.

(51) Int. Cl.
*A61K 38/06* (2006.01)
*A61P 35/00* (2006.01)
*C07K 16/28* (2006.01)

(52) U.S. Cl. .................. 514/21.9; 424/181.1; 514/19.3; 514/19.4; 530/389.7

(58) Field of Classification Search .................. None
See application file for complete search history.

(56) References Cited

U.S. PATENT DOCUMENTS

| | | | |
|---|---|---|---|
| 4,144,333 A | 3/1979 | Hall et al. | |
| 4,277,466 A | 7/1981 | Trouet et al. | |
| 4,296,105 A | 10/1981 | Baurain et al. | |
| 4,376,765 A | 3/1983 | Trouet et al. | |
| 4,388,305 A | 6/1983 | Trouet et al. | |
| 4,639,456 A | 1/1987 | Trouet et al. | |
| 4,671,958 A | 6/1987 | Rodwell et al. | |
| 4,703,107 A | 10/1987 | Monsigny et al. | |
| 4,719,312 A | 1/1988 | Firestone | |
| 4,870,162 A | 9/1989 | Trouet et al. | |
| 4,931,544 A | 6/1990 | Katre et al. | |
| 5,024,835 A | 6/1991 | Rao et al. | |
| 5,220,001 A | 6/1993 | Ok et al. | |
| 5,286,637 A | 2/1994 | Veronese et al. | |
| 5,574,017 A | 11/1996 | Gutheil | |
| 5,599,686 A | 2/1997 | DeFeo-Jones et al. | |
| 5,833,986 A | 11/1998 | LaRochelle et al. | |
| 5,948,750 A | 9/1999 | Garsky et al. | |
| 5,962,216 A | 10/1999 | Trouet et al. | |
| 6,048,720 A | 4/2000 | Dalborg et al. | |
| 6,265,540 B1 | 7/2001 | Isaacs et al. | |
| 6,372,712 B1 | 4/2002 | Briesewitz et al. | |
| 6,680,054 B1 | 1/2004 | Reece et al. | |
| 6,897,034 B2 | 5/2005 | Bebbington et al. | |
| 6,989,452 B2 | 1/2006 | Ng et al. | |
| 7,087,600 B2 | 8/2006 | Ng et al. | |
| 7,115,573 B2 | 10/2006 | Pickford et al. | |
| 7,129,261 B2 | 10/2006 | Ng et al. | |
| 7,214,663 B2 | 5/2007 | Bebbington et al. | |
| 7,425,541 B2 * | 9/2008 | Dubois et al. .................. | 514/1.1 |
| 2003/0119021 A1 | 6/2003 | Koster et al. | |
| 2004/0039160 A1 | 2/2004 | Pickford et al. | |

FOREIGN PATENT DOCUMENTS

| | | |
|---|---|---|
| BE | 869485 | 12/1978 |
| BE | 882541 | 7/1980 |
| CA | 2203622 A1 | 2/1996 |
| EP | 0037388 A2 | 10/1981 |
| EP | 0041935 A1 | 12/1981 |
| EP | 0044090 A2 | 1/1982 |
| EP | 0126685 A1 | 11/1984 |
| EP | 0208615 B1 | 1/1987 |
| EP | 0475230 A1 | 3/1992 |
| EP | 0126344 A2 | 11/1994 |
| EP | 0640622 A1 | 3/1995 |
| WO | 91/11457 A1 | 8/1991 |
| WO | 92/07068 A1 | 4/1992 |
| WO | 93/02703 A1 | 2/1993 |

(Continued)

OTHER PUBLICATIONS

Aboud-Pirak, Esther et al., "Cytotoxic Activity of Daunorubicin or Vindesin Conjugated to a Monoclonal Antibody on Cultured MCF-7 Breast Carcinoma Cells," Biochemical Pharmacology, vol. 38(4):641-648 (1989).

Balajthy, Zoltan et al., "Synthesis and Functional Evaluation of a Peptide Derivative of 1-Beta-D-Arabinofuranosylcytosine," J. Med. Chem., vol. 35:3344-3349 (1992).

Barrett, Alan J. et al., "Chicken Liver Pz-peptidase, a thiol-dependent metallo-endopeptidase," Biochem. J., vol. 271:701-706 (1990).

Barrett, Alan J. et al., "Thimet Oligopeptidase and Oligopeptidase M or Neurolysin," Methods in Enzymology, vol. 248:529-556 (1995).

Barrett, Alan J. et al., "Thimet oligopeptidase," Handbook of Proteolytic Enzymes, Academic Press, San Diego, pp. 1108-1111 (1998).

(Continued)

*Primary Examiner* — Cecilia J Tsang
*Assistant Examiner* — Satyanarayana Gudibande
(74) *Attorney, Agent, or Firm* — Nelson Mullins Riley & Scarborough LLP; Jane E. Remillard, Esq.; Pankaj N. Desai

(57) ABSTRACT

The prodrug of the invention is a modified form of a therapeutic agent and comprises a therapeutic agent, an oligopeptide, a stabilizing group and, optionally, a linker group. The prodrug is cleavable by the enzyme Thimet oligopeptidase, or TOP. Also disclosed are methods of designing prodrugs by utilizing TOP-cleavable sequences within the conjugate and methods of treating patients with prodrugs of the invention.

17 Claims, 23 Drawing Sheets

FOREIGN PATENT DOCUMENTS

| | | |
|---|---|---|
| WO | 96/00503 A1 | 1/1996 |
| WO | 96/05863 A1 | 2/1996 |
| WO | 96/33198 A1 | 10/1996 |
| WO | 98/21243 A1 | 5/1998 |
| WO | 98/52966 A1 | 11/1998 |
| WO | 00/33888 A2 | 6/2000 |

OTHER PUBLICATIONS

Baurain, Roger et al., "Amino Acid and Dipeptide Derivatives of Daunorubicin. 2. Cellular Pharmacology and Antitumor Activity on L1210 Leukemic Cells in Vitro and in Vivo," J. Med. Chem., vol. 23:1171-1174 (1980).

Baurain, R. et al., "Antitumor activity of daunorubicin linked to proteins: lysosomal hydrolysis and antitumor activity of conjugates prepared with peptidic spacer arms," Chemical Abstracts, vol. 97:386, No. 97:150636d (1982).

Baurain, R. et al., "Antitumor Activity of Daunorubicin Linked to Proteins: Lysosomal Hydrolysis and Antitumor Activity of Conjugates Prepared with Peptidic Sapcer Arms," Curr. Chemother. Immunother., Proc. Int. Congr. Chemther., 12th, vol. 2:1430-1432 (1982).

Baurain, et al., "Targeting of Daunorubicin by Covalent and Reversible Linkage to Carrier Proteins. Lysosomal Hydrolysis and Antitumoral Activity of Conjugates Prepared with Peptidic Spacers," Drugs Exp. Clin., vol. 9:303-311 (1983).

Beyer, Ulrich et al., "Synthesis and in Vitro Efficacy of Transferrin Conjugates of the Anticancer Drug Chlorambucil," J. Med., Chem., vol. 41:2701-2708 (1998).

Bricout, Nerve et al., "Synthetic and Kinetic Aspects of Nickel-Catalysed Amination of Allylic Alcohol Derivatives," Tetrahedron, vol. 54:1073-1084 (1998).

Buchler, Markus et al., "Proteinase yscD (oligopeptidase yscD) Structure, function and relationship of the yeast enzyme with mammalian thimet oligopeptidase (metalloendopeptidase, EP 24.15)," Eur. J. Biochem., vol. 219:627-639 (1994).

Camargo, Antonio C.M. et al., "Structural features that make oligopeptides susceptible substrates for hydrolysis by recombinant thimet oligopeptides," Biochem. J., vol. 321:517-522 (1997).

Camargo, A.C.M. et al., "Structural Requirements of Bioactive Peptides for Interaction with Endopeptidase 22.19," Neuropeptides, vol. 26:281-287 (1994).

Cardozo, Christopher et al., "Evidence That Enzymatic Conversion of N-[1(R,S)-Carboxy-3-Phenylpropyl]-Ala-Ala-Phe-p-Aminobenzoate, a Specific Inhibitor of Endopeptidase 24.15, to N-[1(R,S)-Carboxy-3-Phenylpropyl]-Ala-Ala is Necessary for Inhibition of Angiotensin Converting Enzyme," Peptides, vol. 14:1259-1262 (1993).

Casale, Lisa et al., "Quantitation of Endopeptidases 24.11 and Endopeptidase 24.15 in Human Blood Leukocytes," Enzyme Protein, vol. 48:143-148 (1995).

Chaires, Jonathan B. et al., "Self-Association of Daunomycin," Biochemistry, vol. 21:3927-3932 (1982).

Chakravarty, Prasun K. et al., "Plasmin-Activated Prodrugs for Cancer Chemotherapy. 1. Synthesis and Biological Activity of Peptidylacivicin and Peptidylphenylenediamine Mustard," J. Med. Chem., vol. 26:633-638 (1983).

Chakravarty, Prasun K. et al., "Plasmin-Activated Prodrugs for Cancer Chemotherapy. 2. Synthesis and Biological Activity of Peptidyl Derivatives of Doxorubicin," J. Med. Chem., vol. 26:638-644 (1983).

Chen, Chixu et al., "'Analogous' Organic Synthesis of Small-Compound Libraries: Validation of Combinatorial Chemistry in Small-Molecule Synthesis," J. Am. Chem. Soc., vol. 116:2661-2662 (1994).

Chen, Jinq-May et al., "Immunolocalization of Thimet Oligopeptidase in Chicken Enbryonic Fibroblasts," Experimental Cell Research, vol. 216:80-85 (1995).

Confalonieri, C. et al., "The use of a new laser particle sizer and shape analyser to detect and evaluate gelatinous microparticles suspended in reconstituted anthracycline infusion solutions," Journal of Pharmaceutical & Biomedical Analysis, vol. 9(1):1-8 (1991).

Crack, Peter J. et al., "The association of metalloendopeptidase EC 3.4.24.15 at the extracellular surface of the AtT-20 cell plasma membrane," Brain Research, vol. 835:113-124 (1999).

Dando, Pam M. et al., "Human thimet oligopeptidase," Biochem. J., vol. 294:451-457 (1993).

De Marre, Anne et al., "Evaluation of the hydrolytic and enzymatic stability of macromolecular Mitomycin C derivatives," Journal of Controlled Release, vol. 31:89-97 (1994).

DeJongh, D.C. et al., "The Use of N-Succinyl Derivatives in the Study of Amino Acids and Peptides by Mass Spectrometry," Biomed. Mass Spec., vol. 3:191-195 (1976).

Delucia, Alphonse et al., "Efficacy and toxicity of differently charged polycationic protamine-like peptides for heparin anticoagulation reversal," J. Vasc. Surg., vol. 18:49-60 (1993).

Dubois, Vincet et al., "Pharmacokinetics and Tissue Distribution of CPI-0004, a New Prodrug of Doxorubicin, in Normal and Tumor-Bearing Mice," American Association for Cancer Research, Scientific Proceedings, Abstract No. 3329 (2000).

Eisenbrand, G. et al., "An Approach Towards More Selective Anticancer Agents," Synthesis, vol. 10:1246-1258 (1996).

Ekrami, Hossein M. et al., "Carbamylation Decreases the Cytotoxicity but not the Drug-Carrier Properties of Polylysines," Journal of Drug Targeting, vol. 2:469-475 (1995).

Fernandez, Anne-Marie et al., "N-Succinyl-(Beta-alanyl-L-leucyl-L-alanyl-L-leucyl)doxorubicin: An Extracellularly Tumor-Actovated Prodrug Devoid of Intravenous Acute Toxicity," J. Med. Chem., vol. 44:3750-3753 (2001).

Ferro, Emer S. et al., "Secretion of a Neuropeptide-Metabolizing Enzyme Similar to Endopeptidase 22.19 by Glioma C6 Cells," Biochemical and Biophysical Research Communications, vol. 191(1):275-281 (1993).

Ferro, Emer S. et al., "Secretion of Metalloendopeptidase 24.15 (EC 3.4.24.15)," DNA and Cell Biology, vol. 18 (10):781-789 (1999).

Gaertner, Hubert F. et al., "Site-Specific Attachment of Functionalized Poly(ethylene glycol) to the Amino Terminus of Proteins," Bioconjugate Chem., vol. 7:38-44 (1996).

Garrido, Paula A.G. et al., "Confocal Microscopy Reveals Thimet Oligopeptidase (EC 3.4.24.15) and Neurolysin (EC 3.4.24.16) in the Classical Secretory Pathway," DNA and Cell Biology, vol. 18(4):323-331 (1999).

Genet, Jean Pierre et al., "A General and Simple Removal of the Allyloxycarbonyl Protecting Group by Palladium-Catalyzed Reactions Using Nitrogen and Sulfur Nucleophiles," Synlett, vol. 9:680-682 (1992).

Genet, Jean Pierre et al., "Practical Palladium-Mediated Deprotective Method of Allyloxycarbonyl in Aqueous Media," Tetrahedron, vol. 50(2):497-503 (1994).

Glucksman, Marc J. et al., "Strategies for Characterizing, Cloning, and Expressing Soluble Endopeptidases," Methods in Neurosciences, vol. 23:296-316 (1995).

Harnois-Pontoni, Marzia et al., "Hydrosoluble Fluorogenic Substrates for Plasmin," Analytical Biochemistry, vol. 193(2):248-255 (1991).

Hayashi, Mirian A.F. et al., "Species Specificity of Thimet Oligopeptidase (EC 3.4.24.15)," Biol. Chem. Hoppe-Seyler, vol. 377:283-291 (1996).

Hoes, C.J.T. et al., "The Application of Drug-Polymer Conjugates in Chemotherapy," Horizons in Biochemistry and Biophysics, Drug Carrier Systems, vol. 9, F.H.D. Roerdink and A.M. Kroon (Eds.), John Wiley & Sons, New York, pp. 57-109 (1989).

Holcenberg, John S. et al., "Biologic and Physical Properties of Succinylated and Glycosylated *Acinetobacter* Glutaminase-Asparaginase," The Journal of Biological Chemistry, vol. 250(11):4165-4170 (1975).

Inada, Yuji et al., "Modification of Proteins with Polyethylene Glycol Derivatives," Methods in Enzymology, vol. 242:65-90 (1994).

Israel, Mervyn et al., "Adriamycin Analogues. Preparation and Biological Evaluation of Some N-(Trifluoroacetyl)-14-O-[(N-acetylamino)acyl]adriamycin Derivatives," J. Med. Chem., vol. 29:1273-1276 (1986).

Jacchieri, S.G. et al., "A comparative conformational analysis of thimet oligopeptidase (EC 3.4.24.15) substrates," J. Peptide Res., vol. 51:452-459 (1998).

Jiracek, Jiri et al., "Development of Highly Potent and Selective Phosphinic Peptide Inhibitors of Zinc Endopeptidase 24-15 Using Combinatorial Chemistry," The Journal of Biological Chemistry, vol. 270(37):21701-21706 (1995).

Kaneko, Takushi et al., "New Hydrazone Derivatives of Adriamycin and Their Immunoconjugates—a Correlation between Acid Stability and Cytotoxicity," Bioconjugate Chemistry, vol. 2(3):133-141 (1991).

Kania, Robert S. et al., "Free C-Terminal Resin-Bound Peptides: Reversal of Peptide Orientation via a Cyclization/Cleavage Protocol," J. Am. Chem. Soc., vol. 116:8835-8836 (1994).

Kato, Akira et al., "Cloning, amino acid sequence and tissue distribution of porcine thimet oligopeptidase. A comparison with soluble angiotensin-binding protein," Eur. J. Biochem., vol. 221:159-165 (1994).

Kennett, C.N. et al., "Comparative histochemical, biochemical and immunocytochemical studies of cathepsin B in human gingiva," Journal of Periodontal Research, vol. 29:203-213 (1994).

King, H. Dalton et al., "Synthesis and proteolytic cleavage of 3'-N-peptidyl-Adriamycin prodrugs," Struct. Biol., pp. 137-139 (1988).

Knight, C. Graham, "A quenched fluorescent substrate for thimet peptidase containing a new fluorescent amino acid, DL-2-amino-3-(7-methoxy-4-coumary_propionic acid," Biochem. J., vol. 274:45-48 (1991).

Knight, C. Graham et al., "Structure/function relationships in the inhibition of thimet oligopeptidase by carboxyphenylpropyl-peptides," FEBS, vol. 294(3):183-186 (1991).

Knight, C. Graham et al., "Thimet oligopeptidase specificity: evidence of preferential cleavage near the C-terminus and product inhibition from kinetic analysis of peptide hydrolysis," Biochem. J., vol. 308:145-150 (1995).

Kratz, Felix et al., "Albumin Conjugates of the Anticancer Drug Chlorambucil: Synthesis: Characterization, and In Vitro Efficacy," Arch. Pharm. Pharm. Med. Chem., vol. 331:47-53 (1998).

Krause, Darren R. et al., "Characterization and Localization of Mitochondrial Oligopeptidase (MOP) (EC 3.4.24.16) Activity in the Human Cervical Adenocarcinoma Cell Line HeLa," Journal of Cellular Biochemistry, vol. 66:297-308 (1997).

Lesser, Marvin et al., "Hydrolysis of N-Formylmethionyl Chemotactic Peptides by Endopeptidase 24.11 and Endopeptidase 24.15," Peptides, vol. 17(1):13-16 (1996).

Lew, Rebecca A. et al., "Evidence for a Two-step Mechanism of Gonadotropin-releasing Hormone Metabolism by Prolyl Endopeptidase and Metalloendopeptidase EC 3.4.24.15 in Ovine Hypothalamic Extracts," The Journal of Biological Chemistry, vol. 269(17):12626-12632 (1994).

Lew, Rebecca A. et al., "Substrate Specificity Differences Between Recombinant Rat Testes Endopeptidase EC 3.4.24.15 and the Native Brain Enzyme," Biochemical and Biophysical Research Communications, vol. 209 (3):788-795 (1995).

Li, Choh Hao et al., "Adrenocorticotropins (ACTH). XX. Succinyl-Adrenocorticotropin and its Hydrolysis by Trypsin," The Journal of Biological Chemistry, vol. 235(9):2638-2641 (1960).

Masquelier, Michele et al., "Amino Acid and Derivatives of Daunorubicin. 1. Synthesis, Physicochemical Properties, and Lysosomal Digestion," J. Med. Chem., vol. 23:1166-1170 (1980).

Masquelier, Michele et al., "Antitumor activity of daunorubicin linked to proteins: biological and antitumor properties of peptidic derivatives of daunorubicin used as intermediates," Chemical Abstract Accession No. 97:150635 (1982).

Masquelier, M. et al., "Antitumor activity of daunorubicin linked to proteins: biological and antitumor properties of peptidic derivatives of daunorubicin used as intermediates," Curr. Chemother., 12th Annual Proceedings in Congr. Chemother., vol. 2:1428-1430 (1982).

Masquelier, M. et al., "Incorporation and Binding of Anthracycline Derivatives to Low Density Lipoprotein: in vitro and in vivo Studies of Drug-LDL Conjugates," Recent Adv. Chemother., 14th Annual Proc. Int. Congr. Chemother., Anticancer Section 1, pp. 311-312 (1985).

Matzanke, Berthold F. et al., "Evidence for polynuclear aggregates for ferric daunomycin. A Mossbauer, EPR, X-ray absorption spectroscopy and magnetic susceptibility study," Eur. J. Biochem., vol. 207:747-755 (1992).

Mayer, Roger et al., "Peptide Derivatives Specific for a *Plasmodium falciparum* Proteinase Inhibit the Human Erythrocyte Invasion by Merozoites," J. Med. Chem., vol. 34:3029-3035 (1991).

McKie, Norman et al., "Rat thimet oligopeptidase: large-scale expression in *Escherichia coli* and characterization of the recombinant enzyme," Biochem. J., vol. 309:203-207 (1995).

Menozzi, Milena et al., "Self-Association of Doxorubicin and Related Compounds in Aqueous Solution," Journal of Pharmaceutical Sciences, vol. 73(6):766-770 (1984).

Moody, Terry W. et al., "Neurotensin is Metabolized by Endogenous Proteases in Prostate Cancer Cell Lines," Peptides, vol. 19(2):253-258 (1998).

Morales, Teresa I. et al., "PZ-Peptidase from Chick Embryos," The Journal of Biological Chemistry, vol. 252 (14):4855-4860 (1977).

Noble, Florence et al., "Association of aminopeptidase N and endopeptidase 24.15 inhibitors potentiate behavioral effects mediated by nociceptin/orphanin FQ in mice," FEBS Letters, vol. 401:227-229 (1997).

Oliveira, Vitor et al., "Characterization of Thiol-, Aspartyl-, and Thiol-metallo-peptidase Activities in Madin-Darby Canine Kidney Cells," Journal of Cellular Biochemistry, vol. 76:478-488 (2000).

Orlowski, Marian et al., "Endopeptidase 24.15 from rat restes," Biochem. J., vol. 261:951-958 (1989).

Orlowski, Marian et al., "Substrate-Related Potent Inhibitors of Brain Metalloendopeptidase," Biochemistry, vol. 27:597-602 (1988).

Pan, Chin et al., "CD10 is a Key Enzyme Involved in the Activation of Tumor-activated Peptide Prodrug CPI-0004Na and Novel Analogues: Implications for the Design of Novel Peptide Prodrugs for the Therapy of CD10+ Tumors," Cancer Research, vol. 63:5526-5531 (2003).

Pierotti, Adrian R. et al., "Endopeptidase-24.15 in rat hypothalamic/pituitary/gonadal axis," Molecular and Cellular Endocrinology, vol. 76:95-103 (1991).

Pineau, Charles et al., "Distribution of thimet oligopeptidase (E.C. 3.4.24.15) in human and rat testes," Journal of Cell Science, vol. 112:3455-3462 (1999).

Pozsgay, Marianne et al., "A Method for Designing Peptide Substrates for Proteases. Tripeptidyl-p-nitroanilide Substrates for Subtilisin Carlsberg," Eur. J. Biochem., vol. 95:115-119 (1979).

Pozsgay, Marianne et al., "Substrate and Inhibitor Studies of Thermolysin-like Neutral Metalloendopeptidase from Kidney Membrane Fractions. Comparison with Bacterial Thermolysin," Biochemistry, vol. 25:1292-1299 (1986).

Rao, Kandukuri S.P. Bhushana et al., "Vinblastin-23-oyl Amino Acid Derivatives: Chemistry, Physicochemical Data, Toxicity, and Antitumor Activities against P388 and L1210 Leukemias," J. Med. Chem., vol. 28:1079-1088 (1985).

Rink, Hans, "Solid-Phase Synthesis of Protected Peptide Fragments Using a Trialkoxy-Diphenyl-Methylester Resin," Tetrahedron Letters, vol. 28(33):3787-3790 (1987).

Rioli, Vanessa et al., "Neuropeptide Specificity and Inhibition of Recombinant Isoforms of the Endopeptidase 3.4.24.16 Family: Comparison with the Related Recombinant Endopeptidase 3.4.24.15," Biochemical and Biophysical Research Communications, vol. 250:5-11 (1998).

Said, Samireh et al., "Systemic Treatment: Methotrexate," Clinics in Dermatology, vol. 15:781-797 (1997).

Schmittberger, T. et al., "Synthesis of the Palmitoylated and Prenylated C-terminal Lipopeptides of the Human R- and N-Ras Proteins," Bioorganic and Medicinal Chemistry, vol. 7:749-762 (1999).

Seitz, David E. et al., "Synthesis and Chemical Properties of a Series of Doxorubicin Enaminomalonyl-beta-Alanine Derivatives," Tetrahedron Letters, vol. 36(9):1413-1416 (1995).

Serizawa, Atsushi et al., "Characterization of a Mitochondrial Metallopeptidase Reveals Neurolysin as a Homologue of Thimet Oligopeptidase," The Journal of Biological Chemistry, vol. 270(5):2092-2098 (1995).

Shapiro, Gideon et al., "Mild and Rapid Azide-Mediated, Palladium Catalyzed Cleavage of Allylester Based Protecting Groups," Tetrahedron Letters, vol. 35(30):5421-5424 (1994).

Shrimpton, Code N. et al., "Thiol Activation of Endopeptidase EC 3.4.24.15," The Journal of Biological Chemistry, vol. 272(28):17395-17399 (1997).

Tabrizi-Fard, Mohammad et al., "Evaluation of the Pharmacokinetic Properties of a Doxorubicin Prodrug in Female ICR (CD-1) Mice Following Intravenous Bolus Administration," Proceedings of the American Association for Cancer Research, vol. 42:324, Abstract No. 1746 (2001).

Taylor, Peptide-based Drug Design, Controlling Transport and Metabolism, pp. 423-445 and 449-467 (1995).

Thompson, Annick et al., "Cloning and Functional Expression of a Metalloendopeptidase from Human Brain with the Ability to Cleave a Beta-APP Substrate Peptide," Biochemical and Biophysical Research Communication, vol. 213 (1):66-73 (1995).

Tisljar, Ursula, "Thimet Oligopeptidase—a Review of a Thiol Dependent Metallo-Endopeptidase also Known as Pz-Peptidase Endopeptidase 24.15 and Endo-Oligopeptidase," Biol. Chem. Hoppe-Seyler, vol. 374:91-100 (1993).

Tisljar, Ursula et al., "Thiol-dependent metallo-endopeptidase characteristics of Pz-peptidase in rat and rabbit," Biochem. J., vol. 267:531-533 (1990).

Trail, P.A. et al., "Cure of Xenografted Human Carcinomas by BR96-Doxorubicin Immunoconjugates," Science, vol. 261:212-215 (1993).

Trouet, Andre et al., "A covalent linkage between daunorubicin and proteins that is stable in serum and reversible by lysosomal hydrolases, as required for a lysosomotropic drug-carrier conjugate: in vitro adn in vivo studies," Proc. Natl. Acad. Sci. USA, vol. 79:626-629 (1982).

Trouet, Andre et al., "CPI-0004: An Extracellularly Tumor-Activated Prodrug of Doxorubicin," American Association for Cancer Research, Scientific Proceedings, Abstract No. 3328 (2000).

Tugwell, Peter et al., "Methotrexate in Rheumatoid Arthritis. Indications, Contraindications, Efficacy, adn Safety," Annals of Internal Medicine, vol. 107:358-366 (1987).

Ukai, Yuko et al., "A Novel Synthetic Inhibitor of Endopeptidase-24.15," J. Enzyme Inhibition, vol. 11:39-49 (1996).

Umemoto, Naoji et al., "Preparation and in vitro cytotoxicity of a methotrexate-anti-MM46 monoclonal antibody conjugate via an oligopeptide spacer," Int. J. Cancer, vol. 43:677-684 (1989).

Van Der Vijgh, Wim J.F. et al., "Comparative metabolism and pharmacokinetics of doxorubicin and 4'-epidoxorubicin in plasma, heart and tumor of tumor-bearing mice," Cancer Chemother. Pharmacol., vol. 26:9-12 (1990).

Wakefield, Thomas W. et al., "Heparin-mediated reductions of the toxic effects of protamine sulfate on rabbit myocardium," J. Vasc. Surg., vol. 16:47-53 (1992).

Waldmann, Herbert et al., "Enzymatic Protecting Group Techniques," Chemical Reviews, vol. 94(4):911-937 (1994).

Wang, Su-Sun, "p-Alkoxybenzyl Alcohol Resin and p-Alkoxybenzyloxycarbonylhydrazide Resin for Solid Phase Synthesis of Protected Peptide Fragment," Journal of American Chemical Society, vol. 95(4):1328-1333 (1973).

Whalley, E.T., "Receptors mediating the increase in vascular permeability to kinins: comparative studies in rat, guinea-pig and rabbit," Naunyn-Schmiedeberg's Arch. Pharmacol., vol. 336:99-104 (1987).

Wolfson, Adele J. et al., "Differential Activation of Endopeptidase EC 3.4.24.15 toward Natural and Synthetic Substrates by Metal Ions," Biochemical and Biophysical Research Communications, vol. 229:341-348 (1996).

Zhang, Chengzhi et al., "A Combinatorial Method for the Solid Phase Synthesis of alpha-Amino Phosphonates and Phosphonic Acids," Tetrahedron Letters, vol. 37(31):5457-5460 (1996).

International Search Report for Application No. PCT/US01/18903, dated Jun. 21, 2002.

Canadian Patent Office for Application No. 2,411,660, dated Jul. 15, 2009.

* cited by examiner

| Symbol | Name | Structure |
|---|---|---|
| Aca | 6-Aminocaproic Acid | $H_2N\text{-}(CH_2)_5\text{-}COOH$ |
| Aib | Aminoisobutyric Acid | $H_2N\text{-}C(CH_3)_2\text{-}COOH$ |
| Amb | 4-(Aminomethyl)benzoic Acid | $H_2N\text{-}CH_2\text{-}C_6H_4\text{-}COOH$ |
| APP | 3-Amino-3-phenylpropionic Acid | Ph-CH(NH₂)-CH₂-COOH |
| Dg | Diglycolic Acid | $HOOC\text{-}CH_2\text{-}O\text{-}CH_2\text{-}COOH$ |

FIG. 1A

| Symbol | Name | Structure |
|---|---|---|
| Gl | Glutaric Acid | 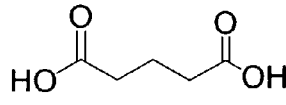 |
| Mal | Maleic Acid | 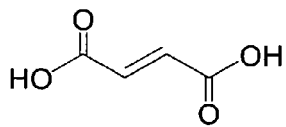 |
| NAA | 3-Amino-4,4-diphenylbutyric Acid | 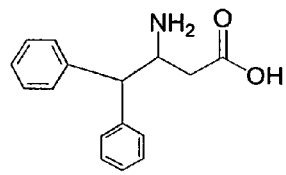 |
| Nal | 2-Naphthylalanine | 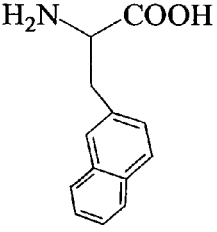 |
| Naph | 1,8-Naphthalene dicarboxylic Acid | 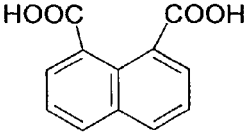 |
FIG. 1B

| Symbol | Name | Structure |
|---|---|---|
| Phg | Phenylglycine | 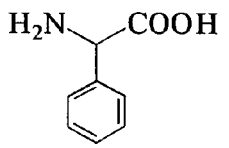 |
| PEG | Polyethylene Glycol$_{5000}$ Hemisuccinyl Ester | 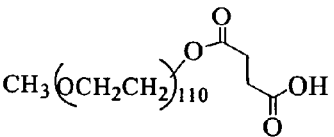 |
| Pyg | Pyroglutamic Acid | 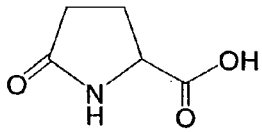 |
| Pyr | 3-Pyridylalanine | 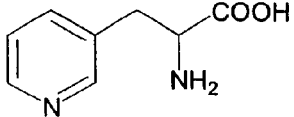 |
| Suc | Succinic Acid | 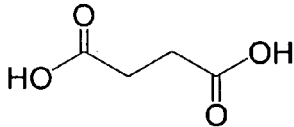 |
FIG. 1C

| Symbol | Name | Structure |
|---|---|---|
| Thi | 2-Thienylalanine | H₂N-CH(COOH)-CH₂-(2-thienyl) |
| Thz | 3-Thioproline or Thiazolidine-4-carboxylic Acid | thiazolidine-4-COOH |
| Tic | Tetrahydroisoquinoline-3-carboxylic Acid | tetrahydroisoquinoline-3-COOH |

FIG. 1D

| No: | (AA⁷) P5 | (AA⁶) P4 | (AA⁵) P3 | (AA⁴) P2 | (AA³) P1 | (AA²) P1' | (AA¹) P2' | SEQ ID NO: |
|---|---|---|---|---|---|---|---|---|
| 1 | D-Ala | Thi | βAla | βAla | Leu | Ala | Leu | SEQ ID NO: 1 |
| 2 | ∅ | Thi | βAla | βAla | Leu | Ala | Leu | SEQ ID NO: 2 |
| 3 | ∅ | ∅ | βAla | βAla | Leu | Ala | Leu | SEQ ID NO: 3 |
| 4 | ∅ | ∅ | ∅ | βAla | Ala | Ala | Ile | SEQ ID NO: 4 |
| 5 | ∅ | ∅ | ∅ | βAla | Ala | Ala | Leu | SEQ ID NO: 5 |
| 6 | ∅ | ∅ | ∅ | βAla | Phe | Tyr | Leu | SEQ ID NO: 6 |
| 7 | ∅ | ∅ | ∅ | βAla | Phe | Thr | Phe | SEQ ID NO: 7 |
| 8 | ∅ | ∅ | ∅ | βAla | Phe | Gly | Ile | SEQ ID NO: 8 |
| 9 | ∅ | ∅ | ∅ | βAla | Phe | Gly | Leu | SEQ ID NO: 9 |
| 10 | ∅ | ∅ | ∅ | βAla | Phe | Phe | Phe | SEQ ID NO: 10 |
| 11 | ∅ | ∅ | ∅ | βAla | Phe | Phe | Ile | SEQ ID NO: 11 |
| 12 | ∅ | ∅ | ∅ | βAla | Phe | Phe | Leu | SEQ ID NO: 12 |
| 13 | ∅ | ∅ | ∅ | βAla | Phe | Ala | Ile | SEQ ID NO: 13 |
| 14 | ∅ | ∅ | ∅ | βAla | Phe | Ala | Leu | SEQ ID NO: 14 |
| 15 | ∅ | ∅ | ∅ | Thi | Gly | Ala | Leu | SEQ ID NO: 15 |
| 16 | ∅ | ∅ | ∅ | Nal | Gly | Ala | Leu | SEQ ID NO: 16 |
| 17 | ∅ | ∅ | ∅ | βAla | Leu | Tyr | Leu | SEQ ID NO: 17 |
| 18 | ∅ | ∅ | ∅ | βAla | Leu | Thi | Leu | SEQ ID NO: 18 |
| 19 | ∅ | ∅ | ∅ | βAla | Leu | Thr | Phe | SEQ ID NO: 19 |
| 20 | ∅ | ∅ | ∅ | βAla | Leu | Thr | Ile | SEQ ID NO: 20 |
| 21 | ∅ | ∅ | ∅ | βAla | Leu | Thr | Leu | SEQ ID NO: 21 |
| 22 | ∅ | ∅ | ∅ | βAla | Leu | Ser | Leu | SEQ ID NO: 22 |
| 23 | ∅ | ∅ | ∅ | βAla | Leu | Pyr | Leu | SEQ ID NO: 23 |
| 24 | ∅ | ∅ | ∅ | βAla | Leu | Leu | Leu | SEQ ID NO: 24 |
| 25 | ∅ | ∅ | ∅ | βAla | Leu | Gly | Phe | SEQ ID NO: 25 |
| 26 | ∅ | ∅ | ∅ | βAla | Leu | Gly | Ile | SEQ ID NO: 26 |
| 27 | ∅ | ∅ | ∅ | Thi | Leu | Gly | Leu | SEQ ID NO: 27 |
| 28 | ∅ | ∅ | ∅ | βAla | Leu | Gly | Leu | SEQ ID NO: 28 |
| 29 | ∅ | ∅ | ∅ | Aib | Leu | Gly | Leu | SEQ ID NO: 29 |
| 30 | ∅ | ∅ | ∅ | βAla | Leu | Phe | Ile | SEQ ID NO: 30 |
| 31 | ∅ | ∅ | ∅ | βAla | Leu | Phe | Leu | SEQ ID NO: 31 |
| 32 | ∅ | ∅ | ∅ | βAla | Leu | Aib | Leu | SEQ ID NO: 32 |
| 33 | ∅ | ∅ | ∅ | βAla | Leu | Ala | Ala | SEQ ID NO: 33 |
| 34 | ∅ | ∅ | ∅ | βAla | Leu | Ala | βAla | SEQ ID NO: 34 |
| 35 | ∅ | ∅ | ∅ | βAla | Leu | Ala | Phe | SEQ ID NO: 35 |
| 36 | ∅ | ∅ | ∅ | βAla | Leu | Ala | Gly | SEQ ID NO: 36 |
| 37 | ∅ | ∅ | ∅ | βAla | Leu | Ala | Ile | SEQ ID NO: 37 |
| 38 | ∅ | ∅ | ∅ | βAla | Leu | Ala | Leu | SEQ ID NO: 38 |
| 39 | ∅ | ∅ | ∅ | Tic | Leu | Ala | Leu | SEQ ID NO: 39 |
| 40 | ∅ | ∅ | ∅ | Thz | Leu | Ala | Leu | SEQ ID NO: 40 |

∅ = not present

FIG. 10A

| No: | (AA⁷) P5 | (AA⁶) P4 | (AA⁵) P3 | (AA⁴) P2 | (AA³) P1 | (AA²) P1' | (AA¹) P2' | SEQ ID NO: |
|---|---|---|---|---|---|---|---|---|
| 41 | ∅ | ∅ | ∅ | Thi | Leu | Ala | Leu | SEQ ID NO: 41 |
| 42 | ∅ | ∅ | ∅ | Nal | Leu | Ala | Leu | SEQ ID NO: 42 |
| 43 | ∅ | ∅ | ∅ | NAA | Leu | Ala | Leu | SEQ ID NO: 43 |
| 44 | ∅ | ∅ | ∅ | D-Leu | Leu | Ala | Leu | SEQ ID NO: 44 |
| 45 | ∅ | ∅ | ∅ | D-Ala | Leu | Ala | Leu | SEQ ID NO: 45 |
| 46 | ∅ | ∅ | ∅ | D-Met | Leu | Ala | Leu | SEQ ID NO: 46 |
| 47 | ∅ | ∅ | ∅ | APP | Leu | Ala | Leu | SEQ ID NO: 47 |
| 48 | ∅ | ∅ | ∅ | Amb | Leu | Ala | Leu | SEQ ID NO: 48 |
| 49 | ∅ | ∅ | ∅ | βAla | Leu | Ala | Nal | SEQ ID NO: 49 |
| 50 | ∅ | ∅ | ∅ | βAla | Leu | Ala | Ser | SEQ ID NO: 50 |
| 51 | ∅ | ∅ | ∅ | βAla | Leu | Ala | Tyr | SEQ ID NO: 51 |
| 52 | ∅ | ∅ | ∅ | βAla | Met | Tyr | Phe | SEQ ID NO: 52 |
| 53 | ∅ | ∅ | ∅ | βAla | Met | Tyr | Leu | SEQ ID NO: 53 |
| 54 | ∅ | ∅ | ∅ | βAla | Met | Gly | Ile | SEQ ID NO: 54 |
| 55 | ∅ | ∅ | ∅ | Thi | Met | Gly | Leu | SEQ ID NO: 55 |
| 56 | ∅ | ∅ | ∅ | βAla | Met | Phe | Phe | SEQ ID NO: 56 |
| 57 | ∅ | ∅ | ∅ | βAla | Met | Phe | Ile | SEQ ID NO: 57 |
| 58 | ∅ | ∅ | ∅ | Tic | Met | Ala | Leu | SEQ ID NO: 58 |
| 59 | ∅ | ∅ | ∅ | Nal | Met | Ala | Leu | SEQ ID NO: 59 |
| 60 | ∅ | ∅ | ∅ | NAA | Met | Ala | Leu | SEQ ID NO: 60 |
| 61 | ∅ | ∅ | ∅ | βAla | Met | Ala | Leu | SEQ ID NO: 61 |
| 62 | ∅ | ∅ | ∅ | APP | Met | Ala | Leu | SEQ ID NO: 62 |
| 63 | ∅ | ∅ | ∅ | βAla | Nle | Tyr | Ile | SEQ ID NO: 63 |
| 64 | ∅ | ∅ | ∅ | βAla | Nle | Tyr | Leu | SEQ ID NO: 64 |
| 65 | ∅ | ∅ | ∅ | βAla | Nle | Thr | Ile | SEQ ID NO: 65 |
| 66 | ∅ | ∅ | ∅ | βAla | Nle | Thr | Leu | SEQ ID NO: 66 |
| 67 | ∅ | ∅ | ∅ | βAla | Nle | Gly | Phe | SEQ ID NO: 67 |
| 68 | ∅ | ∅ | ∅ | βAla | Nle | Gly | Ile | SEQ ID NO: 68 |
| 69 | ∅ | ∅ | ∅ | βAla | Nle | Gly | Leu | SEQ ID NO: 69 |
| 70 | ∅ | ∅ | ∅ | βAla | Nle | Phe | Ile | SEQ ID NO: 70 |
| 71 | ∅ | ∅ | ∅ | βAla | Nle | Ala | Ile | SEQ ID NO: 71 |
| 72 | ∅ | ∅ | ∅ | βAla | Nle | Ala | Leu | SEQ ID NO: 72 |
| 73 | ∅ | ∅ | ∅ | βAla | Nle | Ala | Phe | SEQ ID NO: 73 |
| 74 | ∅ | ∅ | ∅ | βAla | Nva | Ala | Leu | SEQ ID NO: 74 |
| 75 | ∅ | ∅ | ∅ | βAla | Phe | Tyr | Ile | SEQ ID NO: 75 |
| 76 | ∅ | ∅ | ∅ | Thi | Pro | Gly | Leu | SEQ ID NO: 76 |
| 77 | ∅ | ∅ | ∅ | Thi | Pro | Ala | Leu | SEQ ID NO: 77 |
| 78 | ∅ | ∅ | ∅ | Nal | Pro | Ala | Leu | SEQ ID NO: 78 |
| 79 | ∅ | ∅ | ∅ | βAla | Pro | Ala | Leu | SEQ ID NO: 79 |
| 80 | ∅ | ∅ | ∅ | βAla | Phe(Cl) | Ala | Leu | SEQ ID NO: 80 |

∅ = not present

FIG. 10B

| No: | (AA⁷) P5 | (AA⁶) P4 | (AA⁵) P3 | (AA⁴) P2 | (AA³) P1 | (AA²) P1' | (AA¹) P2' | SEQ ID NO: |
|---|---|---|---|---|---|---|---|---|
| 81 | ∅ | ∅ | ∅ | βAla | Phe(NO₂) | Ala | Ile | SEQ ID NO: 81 |
| 82 | ∅ | ∅ | ∅ | βAla | Phe(NO₂) | Ala | Leu | SEQ ID NO: 82 |
| 83 | ∅ | ∅ | ∅ | βAla | Phg | Ala | Leu | SEQ ID NO: 83 |
| 84 | ∅ | ∅ | ∅ | βAla | Pyr | Ala | Leu | SEQ ID NO: 84 |
| 85 | ∅ | ∅ | ∅ | Tic | Thr | Gly | Leu | SEQ ID NO: 85 |
| 86 | ∅ | ∅ | ∅ | βAla | Thi | Gly | Ile | SEQ ID NO: 86 |
| 87 | ∅ | ∅ | ∅ | βAla | Thi | Ala | Leu | SEQ ID NO: 87 |
| 88 | ∅ | ∅ | ∅ | βAla | Tic | Ala | Ile | SEQ ID NO: 88 |
| 89 | ∅ | ∅ | ∅ | βAla | Tic | Ala | Leu | SEQ ID NO: 89 |
| 90 | ∅ | ∅ | ∅ | βAla | Val | Ala | Leu | SEQ ID NO: 90 |
| 91 | ∅ | ∅ | ∅ | βAla | Trp | Ala | Leu | SEQ ID NO: 91 |
| 92 | ∅ | ∅ | ∅ | βAla | Tyr | Tyr | Phe | SEQ ID NO: 92 |
| 93 | ∅ | ∅ | ∅ | βAla | Tyr | Tyr | Ile | SEQ ID NO: 93 |
| 94 | ∅ | ∅ | ∅ | βAla | Tyr | Tyr | Leu | SEQ ID NO: 94 |
| 95 | ∅ | ∅ | ∅ | βAla | Tyr | Thr | Leu | SEQ ID NO: 95 |
| 96 | ∅ | ∅ | ∅ | βAla | Tyr | Phe | Leu | SEQ ID NO: 96 |
| 97 | ∅ | ∅ | ∅ | βAla | Tyr | Gly | Ile | SEQ ID NO: 97 |
| 98 | ∅ | ∅ | ∅ | Thi | Tyr | Gly | Leu | SEQ ID NO: 98 |
| 99 | ∅ | ∅ | ∅ | βAla | Tyr | Gly | Leu | SEQ ID NO: 99 |
| 100 | ∅ | ∅ | ∅ | βAla | Tyr | Phe | Ile | SEQ ID NO: 100 |
| 101 | ∅ | ∅ | ∅ | βAla | Tyr | Ala | Ile | SEQ ID NO: 101 |
| 102 | ∅ | ∅ | ∅ | Thi | Tyr | Ala | Leu | SEQ ID NO: 102 |
| 103 | ∅ | ∅ | ∅ | βAla | Tyr | Ala | Leu | SEQ ID NO: 103 |

∅ = not present

FIG. 10C

ENZYME-CLEAVABLE PRODRUG COMPOUNDS

RELATED APPLICATIONS

This application is a divisional application of U.S. Ser. No. 09/879,442, filed on Jun. 11, 2001, Issuing; which is a continuation-in-part of PCT/US99/30393 filed on Dec. 10, 1999, which claims priority under 35 U.S.C. §120; PCT/US99/30393 claims priority, under 35 U.S.C. §119(e), to U.S. Provisional Patent Application Ser. No. 60/119,312, filed on Feb. 8, 1999 and U.S. Provisional Patent Application Ser. No. 60/111,793, filed on Dec. 11, 1998. This application also claims priority, under 35 U.S.C. §119(e) to U.S. Provisional Patent Application Ser. No. 60/290,448 filed on May 11, 2001 and U.S. Provisional Patent Application Ser. No. 60/211,887, filed on Jun. 14, 2000. The contents of all of the aforementioned applications are hereby incorporated by reference in their entirety.

INTRODUCTION

Technical Field

The present invention is directed to new compounds useful as prodrugs. Such prodrugs may be used for treatment of disease, especially tumors, in patients.

BACKGROUND

Many therapeutic agents, such as anthracyclines and vinca alkaloids, are especially effective for the treatment of cancers. However, these molecules are often characterized in vivo by an acute toxicity, especially a bone marrow and mucosal toxicity, as well as a chronic cardiac toxicity in the case of the anthracyclines and chronic neurological toxicity in the case of the vinca alkaloids. Similarly, methotrexate may be used for the treatment of inflammatory reactions, such as rheumatic diseases, but its high toxicity limits its applications. Development of more specific and safer antitumor agents is desirable for greater effectiveness against tumor cells and a decrease in the number and severity of the side effects of these products (toxicity, destruction of non-tumor cells, etc.). Development of more specific anti-inflammatory agents is also desirable.

In order to minimize toxicity problems, therapeutic agents are advantageously presented to patients in the form of prodrugs. Prodrugs are molecules capable of being converted to drugs (active therapeutic compounds) in vivo by certain chemical or enzymatic modifications of their structure. For purposes of reducing toxicity, this conversion should be confined to the site of action or target tissue rather than the circulatory system or non-target tissue. Prodrugs are often characterized by a low stability in blood and serum, however, since blood and serum contain enzymes which degrade, or activate, the prodrugs before the prodrugs reach the desired sites within the patient's body.

A desirable class of prodrugs that overcomes such problems have been disclosed in Patent Cooperation Treaty International Publication No. WO 96/05863 and in U.S. Pat. No. 5,962,216, both incorporated herein by reference. Further useful prodrug compounds and methods of making such prodrugs are desirable, however, as are methods of making the prodrugs.

A particular object of the invention is Prodrugs that display a high specificity of action, a reduced toxicity, and an improved stability in blood relative to prodrugs of similar structure (especially the closest structure) that have existed in the public domain are particularly desirable.

SUMMARY OF THE INVENTION

The compound of the invention is a prodrug form of a therapeutic agent, in which the therapeutic agent is linked directly or indirectly to an oligopeptide, which in turn, is linked to a stabilizing group. The compound is cleavable by an enzyme associated with a target cell.

More generally, the present invention may be described as new prodrug compounds of a therapeutic agent, especially prodrugs comprising an antitumor therapeutic agent, displaying improved therapeutic properties relative to the products of the prior art, especially improved therapeutic properties in the treatment of cancerous tumors and/or in the treatment of inflammatory reactions such as rheumatic diseases. Improved therapeutic properties include decreased toxicity and increased efficacy. Particularly desired are prodrugs which display a high specificity of action, a reduced toxicity, an improved stability in the serum and blood, and which do not move into target cells until activated by a target cell associated enzyme. Prodrug compounds of a marker enabling tumors to be characterized (diagnosis, progression of the tumor, assay of the factors secreted by tumor cells, etc.) are also contemplated. Thus, the invention includes a diagnosis or assay kit employing a compound of the invention.

The present invention also relates to the pharmaceutical composition comprising the compound according to the invention and optionally a pharmaceutically acceptable carrier, adjuvant, vehicle, or the like.

Further, a method of decreasing toxicity and improving safety index by modifying a therapeutic agent to create a prodrug is disclosed. Other aspects of the invention include a method of designing a prodrug for administration to a patient and a method for treating a patient by administering a therapeutic dose of the compound.

Several processes for creating a prodrug of the invention are also described.

BRIEF DESCRIPTION OF THE DRAWINGS

FIGS. 1A-1D are a table of abbreviations, names, and structures.

FIGS. 10A-10C are a table of oligopeptides useful in the prodrug of the invention.

DETAILED DESCRIPTION

Abbreviations

Figure 2:
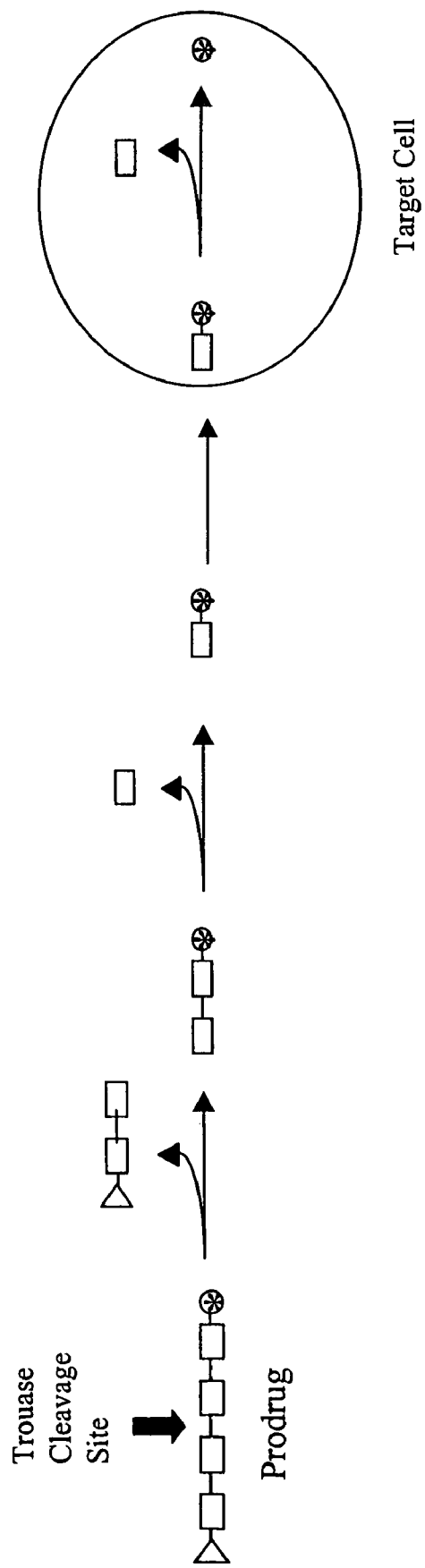
FIG. 2 is an exemplary scheme of cleavage of a prodrug of the invention in the extracellular vicinity of the target cell and within the target cell.

ACN=Acetonitrile
Aib=Aminoisobutyric acid
All=Allyl
Aloc=Allyloxycarbonyl
Amb=4-(Aminomethyl)benzoic acid
APP=3-Amino-3-phenylpropionic acid
DCC=N,N'-Dicyclohexylcarbodiimide
Boc=t-butyloxycarbonyl
Cap=amino caproic acid
Cou=amidomethylcoumarin
DBN=1,5 Diazabicyclo [4.3.0] non-5-ene
DBO=1,4 Diazabicyclo [2.2.2] octane
DBU=1,8-Diazabicyclo [5.4.0] undec-7-ene
DCM=Dichloromethane
DIC=N,N'-Diisopropylcarbodiimide
DIEA=Diisopropylethylamine
Dg=Diglycolic Acid
DMF=Dimethylformamide
Dnr=Daunorubicin
Dox=Doxorubicin
Dox-HCL=Hydrochloride salt of Doxorubicin
Et2O=diethyl ether
Fmoc=9-Fluorenylmethyloxycarbonyl
Gl=Glutaric Acid
OSU=N-Hydroxy Succinimide
HATU=O-(7-Azabenzotriazol-1-yl)-1,1,3,3-tetramethyluronium hexafluorophosphate
HBTU=2-(1H-Benzotriazole-1-yl)1,1,3,3-tetramethyluronium hexafluorophosphate
HEPES=Hydroxyethylpiperidine
HOBt=N-Hydroxybenzotriazole
HPLC=High pressure liquid chromatography
MeOH=Methanol
MeOSuc=Methyl hemisuccinate/Methyl hemisuccinyl
MDR=Multidrug resistance
MTD=Maximum Tolerated Dose
NAA=3-Amino-4,4-diphenylbutyric Acid
Nal=2-Naphthylalanine
Naph=1,8-Naphthalene dicarboxylic acid
Nle=Norleucine
NMP=N-methylpyrrolidine
Nva=Norvaline
PAM resin=4-hydroxymethylphenylacetamidomethyl
Phg=Phenylglycine
Pyg=Pyroglutamic acid
Pyr=3-Pyridylalanine
rRTOP=recombinant Rat TOP
RT, rt=Room temperature
SD-MTD=Single dose-Maximum Tolerated Dose
SD=Single dose
RD-MTD=Repeat dose-Maximum Tolerated Dose
RD=Repeat dose
Suc=Succinic Acid/succinyl
TCE=trichloroethyl
TFA=Trifluoroacetic acid
THF=Tetrahydrofuran
Thi=2-Thienylalanine
Thz=Thiazolidine-4-carboxylic acid
Tic=Tetrahydroisoquinoline-3-carboxylic acid
TOP=Thimet oligopeptidase The invention includes compounds that may be described as prodrug forms of therapeutic agents. Each of these therapeutic agents is modified by linking directly or indirectly to an oligopeptide, which in turn, is linked to a stabilizing group. The prodrug, and especially the oligopeptide portion of the prodrug, are cleavable by an enzyme associated with a target cell. The enzyme is preferably a trouase and more preferably is Thimet oligopeptidase.

Prodrug

The prodrug of the invention is a modified form of a therapeutic agent and comprises several portions, including:
(1) a therapeutic agent,
(2) an oligopeptide, and
(3) a stabilizing group, and
(4) optionally, a linker group.

Each of the portions of the prodrug are discussed in greater detail below. The typical orientation of these portions of the prodrug is as follows:
(stabilizing group)-(oligopeptide)-(optional linker group)-(therapeutic agent).

The stabilizing group is directly linked to the oligopeptide at a first attachment site of the oligopeptide. The oligopeptide is directly or indirectly linked to the therapeutic agent at a second attachment site of the oligopeptide. If the oligopeptide and the therapeutic agent are indirectly linked, then a linker group is present.

Direct linkage of two portions of the prodrug means a covalent bond exists between the two portions. The stabilizing group and the oligopeptide are therefore directly linked via a covalent chemical bond at the first attachment site of the oligopeptide, typically the N-terminus of the oligopeptide. When the oligopeptide and the therapeutic agent are directly linked then they are covalently bound to one another at the second attachment site of the oligopeptide. The second attachment site of the oligopeptide is typically the C-terminus of the oligopeptide, but may be elsewhere on the oligopeptide.

Indirect linkage of two portions of the prodrug means each of the two portions is covalently bound to a linker group. In an alternative embodiment, the prodrug has indirect linkage of the oligopeptide to the therapeutic agent. Thus, typically, the oligopeptide is covalently bound to the linker group which, in turn, is covalently bound to the therapeutic agent.

The prodrug of the invention is cleavable within its oligopeptide portion. The prodrug typically undergoes in vivo modification and an active portion, i.e., a transport-competent portion, of the prodrug enters the target cell. A first cleavage within the oligopeptide portion of the prodrug may leave a transport-competent portion of the prodrug as one of the cleavage products. Alternatively, further cleavage by one or more peptidases may be required to result in a portion of the prodrug that is capable of entering the cell. The active or transport-competent portion of the prodrug has at least the therapeutic agent and is that part of the prodrug which can enter the target cell to exert a therapeutic effect directly or upon further conversion within the target cell. Thus, the compound has an active portion, and the active portion is more capable of entering the target cell after cleavage by an enzyme associated with a target cell than prior to cleavage by the enzyme associated with a target cell.

The structures of the stabilizing group and oligopeptide are selected to limit clearance and metabolism of the prodrug by enzymes which may be present in blood or non-target tissue and are further selected to limit transport of the prodrug into cells. The stabilizing group blocks degradation of the prodrug and may act in providing preferable charge or other physical characteristics of the prodrug. The amino acid sequence of the oligopeptide is designed to ensure specific cleavage by an enzyme associated with a target cell, more specifically by a trouase enzyme, and even more specifically by Thimet oligopeptidase ("TOP").

It is desirable to make a therapeutic agent, especially an antitumor and/or anti-inflammatory therapeutic agent, inactive by modification of the therapeutic agent to a prodrug form. According to the invention, the target cells are usually tumor cells or cells participating in inflammatory reactions, especially those associated with rheumatic diseases, such as macrophages, neutrophils, and monocytes. Modification of the therapeutic agent to a prodrug form reduces some of the side effects of the therapeutic agents. Modification of the therapeutic agent to a prodrug form further allows for administration of an increased dosage of the therapeutic agent in prodrug form to the patient relative to the dosage of the therapeutic agent in unconjugated form.

In the target cell, the therapeutic agent (optionally attached to one or two amino acids and possibly also a linker group) acts either directly on its specific intracellular action site or, after a modification under the action of intracellular peptidases, kills the target cell or blocks its proliferation. Since normal cells release little to no TOP in vivo, the compound according to the invention is maintained inactive and does not enter the normal cells or does so in a relatively minor amount. Although TOP is believed to be widely distributed in the body, it is typically present as an intracellular enzyme. Therefore it is not generally accessible to peptide prodrugs in the circulation. In the environment of the tumor, TOP is believed to be released from necrotic tissue.

The prodrug is administered to the patient, carried through the blood stream in a stable form, and when in the vicinity of a target cell, is acted upon by TOP. Since the enzyme activity is only minimally present within the extracellular vicinity of normal cells, the prodrug is maintained and its active portion (including the therapeutic agent) gains entry into the normal cells only minimally, at best. In the vicinity of tumor or other target cells, however, the presence of TOP in the local environment causes cleavage of the prodrug. Once the stabilizing group is removed, further amino acids can be removed by other peptidases in the vicinity of target cells. The example shown in FIG. 2 depicts an N-capped tetrapeptide prodrug being cleaved extracellularly and gaining entry into the target cell. Once within the target cell, it may be further modified to provide therapeutic effect, such as by killing the target cell or blocking its proliferation. While the active portion of the prodrug may also enter the normal cells to some extent, the active portion is freed from the remainder of the prodrug primarily in the vicinity of target cells. Thus, toxicity to normal cells is minimized.

This process is particularly useful for, and is designed for, target cell destruction when the target tissue releases an enzyme that is not released by normal cells or tissue. Here "normal cells" means non-target cells that would be encountered by the prodrug upon administration of the prodrug in the manner appropriate for its intended use. Since normal (i.e., non-target) cells liberate little or none of the target-cell enzyme(s), e.g., TOP, that are responsible for cleaving the bond that links the active portion (including the therapeutic agent) of the prodrug from the remainder of the prodrug in vivo, the compound of the invention is maintained inactive and does not enter the normal cells.

In an alternative embodiment, the orientation of the prodrug may be reversed so that the stabilizing group is attached to the C-terminus of the oligopeptide and the therapeutic agent is directly or indirectly linked to the N-terminus of the oligopeptide. Thus, in an alternative embodiment, the first attachment site of the oligopeptide may be the C-terminus of the oligopeptide and the second attachment site of the oligopeptide may be the N-terminus of the oligopeptide. The linker group may optionally be present between the therapeutic agent and the oligopeptide. The alternative embodiment of the prodrug of the invention functions in the same manner as does the primary embodiment.

Target Cell Associated Enzymes

The prodrugs of the invention are designed to take advantage of preferential activation through interaction with an enzyme associated with the target cell, at or near the site targeted within the body of the patient. One such type of enzyme is trouase, described in greater detail in PCT/US99/30393, incorporated herein by reference.

Trouase is the type of enzyme that is thought to activate the prodrug at the target tissue. Trouase is a class of endopeptidases which shows a remarkable degree of discrimination between leucine and isoleucine at the carboxyl side of the oligopeptide cleavage site. A defining characteristic is that under appropriate assay conditions, a trouase readily cleaves Suc-βAla-Leu-Ala-Leu-Dnr while it is at least twenty-fold less active with Suc-βAla-Ile-Ala-Leu-Dnr. TOP is a member of the trouase class of enzymes.

Target cells are believed to release trouase. Most likely the enzyme is generated either by target cells or by normal cells that are associated with the target cells, such as stromal tissue, neutrophils, eosinophils, macrophages or B cells. The target cell associated enzyme may be associated with or bound on (at least the active site) the outer cell surface, secreted, released, or present in some other manner in the extracellular vicinity of the target cell. So, for example, the trouase may be secreted or present in some other manner in the extracellular vicinity of the target cell. In many cases, the prodrug of the invention includes a therapeutic agent for the treatment of cancer and the target cell is a tumor cell. Thus, the trouase may be secreted extracellularly by the tumor cell or it may be present extracellularly, e.g., because there is a fair amount of cell lysis associated with tumors generally. Cell lysis is also associated with inflammatory tissue, another target site.

Trouase activity is low in human plasma, however. Trouase activity has been observed in carcinoma cell extracts and conditioned media from cultured carcinoma cells, red blood cells and various human tissues, especially kidney. A partial purification scheme of trouase from HeLa (cervical carcinoma) cell homogenate ultracentrifugation (145,000×g 30 min) supernatant consists of four steps as follows:

1. Anion exchange chromatography using a 15 Q column (Pharmacia) eluted with a 0 to 0.5 M NaCl linear gradient in 20 mM triethylamine chloride pH 7.2, 0.01% Triton X-100, 2. Affinity chromatography using Chelating Sepharose Fast Flow (Pharmacia) pre-loaded with $CoCl_2$ and eluted with a 0 to 200 mM imidazole linear gradient in 10 mM sodium phosphate, 0.5 M NaCl, pH 7.2, 0.01% Triton X-100, 0.02% $NaN_3$,
3. Preparative native electrophoresis; and
4. Gel filtration high performance liquid chromatography using a 7.8 mm×60 cm TSK Gel G-3000SWXL (Toso-Haas) column eluted with 0.3 mL/min 50 mM potassium phosphate, 200 mM potassium sulfate, pH 7.0.

Further cleavage of the portion of the prodrug released after trouase cleavage may occur intracellularly or extracellularly, possibly by amino-exopeptidases. In vitro experiments indicate that amino-exopeptidases of broad specificities are present in human blood as well as the carcinoma cell environment.

Evidence now suggests that TOP is an example of a trouase. The trouase isolated from HeLa cell extracts and studied in conditioned media or homogenates from MCF-7/6 human carcinoma cells, catalyzes the initial cleavage of Suc-βAla-Leu-Ala-Leu-Dox. The trouase isolated from these sources is believed to be TOP. Both structural and functional evidence indicate that a trouase found in carcinoma cells is Thimet oligopeptidase or "TOP".

According to the literature, TOP, or EC 3.4.24.15 is a thiol-activated zinc metallopeptidase which catalyzes internal (endo) cleavage of various oligopeptides having 6 to 17 amino acids (Dando, et al., "Human thimet oligopeptidase," *Biochem J* 294:451-457 (1993)). It also is referred to as Pz-peptidase, collagenase-like peptidase, kininase A, amyloidin protease, and metalloendopeptidase 24.15. The enzyme has been isolated from chicken embryo (Morales, et al., "PZ-peptidase from chick embryos. Purification, properties, and action on collagen peptides," *J Biol Chem* 252:4855-4860 (1977)), chicken liver (Barrett, et al., "Chicken liver Pz-peptidase, a thiol-dependent metallo-endopeptidase," *Biochem J* 271:701-706 (1990)), rat testis (Orlowski, et al., "Endopeptidase 24.15 from rat testes. Isolation of the enzyme and its specificity toward synthetic and natural peptides, including enkephalin-containing peptides," *Biochem J* 261: 951-958 (1989)), and human erythrocytes (Dando, et al., "Human thimet oligopeptidase," *Biochem J* 294:451-457 (1993)). The gene for this enzyme has been cloned and DNA sequence obtained from human brain (Dovey et al., WO92/07068), rat testis (Pierotti, et al., "Endopeptidase-24.15 in rat hypothalamic/pituitary/gonadal axis," *Mol Cell Endocrinol* 76:95-103 (1991)) and pig liver (Kato, et al., "Cloning, amino acid sequence and tissue distribution of porcine thimet oligopeptidase. A comparison with soluble angiotensin-binding protein," *Eur J Biochem* 221:159-165 (1994)). TOP has been immunologically or functionally identified in extracts of HeLa (Krause, et al., "Characterization and localization of mitochondrial oligopeptidase (MOP) (EC 3.4.24.16) activity in the human cervical adenocarcinoma cell line HeLa," *J Cell Biochem* 66:297-308 (1997); AT-20 cells (Crack, et al., "The association of metalloendopeptidase EC 3.4.24.15 at the extracellular surface of the AtT-20 cell plasma membrane," *Brain Res* 835:113-124 (1999); Ferro, et al., "Secretion of metalloendopeptidase 24.15 (EC 3.4.24.15)," *DNA Cell Biol* 18:781-789 (1999); Garrido, et al., "Confocal microscopy reveals thimet oligopeptidase (EC 3.4.24.15) and neurolysin (EC 3.4.24.16) in the classical secretory pathway," *DNA Cell Biol* 18:323-331 (1999); Madin-Darby canine kidney cells (Oliveira, et al., "Characterization of thiol-, aspartyl-, and thiol-metallo-peptidase activities in madin-darby canine kidney cells," *J Cell Biochem* 76:478-488 (2000); and prostate cancer cell lines (Moody, et al., "Neurotensin is metabolized by endogenous proteases in prostate cancer cell lines," *Peptides* 19:253-258 (1998)).

Trouase purified from HeLa cells shows sequence identity with human TOP based on the mass-to-charge ratio of tryptic fragments covering 33% of all residues distributed over the full length of the known human enzyme sequence, as seen in Example 12. Immunoprecipitation using a specific anti-TOP antibody preparation with partially purified HeLa cell fraction (F1) and MCF-7/6 cell homogenate also indicates structural identity, as seen in Example 13. The size, by SDS polyacrylamide gel electrophoresis, of the 74 KD purified HeLa cell trouase is within the range reported for TOP. A minor 63 KD band, which co-purifies from HeLa cells, has not been previously reported and may be a proteolysis product of TOP formed during extraction. As seen in Example 9, the gel filtration estimated size of the native HeLa cell trouase is 68 KD rather than the reported TOP size of 78 KD; however, the difference may be explained by the inherent error of such native protein size estimation methods. The isoelectric point of the purified carcinoma cell trouase is 5.2, as seen in Example 9, which is within the range reported for TOP.

TOP and human carcinoma cell trouase show the same substrate specificity with nine different experimental compounds, as seen in Example 6. This specificity includes the ability to cleave Suc-βAla-Leu-Ala-Leu-Dox at approximately a twenty-fold faster rate than cleavage of Suc-βAla-Ile-Ala-Leu-Dox. The carcinoma cell trouase also has essentially the same pH optimum (see Example 11) and inhibitor profile (see Example 8) as TOP. As with TOP (Barrett et al., "Chicken liver Pz-peptidase, a thiol-dependent metallo-endopeptidase," *Biochem J* 271:701-706 (1990)) carcinoma cell trouase is inhibited by the metallopeptidase inhibitors EDTA and 1,10-phenanthroline but not serine, thiol, or acid proteinase inhibitors such as aminoethylbenzene-sulfonate, E64, pepstatin, leupeptin, aprotinin, CA074, or fumagillin. As reported for TOP, EDTA-treated carcinoma cell trouase is reactivated by $Co^{2+}$ (50-100 μM) or $Mn^{2+}$ (50-1000 μM). Although it is also possible to reactivate EDTA-deactivated chicken (Barrett, et al., "Chicken liver Pz-peptidase, a thiol-dependent metallo-endopeptidase," *Biochem J* 271:701-706 (1990)) or rat (Orlowski et al., "Endopeptidase 24.15 from rat testes. Isolation of the enzyme and its specificity toward synthetic and natural peptides, including enkephalin-containing peptides," *Biochem J* 261: 951-958 (1989)). TOP is also reactivated with $Zn^{2+}$; however, $Zn^{2+}$ reactivation is not seen with the EDTA-treated MCF-7/6 cell homogenate. The specific methods used for EDTA treatment and removal may affect the result with the carcinoma cell trouase. The fact that concentrations of $Zn^{2+}$ as low as 100 μM are inhibitory to TOP may also be a factor. $Zn^{2+}$ at 100 μM completely inhibits hydrolysis of Suc-βAla-Leu-Ala-Leu-Dox by HeLa cell Fraction 1. EDTA inactivated carcinoma cell trouase can not be reactivated with cupric ions. Finally, human cultured cell trouase demonstrates the unique thiol sensitivity of the TOP metalloendopeptidase, as seen in Example 10.

TOP activity may be inhibited in oxygenated solutions (such as blood) and activated in mildly reducing (hypoxic) environments, as demonstrated by thiol activation of air-inactivated preparations (Shrimpton, et al., "Thiol activation of endopeptidase EC 3.4.24.15. A novel mechanism for the regulation of catalytic activity," *J Biol Chem* 272: 17395-17399 (1997)). Accordingly, it is a useful enzyme for a general approach to designing prodrugs that are to be activated in hypoxic environments such as tumor tissue.

CD10 (CALLA, neprilysin, neutral endopeptidase, EC 3.4.24.11) is an oligopeptidase bound to the outer cell membrane of a number of cells including a limited number of cancer tumor types. Since it is also present in high concentrations in the brush boarder of the proximal kidney tubule, and at lower levels in some colon tissue and a number of immune system cells such as B-lymphocytes it may contribute to systemic activation of peptidyl prodrugs. This added systemic activation could lead to increased toxicity to normal tissues when compared to a peptidyl prodrug that is not a CD10 substrate. Su-βAla-Leu-Ala-Leu-Dox is a substrate for CD10 with cleavage occurring between Ala and Leu (AA2 and AA1) as shown in Example 17. CD10 cleaves poorly when glycine or alanine is present in the P1' cleavage site (Pozgay et al, Biochemistry (1986)) [see the CD10 patent under substrate specificity] thus Suc βAla-Leu-Ala-Gly-Dox and βAla-Leu-Ala-Ala-Dox are expected to be poorly cleaved by CD10. ON the other hand as shown below Suc-βAla-Leu-Ala-Gly-Dox (and presumably Suc-βAla-Leu-Ala-Ala-Dox are well cleaved by TOP. Thus, the preferred embodiment of this invention is a compound which is activated by TOP but not by CD10 as exemplified by Suc-βAla-Leu-Ala-Gly-Dox or Suc-βAla-Leu-Ala-Ala-Dox.

Ideally, when treating non-CD10 containing tumors the prodrug is not cleavable by the CD10 enzyme.

Stabilizing Group

An important portion of the prodrug is the stabilizing group, which serves to protect the prodrug compound from cleavage in circulating blood when it is administered to the patient and allows the prodrug to reach the vicinity of the target cell relatively intact. The stabilizing group typically protects the prodrug from cleavage by proteinases and peptidases present in blood, blood serum, and normal tissue. Particularly, since the stabilizing group caps the N-terminus of the oligopeptide, and is therefore sometimes referred to as an N-cap or N-block, it serves to ward against peptidases to which the prodrug may otherwise be susceptible.

Ideally, the stabilizing group is useful in the prodrug of the invention if it serves to protect the prodrug from degradation, i.e., cleavage, when tested by storage of the prodrug compound in human blood at 37° C. for 2 hours and results in less than 20%, preferably less than 2%, cleavage of the prodrug by the enzymes present in the human blood under the given assay conditions.

More particularly, the stabilizing group is either (1) other than an amino acid, or (2) an amino acid that is either (i) a non-genetically-encoded amino acid having four or more carbons or (ii) aspartic acid or glutamic acid attached to the N-terminus of the oligopeptide at the β-carboxyl group of aspartic acid or the γ-carboxyl group of glutamic acid.

For example, dicarboxylic (or a higher order carboxylic) acid or a pharmaceutically acceptable salt thereof may be used as a stabilizing group. Since chemical radicals having more than two carboxylic acids are also acceptable as part of the prodrug, the end group having dicarboxylic (or higher order carboxylic) acids is an exemplary N-cap. The N-cap may thus be a monoamide derivative of a chemical radical containing two or more carboxylic acids where the amide is attached onto the amino terminus of the peptide and the remaining carboxylic acids are free and uncoupled. For this purpose, the N-cap is preferably succinic acid, adipic acid, glutaric acid, or phthalic acid, with succinic acid being most preferred. Other examples of useful N-caps in the prodrug compound of the invention include diglycolic acid, fumaric acid, naphthalene dicarboxylic acid, pyroglutamic acid, acetic acid, 1- or 2-naphthylcarboxylic acid, 1,8-naphthyl dicarboxylic acid, aconitic acid, carboxycinnamic acid, triazole dicarboxylic acid, gluconic acid, 4-carboxyphenyl boronic acid, a $(PEG)_n$-analog such as polyethylene glycolic acid, butane disulfonic acid, maleic acid, isonipecotic acid, and nipecotic acid.

Additionally, intravascular administration of an aggregating positively charged prodrug in mice resulted in acute toxicity. However, no such toxicity was observed when the charge on this prodrug was reversed by derivitization with a negatively charged stabilizing group. This effect is discussed in greater detail below.

Thus, where aggregation of the therapeutic agent is a concern, it is preferred that the linked stabilizing group be negatively charged or neutral.

Acute Toxicity

Many cytotoxic compounds inherently have low solubility. Positively charged anthracyclines for example form aggregates at high concentration and these aggregates may induce intravenous coagulation when the aggregates are administered intravenously. Trouase recognizes a specific set of peptide sequences. When one of these hydrophobic sequences (e.g., βAla-Leu-Ala-Leu) is conjugated to a cytotoxic compound (for example: doxorubicin), it results in a less soluble compound which may form large aggregates when injected intravenously as a concentrated bolus. Since most peptides have exposed, positively-charged amino termini at physiological pH, these aggregates may form a polypositively charged surface in vivo. These aggregates given intravenously induce a coagulation cascade and death in mice within a few minutes (usually less than 30 min) of administration. This renders any positively charged prodrugs that are formulated in a way that produces aggregates in suspension unsuitable for therapeutic use.

Several experiments support the hypothesis that positively charged aggregates are formed with peptide conjugated doxorubicins. The examination of similarly formulated solutions by laser light scattering and size exclusion ultrafiltration demonstrated that only a small amount of the material had a molecular weight below 10 kD. The average molecular size of the aggregates were found to be around 70 kD. When the animals were concomitantly administered (see Example 22) heparin with the IV dose, the acute toxicity was greatly reduced or eliminated. When the animals were given dilute solutions of the same drug (same total dose), there was no acute toxicity. These results, taken together with literature reports, support the conclusion that peptide prodrugs of compounds that form aggregates because of insufficient solubility do not make optimal therapeutics. A solution to this aggregate problem makes these peptide prodrugs more practical. When these peptide prodrugs form aggregates because of insufficient solubility at the desired formulated concentrations, the stabilizing group on the peptide chain should terminate in a negatively charged or a neutral functionality. For example, the use of succinyl as a stabilizing group on the peptide prodrug alleviates the prodrug's acute toxicity (see Example 22). This solves an important problem in the use of peptide prodrugs as practical therapies for humans.

Oligopeptide

Oligopeptides are generally defined as polypeptides of short length, typically twenty amino acids or fewer. An oligopeptide useful in the prodrug of the invention is at least four amino acids in length, however. At the upper end, oligopeptides of less than or equal to twelve amino acids are most useful, although an oligopeptide may have a chain length greater than twelve amino acids and fall within both the definition of the term as generally recognized in the scientific field and additionally within the scope of the invention. Thus, the oligopeptide portion of the prodrug of the invention has four or more amino acids. Typically, the oligopeptide portion of the prodrug of the invention has four to twelve amino acids, inclusive. Preferably, it has four or five amino acids.

Numbering Scheme

The oligopeptide has a formula or sequence $(AA)_n$-$AA^4$-$AA^3$-$AA^2$-$AA^1$, wherein:
- each AA independently represents an amino acid;
- n is an integer from 0 to 16;
- $AA^4$ represents a non-genetically-encoded amino acid;
- $AA^3$ represents any amino acid;
- $AA^2$ represents any amino acid; and
- $AA^1$ represents any amino acid.

This corresponds to a position sequence P(n+2) ... P2-P1-P1'-P2'. The TOP is believed to cleave between the P1 and P1' positions. The oligopeptide is written in the conventional manner with the carboxyl-terminus (or C-terminus) at the right and the amino-terminus (or N-terminus) at the left. Thus, in the formula described above, $AA^1$ is the carboxyl-terminus.

Preferred Amino Acids

Unless otherwise indicated, all amino acids are in the L configuration. Although any amino acids may be present in the oligopeptide portion of the prodrug, with the exception of $AA^4$, which is a non-genetically-encoded amino acid serving a blocking function as described in further detail below, certain amino acids are preferred.

In the P2 position, i.e., $AA^4$, one of the following amino acids is most preferably present: β-Alanine, Thiazolidine-4-carboxylic acid, 2-Thienylalanine, 2-Naphthylalanine, D-Alanine, D-Leucine, D-Methionine, D-Phenylalanine, 3-Amino-3-phenylpropionic acid, γ-Aminobutyric acid, and 3-amino-4,4-diphenylbutyric acid. Tetrahydroisoquinoline-3-carboxylic acid, 4-Aminomethylbenzoic acid, nipecotic acid, isonipecotic acid, or Aminoisobutyric acid are also preferred in the P2 position.

In the P1 or $AA^3$ position, one of the following amino acids is most preferred: Leucine, Tyrosine, Phenylalanine, p-Cl-Phenylalanine, p-Nitrophenylalanine, Valine, Norleucine, Norvaline, Phenylglycine, Tryptophan, Tetrahydroisoquinoline-3-carboxylic acid, 3-Pyridylalanine, Alanine, Glycine, or Thienylalanine. Also preferred are Methionine, Valine, or Proline in the P1 position.

In the P1' position, $AA^2$ is most preferably selected from the following amino acids: Alanine, Leucine, Tyrosine, Glycine, Serine, 3-Pyridylalanine, 2-Thienylalanine, Norleucine, Homoserine, Homophenylalanine, p-Cl-phenylalanine, or p-Nitrophenylalanine. Also preferred in this position are Aminoisobutyric Acid, Threonine, and Phenylalanine.

In the P2' or $AA^1$ position, one of the following amino acids is most preferably present: Leucine, Phenylalanine, Isoleucine, Alanine, Glycine, Tyrosine, 2-Naphthylalanine, Serine, p-Cl-phenylalanine, p-Nitrophenylalanine, 1-Naphthylalanine, Threonine, Homoserine, Cyclohexylalanine, Thienylalanine, Homophenylalanine, or Norleucine. Also preferred is β-Alanine in the P2' position.

Oligopeptides especially useful in the prodrug of the invention include those shown in FIGS. 10A-10D, particularly one the following: D-AlaThiβAlaβAlaLeuAlaLeu (SEQ ID NO: 1), ThiβAlaβAlaLeuAlaLeu (SEQ ID NO: 2), βAlaβAla-LeuAlaLeu (SEQ ID NO: 3), βAlaAlaAlaIle (SEQ ID NO: 4), βAlaAlaAlaLeu (SEQ ID NO: 5), βAlaPheTyrLeu (SEQ ID NO: 6), βAlaPheThrPhe (SEQ ID NO: 7), βAlaPheGlyIle (SEQ ID NO: 8), βAlaPheGlyLeu (SEQ ID NO: 9), βAlaPhePhePhe (SEQ ID NO: 10), βAlaPhePheIle (SEQ ID NO: 11), βAlaPhePheLeu (SEQ ID NO: 12), βAlaPheAlaIle (SEQ ID NO: 13), βAlaPheAlaLeu (SEQ ID NO: 14), ThiGlyAla-Leu (SEQ ID NO: 15), NalGlyAlaLeu (SEQ ID NO: 16), βAlaLeuTyrLeu (SEQ ID NO: 17), βAlaLeuThiLeu (SEQ ID NO: 18), βAlaLeuThrPhe (SEQ ID NO: 19), βAlaLeuThrIle (SEQ ID NO: 20), βAlaLeuThrLeu (SEQ ID NO: 21), βAla-LeuSerLeu (SEQ ID NO: 22), βAlaLeuPyrLeu (SEQ ID NO: 23), βAlaLeuLeuLeu (SEQ ID NO: 24), βAlaLeuGlyPhe (SEQ ID NO: 25), βAlaLeuGlyIle (SEQ ID NO: 26), ThiLeuGlyLeu (SEQ ID NO: 27), βAlaLeuGlyLeu (SEQ ID NO: 28), AibLeuGlyLeu (SEQ ID NO: 29), βAlaLeuPheIle (SEQ ID NO: 30), βAlaLeuPheLeu (SEQ ID NO: 31), βAla-LeuAibLeu (SEQ ID NO: 32), βAlaLeuAlaAla (SEQ ID NO: 33), βAlaLeuAlaβAla (SEQ ID NO: 34), βAlaLeuAlaPhe (SEQ ID NO: 35), βAlaLeuAlaGly (SEQ ID NO: 36), βAla-LeuAlaIle (SEQ ID NO: 37), βAlaLeuAlaLeu (SEQ ID NO: 38), TicLeuAlaLeu (SEQ ID NO: 39), ThzLeuAlaLeu (SEQ ID NO: 40), ThiLeuAlaLeu (SEQ ID NO: 41), NalLeuAla-Leu (SEQ ID NO: 42), NAALeuAlaLeu (SEQ ID NO: 43), D-LeuLeuAlaLeu (SEQ ID NO: 44), D-AlaLeuAlaLeu (SEQ ID NO: 45), D-MetLeuAlaLeu (SEQ ID NO: 46), APPLeuAlaLeu (SEQ ID NO: 47), AmbLeuAlaLeu (SEQ ID NO: 48), βAlaLeuAlaNal (SEQ ID NO: 49), βAlaLeuAlaSer (SEQ ID NO: 50), βAlaLeuAlaTyr (SEQ ID NO: 51), βAl-aMetTyrPhe (SEQ ID NO: 52), βAlaMetTyrLeu (SEQ ID NO: 53), βAlaMetGlyIle (SEQ ID NO: 54), ThiMetGlyLeu (SEQ ID NO: 55), βAlaMetPhePhe (SEQ ID NO: 56), βAl-aMetPheIle (SEQ ID NO: 57), TicMetAlaLeu (SEQ ID NO: 58), NalMetAlaLeu (SEQ ID NO: 59), NAAMetAlaLeu (SEQ ID NO: 60), βAlaMetAlaLeu (SEQ ID NO: 61), APP-MetAlaLeu (SEQ ID NO: 62), βAlaNleTyrIle (SEQ ID NO: 63), βAlaNleTyrLeu (SEQ ID NO: 64), βAlaNleThrIle (SEQ ID NO: 65), βAlaNleThrLeu (SEQ ID NO: 66), βAlaNleG-lyPhe (SEQ ID NO: 67), βAlaNleGlyIle (SEQ ID NO: 68), βAlaNleGlyLeu (SEQ ID NO: 69), βAlaNlePheIle (SEQ ID NO: 70), βAlaNleAlaIle (SEQ ID NO: 71), βAlaNleAlaLeu (SEQ ID NO: 72), βAlaNleAlaPhe (SEQ ID NO: 73), βAl-aNvaAlaLeu (SEQ ID NO: 74), βAlaPheTyrIle (SEQ ID NO: 75), ThiProGlyLeu (SEQ ID NO: 76), ThiProAlaLeu (SEQ ID NO: 77), NalProAlaLeu (SEQ ID NO: 78), βAlaProAla-Leu (SEQ ID NO: 79), βAlaPhe(Cl), AlaLeu (SEQ ID NO: 80), βAlaPhe($NO_2$), AlaIle (SEQ ID NO: 81), βAlaPhe($NO_2$), AlaLeu (SEQ ID NO: 82), βAlaPhgAlaLeu (SEQ ID NO: 83), βAlaPyrAlaLeu (SEQ ID NO: 84), TicThrGlyLeu (SEQ ID NO: 85), βAlaThiGlyIle (SEQ ID NO: 86), βAl-aThiAlaLeu (SEQ ID NO: 87), βAlaTicAlaIle (SEQ ID NO: 88), βAlaTicAlaLeu (SEQ ID NO: 89), βAlaValAlaLeu (SEQ ID NO: 90), βAlaTrpAlaLeu (SEQ ID NO: 91), βAl-aTyrTyrPhe (SEQ ID NO: 92), βAlaTyrTyrIle (SEQ ID NO: 93), βAlaTyrTyrLeu (SEQ ID NO: 94), βAlaTyrThrLeu (SEQ ID NO: 95), βAlaTyrPheLeu (SEQ ID NO: 96), βAl-aTyrGlyIle (SEQ ID NO: 97), ThiTyrGlyLeu (SEQ ID NO: 98), βAlaTyrGlyLeu (SEQ ID NO: 99), βAlaTyrPheIle (SEQ ID NO: 100), βAlaTyrAlaIle (SEQ ID NO: 101), ThiTyrAla-Leu (SEQ ID NO: 102), and βAlaTyrAlaLeu (SEQ ID NO: 103).

Blocking Amino Acid

The oligopeptide portion of the prodrug includes a blocking amino acid as $AA^4$ of the oligopeptide sequence, i.e. at position P2 of the position sequence, according to the numbering scheme described above. The blocking amino acid is a non-genetically-encoded amino acid.

The function of the blocking amino acid at position P2 is to maintain selectivity for cleavage of the prodrug by TOP and inhibit cleavage of the oligopeptide by, or at least avoid providing a cleavage site for, other enzymes in that portion of the oligopeptide most closely linked (directly linked or indirectly linked) to the therapeutic agent portion of the prodrug compound. More particularly, by placing a blocking amino acid at position P2, undesired cleavage within the peptide linkages of the four amino acids of the oligopeptide sequence $AA^4$-$AA^3$-

AA²-AA¹ and position sequence P2-P1-P1'-P2' is reduced. It is believed that trouase cleaves between the P1 and P1' positions of the oligopeptide. Since it is known that blood and normal cells are associated with a variety of peptidases, placing a blocking amino acid at position P2 serves to protect the oligopeptide portion of the prodrug in vivo until the prodrug is in the vicinity of the target cell. Specifically, by placing a blocking amino acid at position P2, it is believed that the oligopeptide is protected from undesired cleavage between P2 and P1. Without the blocking amino acid, the prodrug might be vulnerable to both exopeptidases and endopeptidases present in blood and normal tissue, both classes of enzymes which might otherwise degrade the prodrug before it reaches its target. Example 14 below illustrates this important feature of the prodrug.

Screening with Top

TOP is an important enzyme that may be utilized for selecting oligopeptides for further use and, therefore, another aspect of the invention is an oligopeptide cleavable by TOP of the formula $(AA)_n$-AA⁴-AA³-AA²-AA¹, wherein:

each AA independently represents an amino acid,
n is an integer from 0 to 16,
AA⁴ represents a non-genetically-encoded amino acid,
AA³ represents any amino acid,
AA² represents any amino acid, and
AA¹ represents any amino acid.

The oligopeptide may be linked to a therapeutic agent and/or a stabilizing group when testing for cleavability by TOP.

Therapeutic Agents

Therapeutic agents that are particularly advantageous to modify to a prodrug form according to the invention are those with a narrow therapeutic window. A drug or therapeutic agent with a narrow therapeutic window is one in which the dose at which toxicity is evident, by general medical standards, is very close to the dose at which efficacy is evident.

The therapeutic agent conjugated to the stabilizing group and oligopeptide and, optionally, the linker group to form the prodrug of the invention may be useful for treatment of cancer, inflammatory disease, or some other medical condition. Preferably, the therapeutic agent is selected from the following classes of compounds:

Alkylating Agents, Antiproliferative agents, Tubulin Binding agents, Vinca Alkaloids, Enediynes, Podophyllotoxins or Podophyllotoxin derivatives, the Pteridine family of drugs, Taxanes, Anthracyclines, Dolastatins, Topoiosomerase inhibitors, Mytansinoids, and Platinum coordination complex chemotherapeutic agents.

Particularly, the therapeutic agent is advantageously selected from the following compounds or a derivative or analog thereof: Doxorubicin, Daunorubicin, Vinblastine, Vincristine, Calicheamicin, Etoposide, Etoposide phosphate, CC-1065, Duocarmycin, KW-2189, Methotrexate, Methopterin, Aminopterin, Dichloromethotrexate, Docetaxel, Paclitaxel, Epithiolone, Combretastatin, Combretastatin A4 Phosphate, Dolastatin 10, Dolastatin 11, Dolastatin 15, Topotecan, Camptothecin, Mitomycin C, Porfiromycin, 5-Fluorouracil, 6-Mercaptopurine, Fludarabine, Tamoxifen, Cytosine arabinoside, Adenosine Arabinoside, Colchicine, Carboplatin, Mitomycin C, Bleomycin, Melphalan, Cyclosporin A, Chloroquine, Maytansine or Cisplatin. By derivative is intended a compound that results from reacting the named compound with another chemical moiety, and includes a pharmaceutically acceptable salt, acid, base or ester of the named compound. By analog is intended a compound having similar structural and functional properties, such as biological activities, to the named compound.

Linker Groups

A linker group between the oligopeptide and the therapeutic agent may be advantageous for reasons such as the following:

1. As a spacer for steric considerations in order to facilitate enzymatic release of the AA¹ amino acid or other enzymatic activation steps.
2. To provide an appropriate attachment chemistry between the therapeutic agent and the oligopeptide.
3. To improve the synthetic process of making the prodrug conjugate (e.g., by pre-derivitizing the therapeutic agent or oligopeptide with the linker group before conjugation to enhance yield or specificity.)
4. To improve physical properties of the prodrug.
5. To provide an additional mechanism for intracellular release of the drug.

Linker structures are dictated by the required functionality. Examples of potential linker chemistries are hydrazide, ester, ether, and sulphydryl. Amino caproic acid is an example of a bifunctional linker group. When amino caproic acid is used in the linker group, it is not counted as an amino acid in the numbering scheme of the oligopeptide.

The optionally present linker group is not cleavable by TOP, i.e. it is not cleavable by TOP under physiological conditions An especially useful embodiment is a compound that is cleavable by a trouase but resistant to cleavage by CD10 or other systemic or blood enzymes.

Prodrug Design

A method of designing a prodrug is another aspect of the invention and entails initially identifying an oligopeptide as described above. Then the oligopeptide is linked at a first attachment site of the oligopeptide to a stabilizing group that hinders cleavage of the oligopeptide by enzymes present in whole blood, and directly or indirectly linked to a therapeutic agent at a second attachment site of the oligopeptide. The linkage of the oligopeptide to the therapeutic agent and the stabilizing group may be performed in any order or concurrently. The resulting conjugate is tested for cleavability by TOP. The resulting conjugate may also be tested for stability in whole blood. Test compounds stable in whole blood are selected.

The first attachment site is usually the N-terminus of the oligopeptide but may be the C-terminus of the oligopeptide or another part of the oligopeptide. The second attachment site is usually the C-terminus of the oligopeptide, but may be the N-terminus of the oligopeptide or another part of the oligopeptide. A prodrug designed by such a method is also part of the invention.

Further, the invention includes a method for decreasing toxicity of a therapeutic agent that is intended for administration to a patient. Specifically, a modified, prodrug form of the therapeutic agent is formed by directly or indirectly linking the therapeutic agent to an oligopeptide cleavable by a trouase, or more specifically, cleavable by TOP. The oligopeptide is also linked to a stabilizing group. The prodrug thus formed provides for decreased toxicity of the therapeutic agent when administered to the patient. The modification of the therapeutic agent in this manner also allows for administration of an increased dosage of the therapeutic agent to the patient relative to the dosage of the therapeutic agent in unconjugated form.

Pharmaceutical Compositions

The invention also includes a pharmaceutical composition comprising a compound, particularly a prodrug compound, according to the invention and, optionally, a pharmaceutically acceptable carrier, for example an adjuvant or vehicle, or the like.

The invention also relates to the use of the pharmaceutical composition for the preparation of a medicinal product intended for the treatment of a medical condition.

The pharmaceutical composition may, for example, be administered to the patient parenterally, especially intravenously, intramuscularly, or intraperitoneally. Pharmaceutical compositions of the invention for parenteral administration comprise sterile, aqueous or nonaqueous solutions, suspensions, or emulsions. As a pharmaceutically acceptable solvent or vehicle, propylene glycol, polyethylene glycol, injectable organic esters, for example ethyl oleate, or cyclodextrins may be employed. Isotonic saline may be part of the pharmaceutical composition. These compositions can also comprise wetting, emulsifying and/or dispersing agents.

The sterilization may be carried out in several ways, for example using a bacteriological filter, by incorporating sterilizing agents in the composition or by irradiation. They may also be prepared in the form of sterile solid compositions which may be dissolved at the time of use in sterile water or any other sterile injectable medium.

The pharmaceutical composition may also comprise adjuvants which are well known in the art (e.g., vitamin C, antioxidant agents, etc.) and capable of being used in combination with the compound of the invention in order to improve and prolong the treatment of the medical condition for which they are administered.

Doses for administration to a patient of the compounds according to the invention are generally at least the usual doses of the therapeutic agents known in the field, described in Bruce A. Chabner and Jerry M. Collins, *Cancer Chemotherapy*, Lippincott Ed., ISBN 0-397-50900-6 (1990) or they may be adjusted, within the judgment of the treating physician, to accommodate the superior effectiveness of the prodrug formulations or the particular circumstances of the patient being treated. The doses administered hence vary in accordance with the therapeutic agent used for the preparation of the compound according to the invention.

Treatment with Prodrug Compound

A method for the therapeutic treatment of a medical condition that involves administering, especially parenterally or intravenously, to the patient a therapeutically effective dose of the pharmaceutical composition is also within the scope of the invention. Thus, a method for treating a patient includes administering to the patient a therapeutically effective amount of a compound comprising:

(1) a therapeutic agent capable of entering a target cell,
(2) an oligopeptide of the formula $(AA)_n\text{-}AA^4\text{-}AA^3\text{-}AA^2\text{-}AA^1$, wherein:
 each AA independently represents an amino acid,
 n is an integer from 0 to 16,
 $AA^4$ represents a non-genetically-encoded amino acid,
 $AA^3$ represents any amino acid,
 $AA^2$ represents any amino acid, and
 $AA^1$ represents any amino acid,
(3) a stabilizing group, and
(4) optionally, a linker group not cleavable by TOP,
wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide,
wherein the stabilizing group hinders cleavage of the compound by enzymes present in whole blood, and
wherein the compound is cleavable by an enzyme associated with the target cell. The enzyme associated with the target cell is preferably a trouase and, more preferably, TOP.

The prodrug compound is useful for the treatment of many medical conditions including cancer, neoplastic diseases, tumors, inflammatory diseases, and infectious diseases. Examples of preferred diseases are breast cancer, colorectal cancer, liver cancer, lung cancer, prostate cancer, ovarian cancer, brain cancer, and pancreatic cancer. The prodrug compound of the invention is also useful in addressing the problem of multi-drug resistant target cells.

For example, following repeated chemotherapy, many tumor cells develop multi-drug resistance (MDR). MDR can be evident both in vitro and clinically, and is especially evident in the case of doxorubicin and other adriamycin analogs. There are various underlying mechanisms of action of MDR that generally involve changes in expression or activity of a range of transport-associated cell membrane proteins. These include the P-glycoprotein pump, which actively transports doxorubicin or other therapeutic agent out of cells. In tumors that develop MDR, the effective dose to kill tumor cells increases until it approaches the overall toxic dose. Thus, otherwise very effective chemotherapeutics are no longer useful as drugs, due to unacceptable side-effect levels and lethality. A chemotherapeutic or other therapeutic agent modified to form a prodrug as taught herein is useful, however, in counteracting such resistance of a target cell to the therapeutic agent.

Thus, a method of treating resistance to a therapeutic agent in a patient in need of such treatment, the method comprises: administering to the patient a therapeutically effective amount of a compound comprising:

(1) a therapeutic agent capable of entering a target cell,
(2) an oligopeptide of the formula $(AA)_n\text{-}AA^4\text{-}AA^3\text{-}AA^2\text{-}AA^1$, wherein:
 each AA independently represents an amino acid,
 n is an integer from 0 to 16,
 $AA^4$ represents a non-genetically-encoded amino acid,
 $AA^3$ represents any amino acid,
 $AA^2$ represents any amino acid, and
 $AA^1$ represents any amino acid,
(3) a stabilizing group, and
(4) optionally, a linker group not cleavable by TOP,
wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide,
wherein the stabilizing group hinders cleavage of the compound by enzymes present in whole blood, and
wherein the compound is cleavable by TOP.

Formulated in pharmaceutically acceptable vehicles (such as isotonic saline), the prodrug compound can be administered to animals or humans in intravenous doses ranging from 0.05 mg/kg/dose/day to 300 mg/kg/dose/day. It can also be administered via intravenous drip or other slow infusion method. Human patients are the usual recipients of the prodrug of the invention, although veterinary usage is also contemplated.

Diagnosis or Assay

An article of manufacture, such as a kit, for diagnosis or assay is also within the scope of the invention. Such an article of manufacture would preferably utilize a compound as described above, except that a marker, such as coumarin is conjugated to the oligopeptide and stabilizing group instead of a therapeutic agent. A marker intends any moiety that can be conjugated to the oligopeptide and is readily detectable by any method known in the art. At least one reagent useful in the detection of the marker is typically included as part of the kit. Thus, the article of manufacture would include the following:

(1) a compound comprising:
  (a) a marker,
  (b) an oligopeptide of the formula $(AA)_n$-$AA^4$-$AA^3$-$AA^2$-$AA^1$, wherein:
    each AA independently represents an amino acid,
    n is an integer from 0 to 16,
    $AA^4$ represents a non-genetically-encoded amino acid,
    $AA^3$ represents any amino acid,
    $AA^2$ represents any amino acid, and
    $AA^1$ represents any amino acid,
  (c) a stabilizing group, and
  (d) optionally, a linker group not cleavable by TOP,
  wherein the oligopeptide is directly linked to the stabilizing group at a first attachment site of the oligopeptide and the oligopeptide is directly linked to the marker or indirectly linked through the linker group to the marker at a second attachment site of the oligopeptide,
  wherein the stabilizing group hinders cleavage of the compound by enzymes present in whole blood, and
  wherein the compound is cleavable by TOP, and
(2) optionally at least one reagent useful in the detection of said marker.

The article of manufacture may be used, for example, with patient samples to diagnose tumors or to identify patients susceptible to treatment by prodrug therapy.

Process Chemistry General Procedures

Oligopeptide: General Method for the Synthesis of Peptides

The peptide, or oligopeptide, sequences in the prodrug conjugates of this invention may be synthesized by the solid phase peptide synthesis (using either Boc or Fmoc chemistry) methods or by solution phase synthesis. The general Boc and Fmoc methods are widely used and are described in the following references: Merrifield, *J. A. Chem. Soc.*, 88:2149 (1963); Bodanszky and Bodanszky, *The Practice of Peptide Synthesis*, Springer-Verlag, Berlin, 7-161 (1994); Stewart, *Solid Phase Peptide Synthesis*, Pierce Chemical, Rockford, (1984).

General Fmoc Solid Phase Method

Figure 3:
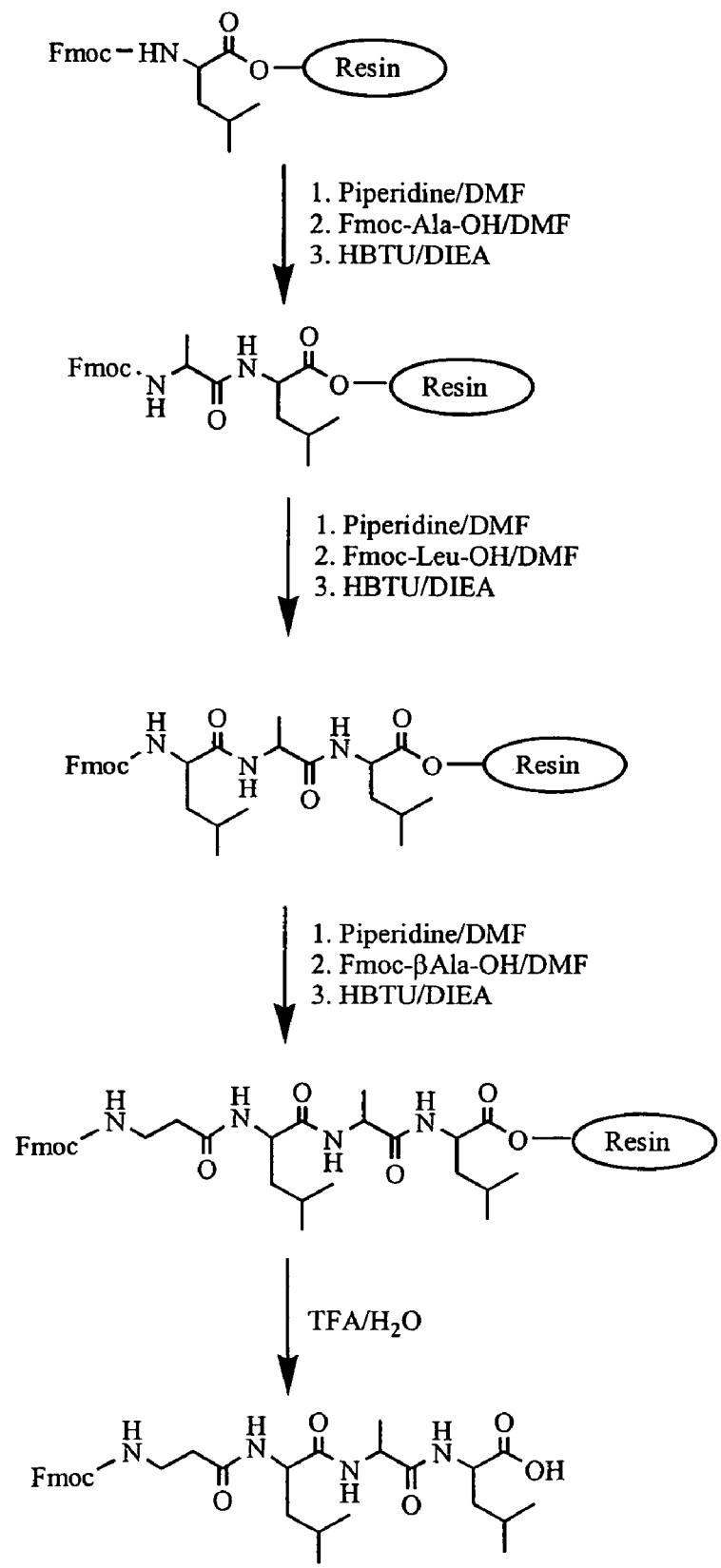
FIG. 3 illustrates a synthesis of Fmoc-βAla-Leu-Ala-Leu, a typical intermediate of the invention.

Using the preferred solid phase synthesis method, either automated or manual, a peptide of desired length and sequence is synthesized through the stepwise addition of amino acids to a growing chain which is linked to a solid resin. Examples of useful Fmoc compatible resins include, but are not limited to, Wang resin, HMPA-PEGA resin, Rink acid resin, or a hydroxyethyl-photolinker resin. The C-terminus of the peptide chain is covalently linked to a polymeric resin and protected α-amino acids were added in a stepwise manner with a coupling reagent. A preferred α-amino protecting group is the Fmoc group, which is stable to coupling conditions and can readily be removed under mild alkaline conditions. The reaction solvents are preferably, but not limited to, DMF, NMP, DCM, MeOH, and EtOH. Examples of coupling agents are: DCC, DIC, HATU, HBTU. Cleavage of the N-terminal protecting group is accomplished in 10-100% piperidine in DMF at 0-40° C., with ambient temperature being preferred. At the end of synthesis, the final Fmoc protecting group is removed using the above N-terminal cleavage procedure. The remaining peptide on resin is cleaved from the resin along with any acid sensitive side chain protecting groups by treating the resin under acidic conditions. For example an acidic cleavage condition is a mixture of trifluoroacetic acid (TFA) in dichloromethane. If the hydroxyethyl-photolinker resin is used, the appropriate wavelength for inducing cleavage is λ 365 nm ultraviolet light. A diagramatic representation of this process is given in FIG. 3.

General N-Cap Method Via Solid Phase Synthesis

The preparation of N-terminus derivatized peptides is conveniently accomplished on solid phase. When the peptide synthesis is complete, the terminal Fmoc is removed while the peptide is still on the solid support. The N-cap of choice is coupled next using standard peptide coupling conditions onto the N-terminus of the peptide. On completion of the N-cap coupling the peptide is cleaved from the resin using the procedure described above.

General Boc Solid Phase Method

For the solid phase method using Boc chemistry, either the Merrifield resin or PAM resin is useful. The amino acids are coupled to the growing chain on solid phase by successive additions of coupling agent activated Boc-protected amino acids. Examples of coupling agents are: DCC, DIC, HATU, HBTU. The reaction solvents may be DMF, DCM, MeOH, and NMP. Cleavage of the Boc protecting group is accomplished in 10-100% TFA in DCM at 0-40° C., with ambient temperature being preferred. On completion of the peptide chain assembly the N-terminus protecting group (usually Boc) is removed as described above. The peptide is removed from the resin using liquid HF or trifluoromethane sulfonic acid in dichloromethane.

General Procedure for the Preparation of Fmoc Oligopeptide by Solution Phase Synthesis Alternatively, the prodrug peptide intermediate may be made via a solution phase synthesis, utilizing either Boc or Fmoc chemistry. In the diagrammatic presentation of the methods (FIG. 4), the C-terminal Leu tetrapeptide is generally used as an example, but it will be understood that similar reactions may be performed with other C-terminal tetrapeptides, as well. The peptide can be built up by the stepwise assembly in analogy to the solid phase method (in the N-terminal direction or in the C-terminal direction) or through the coupling of two suitably protected dipeptides or a tripeptide with a single amino acid.

Figure 4:
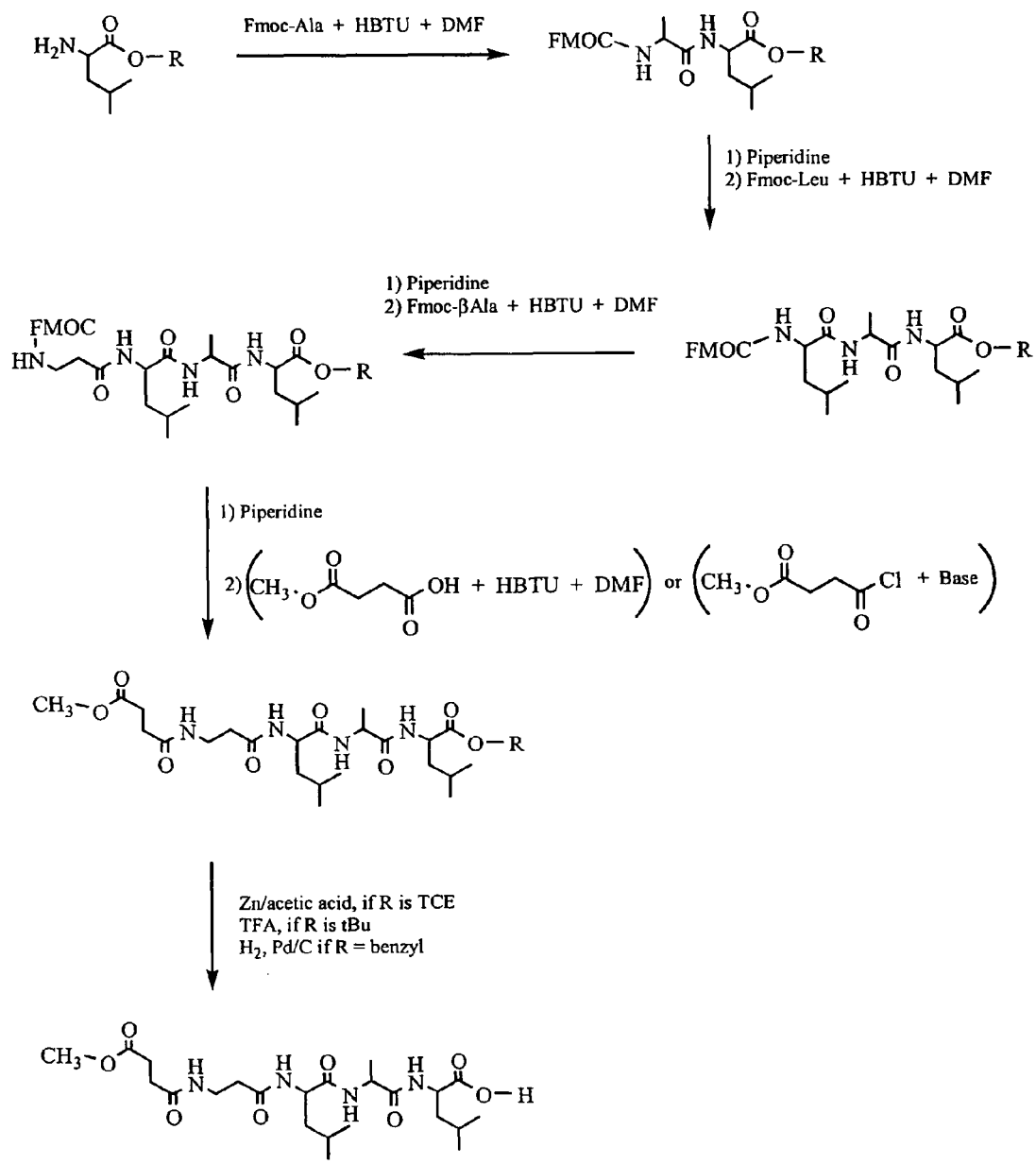
FIG. 4 illustrates an "Fmoc-route" synthesis of Methyl-succinyl-βAla-Leu-Ala-Leu, a typical intermediate of the invention.

One method of solution phase synthesis is a stepwise building up of the prodrug peptide intermediate using Fmoc chemistry, shown in FIG. 4. The C-terminus must be protected to reduce the formation of side products. The C-terminal R group in FIG. 4 is Me, tBu, benzyl or TCE. (Note when the N-cap is methyl succinyl the C-terminus R group cannot be Methyl.) Although DMF is given as the solvent, other solvents such as DMSO, $CH_3CN$, or NMP (or mixtures thereof) may be substituted therefor. Pyridine, $Et_3N$ or other bases may be substituted for piperidine in deprotecting the growing peptide chain protected amino terminus. Similarly, although HBTU is given in the diagram above as the activating agent, other activating agents such as DCC, DIC, DCC+HOBt, OSu, activated esters, azide, or triphenyl phosphoryl azide may be used. Additionally, the protected peptide acid chloride or acid bromide may be used to couple directly to the amino acid or peptide fragment. On completion of the oligopeptide assembly the N-terminus deprotected and the C-terminus protected peptide is ready to accept the desired N-cap.

General Procedure for the Preparation of N-Cap Oligopeptide Via Solution Phase Synthesis When constructing the N-capped oligopeptide by solution phase synthesis, the N-cap needs to be synthesized by a slightly modified procedure (FIG. 4). First the C-terminus of the Fmoc oligopeptide needs to be protected with an acid labile or hydrogenation sensitive protecting group compatible with the selective deprotection of the C-terminus over the N-cap. Then the Fmoc protecting group needs to be removed from the oligopeptide to reveal the N-terminus. With the N-terminus deprotected and the C-terminus protected, the oligopeptide is reacted with the activated hemiester of the desired N-cap. The N-cap can be activated using methods for activating amino acids such as DCC or HATU in base and an appropriate solvent. Alternatively, where the methyl-hemisuccinate is used, the coupling may also be done via methyl hemisuccinyl chloride (or other acid halide) (FIG. 4) using an inert solvent in the presence of an organic or inorganic base, such as DIEA, triethylamine or $Cs_2CO_3$. One example of such a synthesis can be by reacting methyl-hemisuccinate and βAla-Leu-Ala-Leu benzyl ester. The coupling method can be any one of the methods generally used in the art (see for example: Bodanszky, M., *The Practice of Peptide Synthesis*, Springer Verlag, 185 (1984); Bodanszky, M., *Principles of Peptide Synthesis*, Springer Verlag, 159 (1984). The benzyl group then can be removed by catalytic hydrogenation providing the desired N-cap methyl-succinyl form of βAla-Leu-Ala-Leu. Other examples of suitable, selectively removable C-terminal protecting groups can be, but are not limited to, tBu, alkoxy-methyl and TCE. Other methods of accomplishing this step are described in the literature.

Any combination of the above method can be considered, such as "fragment condensation" of di-, or tripeptides. The reaction conditions are well known in the art and detailed in the citations given. The advantage of the above described methods is the facile purification of the product produced by solution phase synthesis.

Prodrug Conjugate

General Methods for the Conjugation and Deprotection Steps

Figure 5:
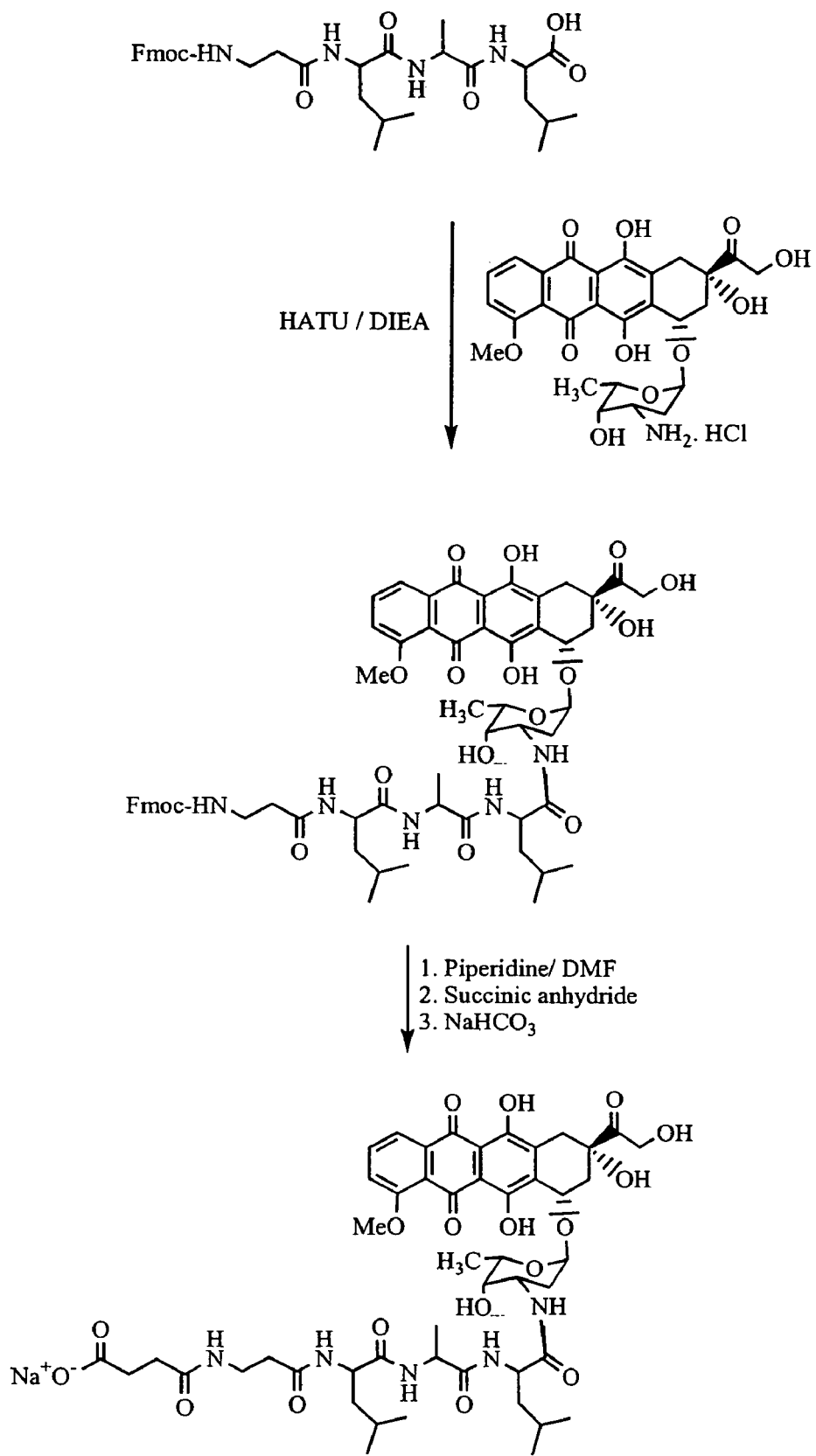
FIG. 5 illustrates an "Fmoc route" synthesis of a salt form of Suc-βAla-Leu-Ala-Leu-DOX, a typical compound of the invention.

The N-cap form of the oligopeptide-therapeutic agent described in this invention can be synthesized by coupling an Fmoc form (which means Fmoc is attached to the N-terminus of the oligopeptide) of the oligopeptide with daunorubicin, doxorubicin, or any appropriate therapeutic agent using any of the standard activating reagents used in peptide synthesis (FIG. 5). The solvent may be toluene, ethyl acetate, DMF, DMSO, $CH_3CN$, NMP, THF, DCM or any other suitable inert solvent as is known in the art and the reagents are soluble therein. The preferred solvents are DMF and NMP. The appropriate temperature range is −25 to +25° C., with ambient temperature being preferred. The activating agent may be selected from one of the following: PyBOP, HBTU, HATU, EDC, DIC, DCC, DCC+HOBT, OSu activated esters, azide, or triphenylphosphorylazide. HBTU or HATU is the preferred activating agent. Alternatively, the acid chloride or the acid bromide of the protected peptide can also be used for this coupling reaction. 2-4 equivalent, advantageously 2-2.5 equivalent of a base is required for the coupling reaction. The base can be selected from inorganic bases such as $CsCO_3$, Na— or $K_2CO_3$, or organic bases, such as TEA, DIEA, DBU, DBN, DBO, pyridine, substituted pyridines, N-methyl-morpholine etc., preferably TEA, or DIEA. The reaction can be carried out at temperatures between −15° C. and 50° C., advantageously between −10° C. and 10° C. The reaction time is between 5-90 minutes and is advantageously 20-40 minutes. The product is isolated by pouring the reaction mixture into water and filtering the precipitate formed. The crude product can be further purified by recrystallization from DCM, THF, ethyl acetate, or acetonitrile, preferably from dichloromethane or acetonitrile. The isolated Fmoc form of the oligopeptide therapeutic agent conjugate is then deprotected over 2-90 minutes, preferably 3-8 minutes, using a ten- to hundred-fold excess of base at a temperature between −10° C. and 50° C. Ideally, 5-60 equivalents of the base are preferred. Piperidine is the preferred base to deprotect Fmoc groups. The deprotected amino terminus of the oligopeptide therapeutic agent conjugate is acylated by a diacid anhydride as an activated hemi-ester to give the final N-cap form of the oligopeptide-therapeutic agent.

Figure 6:
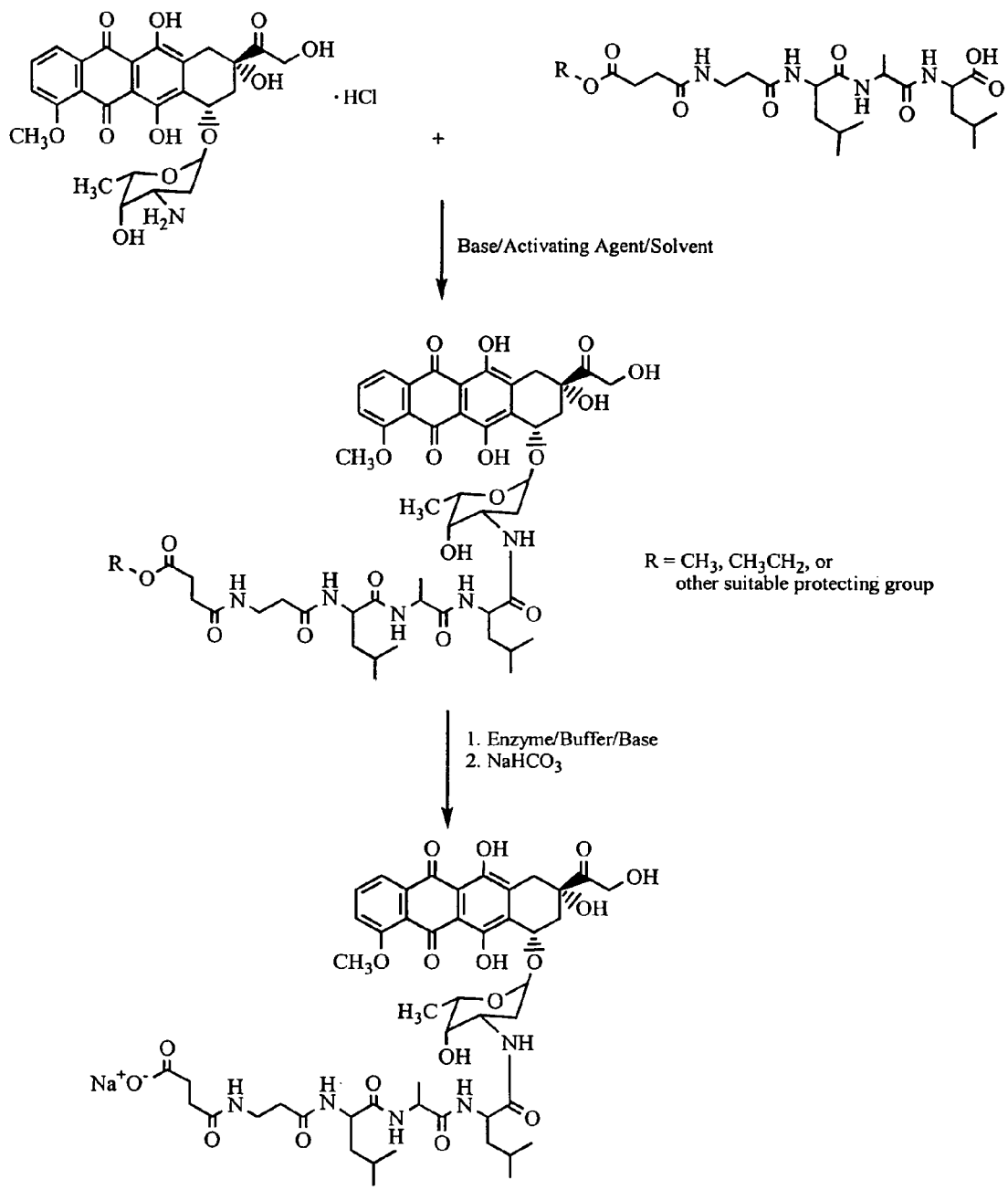
FIG. 6 illustrates an "Ester route" synthesis of a salt form of Suc-βAla-Leu-Ala-Leu-DOX, a typical compound of the invention.

Alternatively, the final prodrug can be similarly prepared from the protected N-cap form of the oligopeptide such as a methyl-hemi ester form of succinyl-N-cap oligopeptide and conjugated to a therapeutic agent. This method is illustrated in FIG. 6.

The protected N-Cap-oligopeptide therapeutic agent is now deprotected by methods compatible to the stability of the therapeutic agent. For example, anthracyclines may be, protected with a methyl group and deprotected with an esterase. For other therapeutic agents, benzyl protecting groups and catalytic hydrogenation may be chosen to deprotect.

Conversion to the salt form of the negatively charged N-cap oligopeptide therapeutic agent is carried out with a solvent selected from the following group: alcohol (including methanol, ethanol, or isopropanol), water, acetonitrile, tetrahydrofuran, diglyme or other polar solvents. The sodium source is one molar equivalent of $NaHCO_3$, NaOH, $Na_2CO_3$, NaOAc, $NaOCH_3$ (in general sodium alkoxide), or NaH. An ion exchange column charged with $Na^+$ (such as strong or weak ion exchangers) is also useful for this last step of making the salt form of the N-cap oligopeptide therapeutic agent when appropriate. Sodium is described as an example only.

Generally, the prodrug may be converted to a pharmaceutically acceptable salt form to improve solubility of the prodrug. The N-cap-oligopeptide therapeutic agent is neutralized with a pharmaceutically acceptable salt, e.g., $NaHCO_3$, $Na_2CO_3$, NaOH tris(hydroxymethyl)aminomethane, $KHCO_3$, $K_2CO_3$, $CaCO_3$, $NH_4OH$, $CH_3NH_2$, $(CH_3)_2NH$, $(CH_3)_3N$, acetyltriethylammonium. The preferred salt form of prodrug is sodium and the preferred neutralizing salt is $NaHCO_3$.

It is well documented that anthracycline type molecules, including doxorubicin and daunorubicin form gels in organic solvents in very low concentrations (Matzanke, et al., *Eur. J. Biochem.* 207:747-55 (1992); Chaires, et al., *Biochemistry* 21:3927-32 (1982); Hayakawa, et al., *Chem. Pharm. Bull.* 39:1282-6 (1991). This may be a considerable obstacle to getting high yields of clean product when making peptide anthracycline conjugates. The gel formation contributes to the formation of undesirable side reactions. One way to minimize this problem is to use very dilute solutions (1-2%) for the coupling reaction, however it is not practical in a process environment (large amounts of waste, complicated isolation). To overcome this problem, urea or other chaotropic agents may be used to break up the strong hydrophobic and hydrogen bonding forces forming the gel. Thus if the coupling reaction is carried out in a urea-containing solvent, advantageously a 20% to saturated solution of urea in DMF or NMP, the side reactions can be kept below 2% even if the concentration of reactants exceeds 10%. This makes the conjugation step practical at high concentrations and produces good yields.

General Enzyme Method

Hydrolysis of protected N-cap-oligopeptide therapeutic agents to the full N-cap compound catalyzed by acids or bases leads to complex reaction mixtures due to the lability of many therapeutic agents even under moderately acidic or basic conditions. Enzymes can promote the hydrolysis without destroying the substrate or the product. Enzymes suitable for this reaction can be esterases, or lipases and can be in their natural, water soluble forms or immobilized by cross coupling, or attachment to commercially available solid support materials. Of the soluble enzymes evaluated, *Candida Antarctica* "B" lipase (Altus Biologics) is especially useful. An example of an enzyme immobilized by cross coupling is ChiroCLEC-PC™ (Altus Biologics). *Candida Antarctica* "B" lipase (Altus Biologics) can be immobilized by reaction with NHS activated Sepharose™ 4 Fast Flow (American Pharmacia Biotech). The pH of the reaction mixture during the hydrolysis is carefully controlled and maintained by a pH-stat between 5.5 and 7.5, advantageously between 5.7 and 6.5, via controlled addition of $NaHCO_3$ solution. When the reaction is completed the product is isolated by lyophilization of the filtered reaction mixture. The immobilized enzymes remain on the filter cake and can be reused if desired.

General Allyl or Alkyl Ester Method

Figure 8:
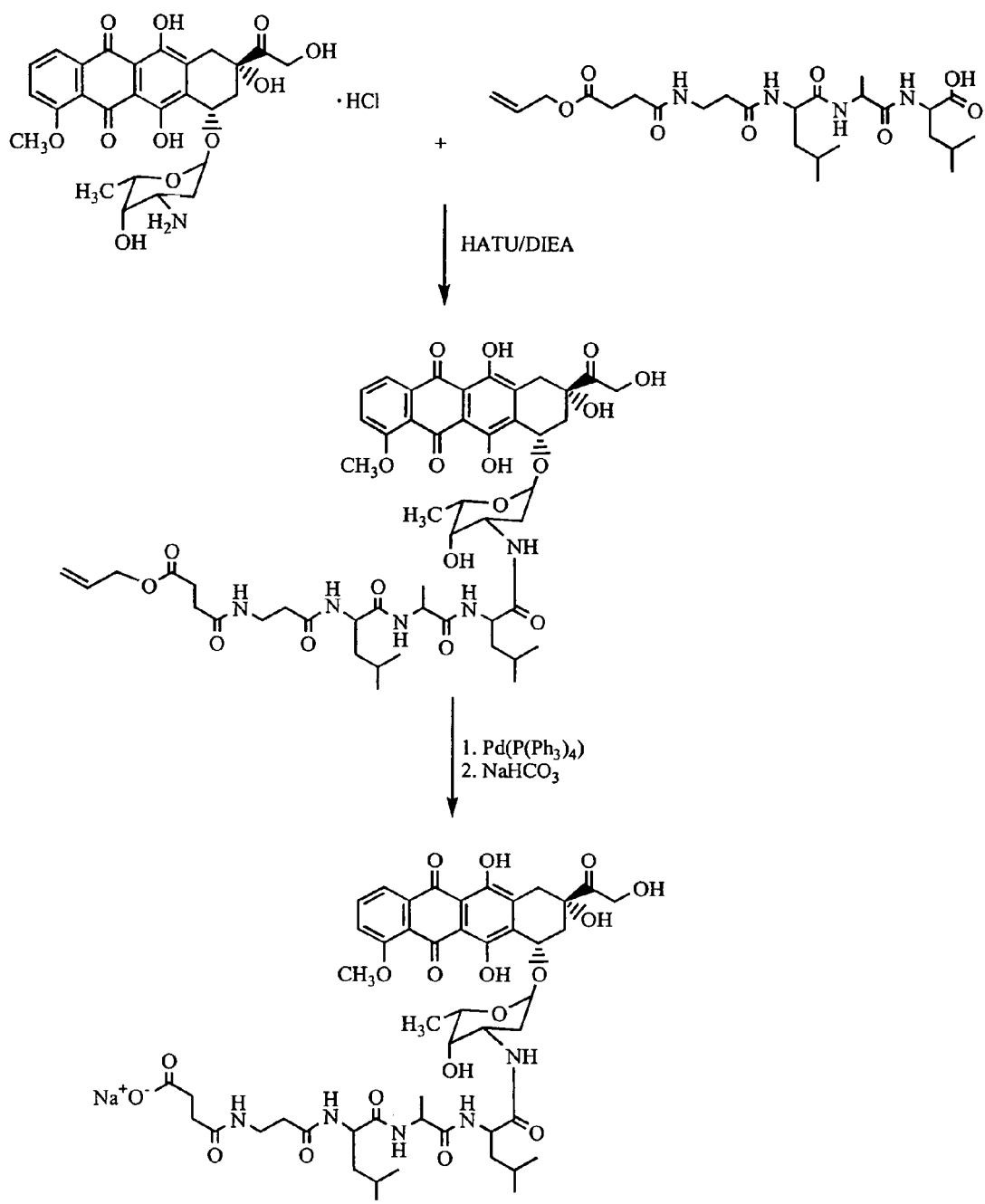
FIG. 8 illustrates an "Allyl ester route" synthesis of a salt form of Suc-βAla-Leu-Ala-Leu-DOX, a typical compound of the invention.

The prodrug can also be prepared via coupling an allyl-hemiester or alkyl-hemiester form of the N-cap oligopeptide with a therapeutic agent and then liberating the free acid from the conjugate. FIG. 8 illustrates this process with Succinyl-β-Ala-Leu-Ala-Leu and doxorubicin.

The coupling of allyl-succinyl-β-Ala-Leu-Ala-Leu with doxorubicin can be carried out via any one of the oligopeptide conjugation methods.

Allyl-succinyl-βAla-Leu-Ala-Leu-doxorubicin can also be synthesized by reacting allyl hemisuccinate, which was prepared via known methods (Casimir, et. al., *Tet. Lett.* 36:3409 (1995)), with βAla-Leu-Ala-Leu-doxorubicin similarly as coupling of the protected tetrapeptide precursors to doxorubicin was described in the previous methods, shown in FIG. 5. Suitable inert solvents are THF, dichloromethane, ethyl acetate, toluene, preferably THF from which the acid form of the product precipitates as the reaction progresses. The isolated acid is converted to its sodium salt as described earlier. Reaction times vary between 10-180 minutes, advantageously 10-60 minutes, at temperatures between 0-60° C., preferably 15-30° C.

Removal of the allyl or alkyl group can be done with Pd (0), or Ni(0), advantageously Pd(0) promoted transfer of the allyl or alkyl group to acceptor molecules, as it is well known in the art and documented in the professional literature (Genet, et al., *Tet. Lett.* 50:497 (1994); Bricout, et al. *Tet. Lett.* 54:1073 (1998), Genet, et al. *Synlett* 680 (1993); Waldmann, et al., *Bioorg. Med. Chem.* 7:749 (1998); Shaphiro, et al., *Tet. Lett.* 35:5421 (1994)). The amount of catalyst can be 0.5-25% mol to the substrate.

General Trityl or Substituted Trityl Method

Figure 7:
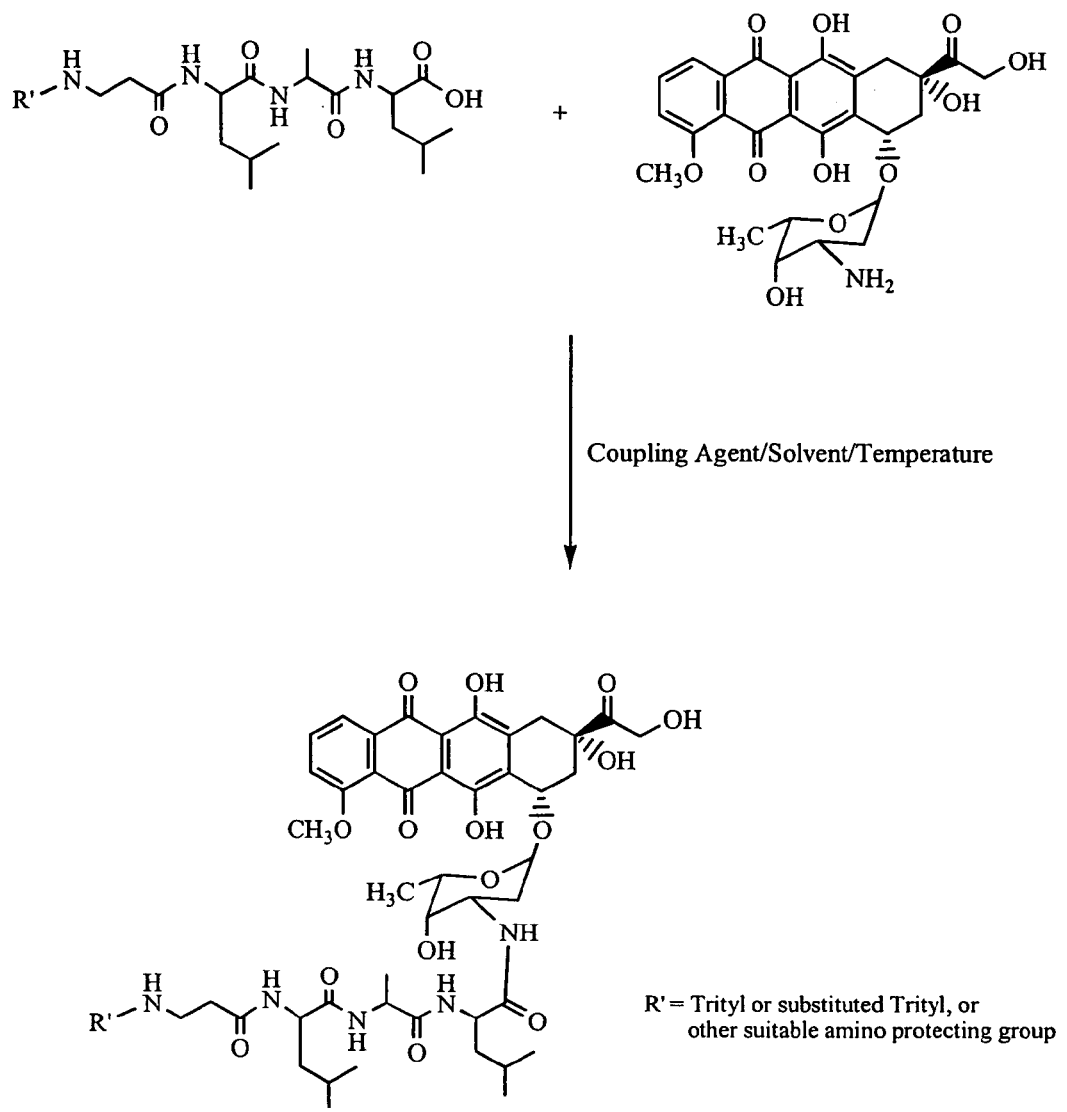
FIG. 7 illustrates a synthesis of an amino-protected βAla-Leu-Ala-Leu-DOX, a typical intermediate of the invention.

The prodrug may also be synthesized via the method shown in FIG. 7. This approach utilizes an R'-oligopeptide, where R' is trityl or substituted trityl. The coupling of R'-oligopeptide with a therapeutic agent can be carried out via any one of the methods described earlier for conjugation of a protected oligopeptide with a therapeutic agent at 30-120 minutes at 0-20° C.

Removal of trityl or substituted trityl group can be achieved under acidic conditions to give the positively charged prodrug. This positively charged prodrug is N-capped as illustrated in FIG. 4 and described earlier. The trityl deprotection can be accomplished with acetic acid, formic acid and dilute hydrochloric acid.

The prodrug can be converted into succinyl or glutaryl βAla-Leu-Ala-Leu therapeutic agent by reacting with succinic anhydride. Succinyl or glutaryl βAla-Leu-Ala-Leu therapeutic agent can be converted to any pharmaceutically acceptable salt. The solvent for coupling step DMF, DMSO, $CH_3CN$, NMP, or any other suitable solvent is known in the art.

General Inverse Direction Solid Phase Conjugation Method

The prodrug compound of the present invention can be synthesized by using solid phase chemistry via "step wise" inverse (from the N-terminal to the C-terminal) direction methods.

Figure 9:
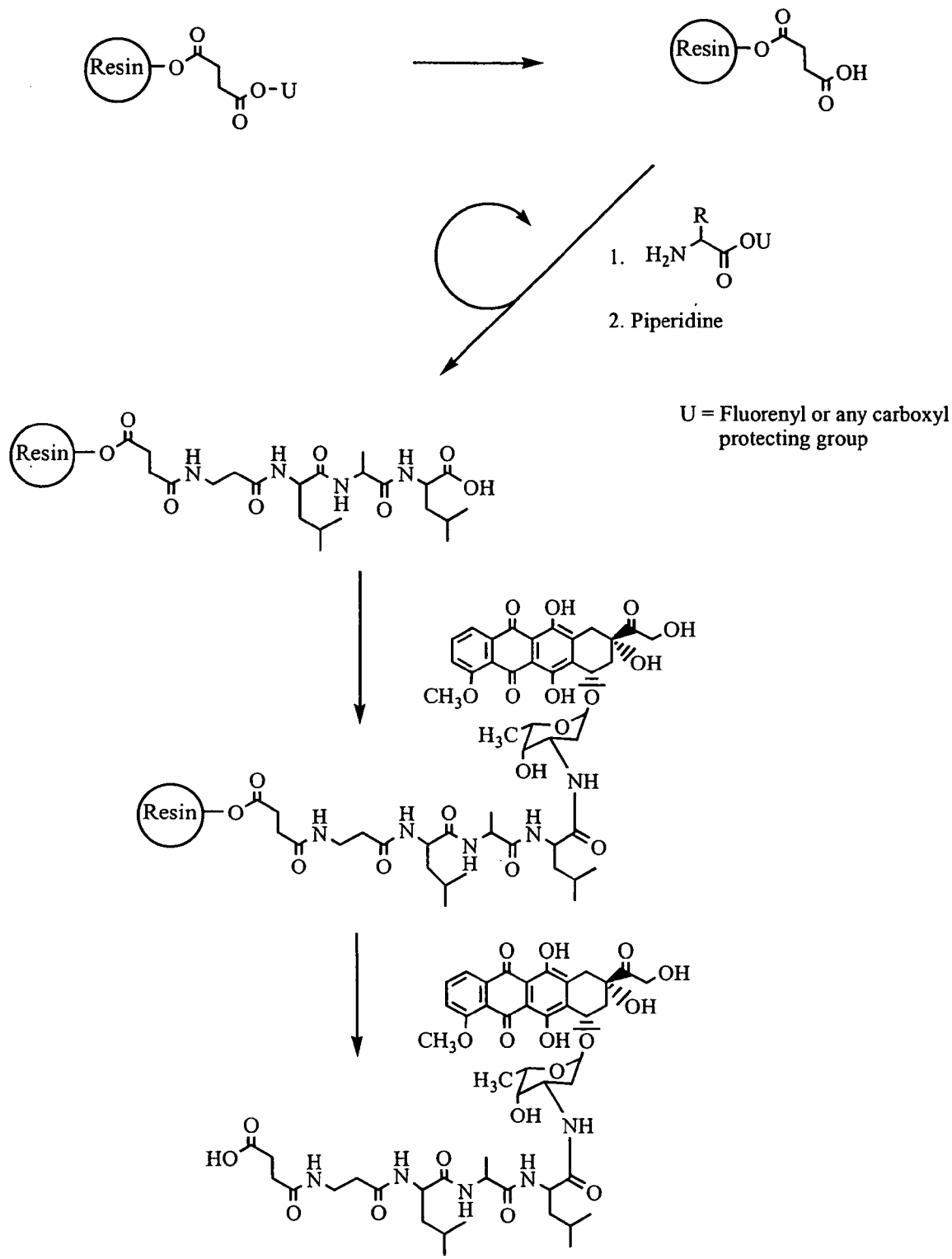
FIG. 9 illustrates a "Resin route" synthesis of Suc-βAla-Leu-Ala-Leu-DOX, a typical compound of the invention.

One way is to use resins to immobilize a succinyl-hemi ester, for example succinyl-mono-benzyl ester or -allyl ester. Examples of resins could be selected are "Wang Resins" (Wang, *J. Am. Chem. Soc.* 95:1328 (1973); Zhang, et al. *Tet. Lett.* 37:5457 (1996)), "Rink Resins" (Rink, *Tet. Lett.* 28:3787 (1987)), "Trityl-, or substituted-trityl Resins" (Chen, et. al., *J. Am. Chem. Soc.* 116:2661 (1994); Bartos, et. al., *Peptides, Proc.* $22^{nd}$ *European Peptide Symposium* (1992); Schneider and Eberle (Eds.), *ESCOM, Leiden*, pp. 281 (1993). The immobilized ester is then deprotected and reacted with, for example, a similarly C-terminal protected β-alanine. These steps are then repeated with leucine, alanine, and finally leucine esters, followed by the coupling of doxorubicin to the immobilized succinyl-tetrapeptide. The molecule is then liberated from the resin by using mildly acidic conditions to form a free prodrug, such as free Suc-βAla-Leu-Ala-Leu-Dox. This methodology is represented on the scheme of FIG. 9. Another version of phase synthesis utilizes immobilized succinyl oligopeptide. This is then C-terminally deprotected, followed by the coupling step to doxorubicin or other therapeutic agent, and finally liberated from the resin as represented on the scheme of FIG. 9. The acid form of the prodrug molecule may then be converted finally into its sodium salt as described above.

General Large Scale Compound Synthesis

Figure 16:
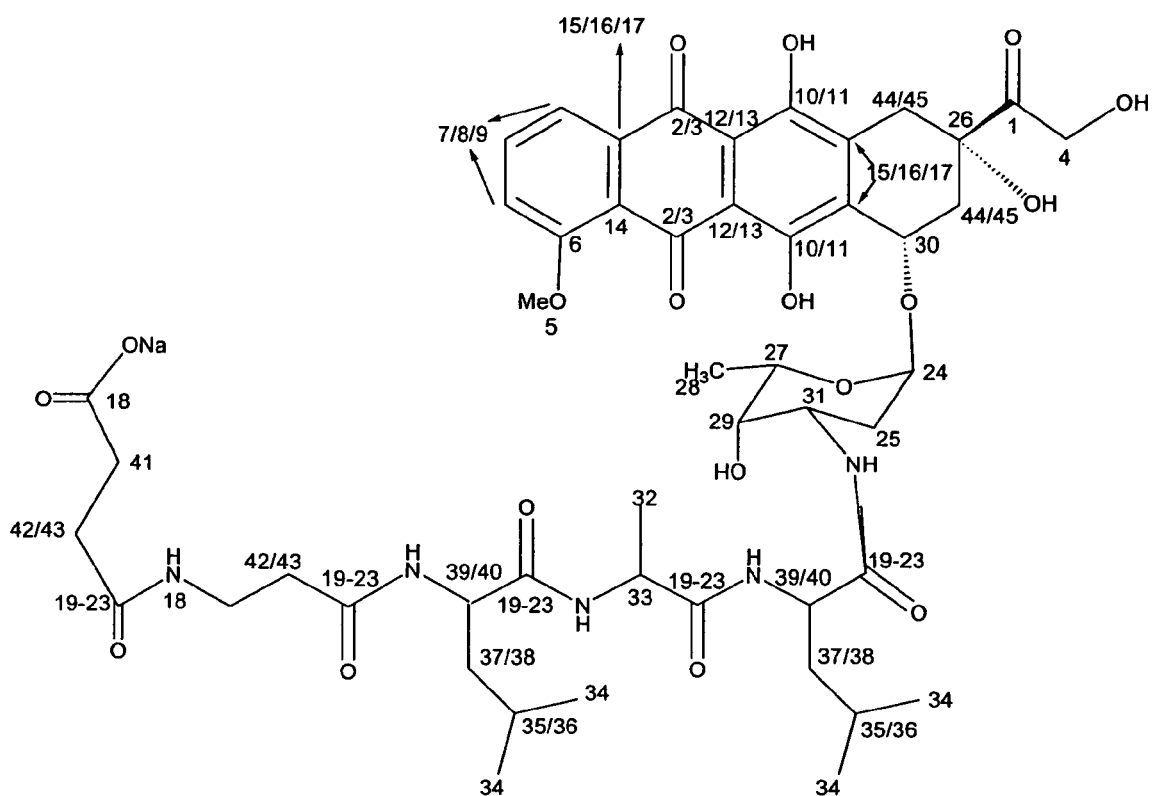
FIG. 16 illustrates a large scale synthesis of MeOSuc-βAla-Leu-Ala-Leu-Dox, a typical intermediate of the invention.

The prodrug compound can be synthesized using a simple and efficient three-step process of the invention. The first step involves the coupling of an alkyl-ester protected oligopeptide fragment to a therapeutic agent. A preferred embodiment of the first step involves the coupling of MeOSuc-βAla-Leu-Ala-Leu-OH with doxorubicin (FIG. 16) using HATU as a coupling agent to give MeOSuc-βAla-Leu-Ala-Leu-Dox. The focus of this step is on the purity and the yield of the methyl ester, since it was found that the hydrolysis step did not have an impact on purity.

The second step is the hydrolysis of the alkyl-ester group by an enzyme (esterase), which directly gives the prodrug compound in good yield with a final purity of at least 90%. For example, the second step may be the hydrolysis of the methyl ester group in MeOSuc-βAla-Leu-Ala-Leu-Dox by an enzyme (CLEC CAB, crosslinked *Candida Antarctica* "B" Lipase), which directly gives the sodium salt of Suc-βAla-Leu-Ala-Leu-Dox in quantitative yields with high purity.

The final step is to isolate the product after the hydrolysis step. Since most therapeutic agents are toxic substances, it is preferable to add an extra step to eliminate any free therapeutic agent from the coupled product. The focus of final step is to isolate the final product. For example, Suc-βAla-Leu-Ala-Leu-Dox, after the hydrolysis step. This is simply achieved by filtering the reaction mixture from the hydrolysis step using 0.2 micron filter and then lyophilizing the filtrate to yield Suc-βAla-Leu-Ala-Leu-Dox.Na.

Removal of Free Therapeutic Agent

Figure 14:
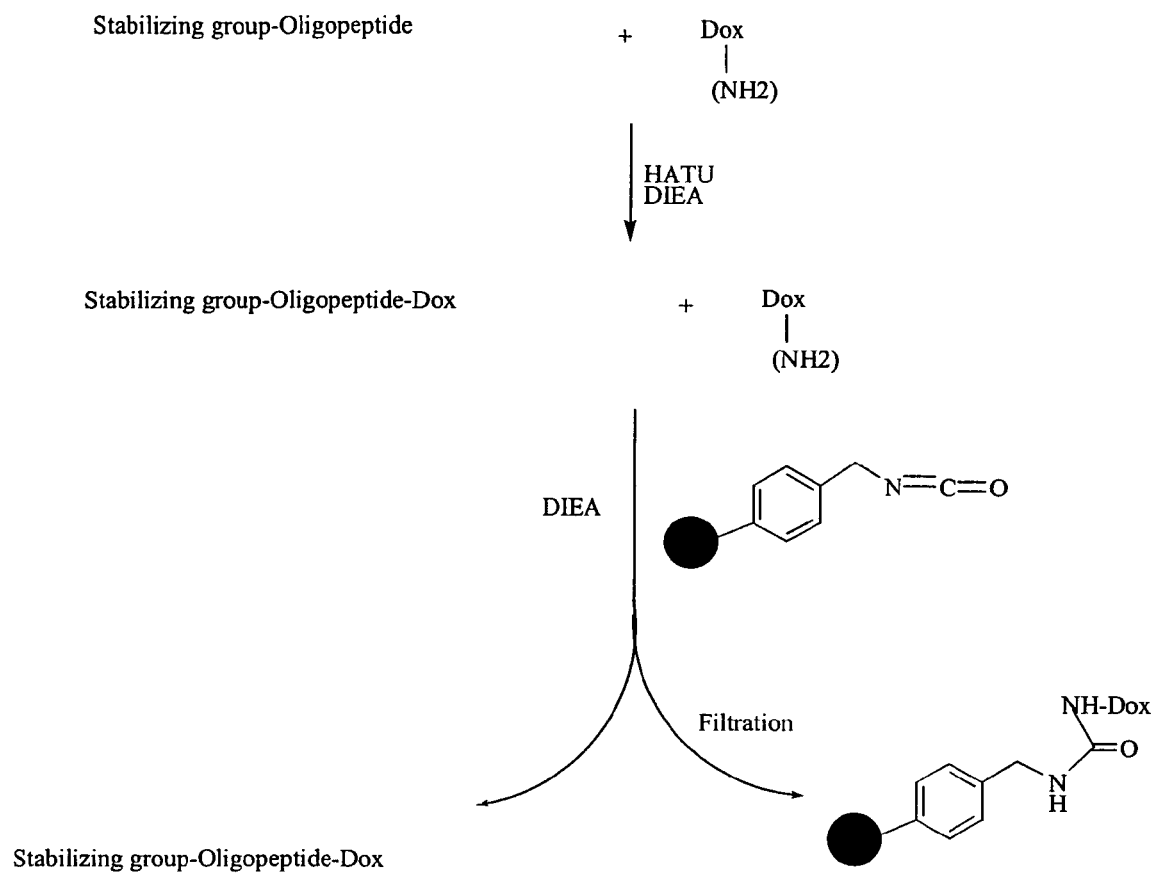
FIG. 14 illustrates the removal of free therapeutic agent through the use of scavenging resin or beads.

Unconjugated therapeutic agent may be present late in the process of making the prodrug. For example, during the coupling step of the (stabilizing group)-(oligopeptide) conjugate with doxorubicin as the therapeutic agent, it was found, in some instances, that the reaction did not proceed completely. There was about 2-4% of residual doxorubicin remaining in the coupled product. Initial attempts to remove doxorubicin completely from the product by acidic washes did not result in complete removal. For the large scale synthesis of MeOSuc- βAla-Leu-Ala-Leu-Dox, the complete removal of doxorubicin is crucial. The complete removal of the free therapeutic agent was effected by the process outlined in Example 41 and FIG. 14 that utilizes scavenging resin or beads.

The crude product which contains MeOSuc-β-Ala-Leu-Ala-Leu-Dox and residual doxorubicin were dissolved in DMF and polystyrene methylisocyanate or polystyrene sulfonyl chloride resin or beads were added. The reaction was stirred for 60 minutes. The free amino group of doxorubicin reacts with the isocyanate or sulfonyl chloride group on the beads to form a urea or sulfonamide derivative. The solid beads with doxorubicin attached to them were then separated from the desired product by filtration. The desired product remains in the DMF solution. This approach seems to be a very mild and effective method for removing residual therapeutic agent from the product.

Thus, the invention includes a method of making a compound comprising:

(1) selecting an Fmoc-protected oligopeptide of the formula

Fmoc-$(AA)_n$-$AA^4$-$AA^3$-$AA^2$-$AA^1$, wherein:

each AA independently represents an amino acid, n is an integer from 0 to 16, $AA^4$ represents a non-genetically-encoded amino acid, $AA^3$ represents any amino acid, $AA^2$ represents any amino acid, and $AA^1$ represents any amino acid, (2) coupling the Fmoc-protected oligopeptide to a therapeutic agent by activating the Fmoc-protected oligopeptide with an activating agent in the presence of the therapeutic agent to form an Fmoc-protected oligopeptide-therapeutic agent conjugate, (3) deprotecting the Fmoc-protected oligopeptide-therapeutic agent conjugate by contacting it with a base to form an oligopeptide-therapeutic agent conjugate, and (4) coupling the oligopeptide-therapeutic agent conjugate to a stabilizing group to form the compound.

Alternatively, a method of making a compound comprises the following steps:

(1) selecting an oligopeptide of the formula $(AA)_n$-$AA^4$-$AA^3$-$AA^2$-$AA^1$, wherein:

each AA independently represents an amino acid, n is an integer from 0 to 16, $AA^4$ represents a non-genetically-encoded amino acid, $AA^3$ represents any amino acid, $AA^2$ represents any amino acid, and $AA^1$ represents any amino acid, (2) coupling the oligopeptide to an alkyl ester-protected stabilizing group to form an alkyl ester-protected stabilizing group-oligopeptide conjugate, (3) coupling the alkyl ester-protected-stabilizing group-oligopeptide conjugate to a therapeutic agent by activating the alkyl ester-protected stabilizing group-oligopeptide conjugate with an activating agent in the presence of a therapeutic agent to form an alkyl ester-protected stabilizing group-oligopeptide-therapeutic agent conjugate, and (4) deprotecting the alkyl ester-protected stabilizing group-oligopeptide therapeutic agent conjugate to form the compound.

A compound of the invention may also be made via the following steps:

(1) selecting an oligopeptide of the formula $(AA)_n$-$AA^4$-$AA^3$-$AA^2$-$AA^1$, wherein each AA independently represents an amino acid, n is an integer from 0 to 16, $AA^4$ represents a non-genetically-encoded amino acid, $AA^3$ represents any amino acid, $AA^2$ represents any amino acid, and $AA^1$ represents any amino acid;

(2) coupling the oligopeptide to an allyl ester-protected stabilizing group to form an allyl ester-protected stabilizing group-oligopeptide conjugate, (3) coupling the allyl ester-protected-stabilizing group-oligopeptide conjugate to a therapeutic agent by activating the allyl ester-protected stabilizing group-oligopeptide conjugate with an activating agent in the presence of a therapeutic agent to form an allyl ester-protected stabilizing group-oligopeptide-therapeutic agent conjugate, and (4) deprotecting the allyl ester-protected stabilizing group-oligopeptide therapeutic agent conjugate to form the compound.

Yet another method for making a compound of the invention comprises the following steps:

(1) selecting a trityl-protected oligopeptide of the formula trityl-$(AA)_n$-$AA^4$-$AA^3$-$AA^2$-$AA^1$, wherein:

each AA independently represents an amino acid, n is an integer from 0 to 16, $AA^4$ represents a non-genetically-encoded amino acid, $AA^3$ represents any amino acid, $AA^2$ represents any amino acid, and $AA^1$ represents any amino acid, (2) coupling the trityl-protected oligopeptide to a therapeutic agent by activating the trityl-protected oligopeptide with an activating agent in the presence of a therapeutic agent, thereby making a trityl-protected oligopeptide-therapeutic agent conjugate, (3) deprotecting the trityl-protected oligopeptide-therapeutic agent conjugate under acidic conditions to form an oligopeptide-therapeutic agent conjugate, and (4) coupling the oligopeptide-therapeutic agent conjugate with an stabilizing group to form the compound.

Another possible step in connection with any of these methods is removing uncoupled therapeutic agent by use of scavenging resin or beads. Further, the compound may be neutralized with a pharmaceutically acceptable salt if desired.

Thus, in a method of making a prodrug, the invention includes a method of removing free therapeutic agent comprising:

(1) coupling an optionally protected stabilizing group-oligopeptide conjugate with the free therapeutic agent, (2) contacting the reactants of step (1) with a polymeric resin to bind free therapeutic agent remaining after step (1) and to form a therapeutic agent-polymeric resin complex, and (3) removing the therapeutic agent-polymeric resin complex.

The polymeric resin may be polystyrene methylisocyanate or polystyrene sulfonyl chloride.

Specific Compounds

Compounds of the invention include the prodrugs, Suc-βAla-Leu-Ala-Leu-Dox, Suc-βAla-Leu-Ala-Leu-Dnr, and Gl-βAla-Leu-Ala-Leu-Dox.

Additionally, the following intermediate compounds, important to the process of preparation of the prodrugs of the invention, are part of the invention:

βAla-Leu-Ala-Leu

Trityl-βAla-Leu-Ala-Leu-Dox

Diphenylmethyl-βAla-Leu-Ala-Leu-Dox

Benzyloxycarbonyl-βAla-Leu-Ala-Leu-Dox

Fmoc-βAla-Leu-Ala-Leu-OBn

βAla-Leu-Ala-Leu-OBn

Methyl-succinyl-βAla-Leu-Ala-Leu-OBn

Methyl-succinyl-βAla-Leu-Ala-Leu

Fmoc-βAla-Leu-Ala-Leu

Fmoc-Thi-Tyr-Gly-Leu

Fmoc-βAla-Leu-Ala-Leu-Dnr

Fmoc-Thi-Tyr-Gly-Leu-Dnr

Suc-Thi-Tyr-Gly-Leu-Dnr

Gl-βAla-Leu-Ala-Leu-Dox

βAla-Leu-Ala-Leu-Dox Lactate

Allyl-succinyl-βAla-Leu-Ala-Leu-Dox

Suc-βAla-Leu-Ala-Leu

Methyl esters of Suc-βAla-Leu-Ala-Leu

Fmoc-βAla-Leu-Ala-Leu-Dox

Methyl-succinyl-βAla-Leu-Ala-Leu-Dox, and

Allyl-hemi succinate.

EXAMPLES

Example 1

Preparation of MCF 7/6 Cell Homogenate

MCF 7/6 cells were grown to confluence in a serum free medium containing DMEM:F12 (1:1), 50 mg/L bovine serum albumin, ITS-X (10 mg/L insulin, 5.5 mg/L transferrin, 6.7 µg/L Na selenite, 2 mg/L ethanolamine), and Lipid Concentrate (Gibco #21900-030). 100 mL of cells were harvested by centrifugation at 4° C. 10,000×g, for 20 min and decanting the supernatant. The pellet was resuspended in 2 mL phosphate buffered saline (Gibco) and centrifuged at 18,000×g for 10 min. After decanting the supernatant, the cells (approximately 300 µL wet) were homogenized by grinding in 1.7 mL 10 mM pH 7.2 HEPES buffer (sodium salt). The homogenate was centrifuged at 18,000×g at 4° C. for 5 min and the supernatant was aliquoted and stored at ≦−20° C. for subsequent use in the compound screen.

Example 2

Preparation of MCF 7/6 Conditioned Media

MCF 7/6 cells were grown to confluence in DMEM/F12 (1:1) medium containing 10% fetal bovine serum, 0.05% (w/v) L-glutamine, 250 IU/mL penicillin, and 100 µg/mL streptomycin. Cells were then washed twice with phosphate buffered saline and incubated 24 hr at 5% $CO_2$, 37° C., in DMEM/F12 (1:1), 0.02% BSA, ITS-X (10 mg/L insulin, 5.5 mg/L transferrin, 6.7 µg/L Na selenite, 2 mg/L ethanolamine). The conditioned media was then decanted and, using a stirred cell apparatus with a YM10 (10,000 MW cutoff) ultrafiltration membrane (Millipore), exchanged once with 10 mM HEPES buffer, pH 7.2 and concentrated twenty-fold. This solution was stored in aliquots at −20° C. for use in the compound screen.

Example 3

Preparation of HeLa Cell Anion Exchange Fraction Pool (F1)

Thirty billion commercially produced HeLa Cells (human cervical carcinoma, Computer Cell Culture Center, Seneffe, Belgium) were homogenized with a sonicator and with a Dounce homogenizer in 108 mL of aqueous lysis solution. The lysis solution contained 0.02% w/v Triton X-100, 0.04% w/v sodium azide, and a cocktail of protease inhibitors (2 tablets/50 mL Complete™, EDTA-free tablets, Roche Molecular Biochemicals). The cell homogenate was centrifuged 30 minutes at 4° C. at 5000×g and the pellet was homogenized in a second 108 mL of lysis solution using a Dounce homogenizer and centrifuged as before. The supernatants were combined and centrifuged for 90 min at 145,000×g at 4° C.

A portion of the ultracentrifugation supernatant was diluted 2-fold with a 20 mM triethanolamine-HCl pH 7.2 buffer containing 0.01% (w/v) Triton X-100 and 0.02% (w/v) sodium azide (equilibration buffer). Thirty mL of the resulting solution, corresponding to approximately 180 mg of protein, was loaded at 4° C. on a 2.6×9.4 cm Source™ 15 Q (Amersham Pharmacia Biotech) low pressure anion exchange chromatography column (1 ml/minute). The column was then washed with 250 ml of the equilibration buffer at a flow rate of 1 mL/minute. Proteins were eluted in a NaCl linear concentration gradient (0-0.5 M in the equilibration buffer, total volume of the gradient was 1000 ml) at a flow rate of 3 ml/minute. Two-minute fractions were collected and used for enzyme activity determination using βAla-Leu-Ala-Leu-Dox as the substrate. Its transformation into Ala-Leu-Dox was quantified by reverse phase high performance liquid chromatography utilizing fluorescence detection of the anthracycline moiety. The fractions containing the highest activity levels were pooled (fractions #43-46; ~0.13 M NaCl), supplemented with protease inhibitors (Complete™, EDTA-free tablets, Roche Molecular Biochemicals), and stored as aliquots at −80° C.

Example 4

Purification of HeLa Cell Trouase

HeLa cell fraction 1 (F1) was prepared from 50 billion HeLa cells as described in the Example 3 except that 6 runs with a load of about 350 mg of proteins each were performed and 50 µM $CoCl_2$ was added to the equilibration and elution buffers. The F1 fraction was concentrated by ultrafiltration (30 KD MWCO) and incubated in the presence of 1.25% EDTA for 2 hours at 4° C. EDTA was removed on a desalting column (PD10) equilibrated and eluted with equilibration buffer (20 mM phosphate, 0.01% Triton-X100, 0.02% $NaN_3$, 0.5 M NaCl, pH 7.2). About twenty mg of protein corresponding to the F1 fraction were then loaded onto a 12×150 mm Chelating-Sepharose (Amersham Pharmacia Biotech) column previously treated successively with 250 mL 5% EDTA, 250 ml water, 250 mL 0.1 M CoCl$_2$, 250 mL water and 250 mL of the equilibration buffer. After sample adsorption, the column was washed with 150 mL of the equilibration buffer and eluted with a 600 mL 0-0.2 M imidazole gradient. All steps were carried out with a flow rate of 0.1 ml/min. Forty-minute fractions were collected. The activity-containing fractions (~1 mg of protein) were pooled, concentrated by ultrafiltration and diluted (1:1) with electrophoresis sample buffer (0.12 M Tris-HCl, 5% glycerol, 0.01% bromophenol blue, pH 6.8). This sample was fractionated by preparative native polyacrylamide gel electrophoresis. A Model 491 PrepCell (Bio-Rad) was used with a 37×120 mm, 7% T, 2.6% C resolving gel buffered with 0.37 M Tris-HCl, pH 8.8, and a 37×5 mm, 4% T, 2.6% C concentrating gel buffered with 0.12 M Tris-HCl, pH 6.8. The electrode buffer was 25 mM Tris, 192 mM glycine, pH 8.3, and the elution buffer 100 mM triethanolamine, 0.01% Triton X-100, 50 μM CoCl$_2$, pH 7.2. After 30 minutes at 30 mA, separation was performed for about 24 hours at 40 mA. Twelve-minute fractions were collected with an elution flow rate of 0.4 ml/min. Activity containing fractions (~150 μg of protein) were pooled, concentrated by ultrafiltration and the sample was applied to a gel filtration HPLC column (TosoHaas TSK G3000SW$_{XL}$, 7.8×600 mm) equilibrated and eluted at 0.3 mL/min with 50 mM, pH 7.0 phosphate buffer containing 0.2M K$_2$SO$_4$. Fractions of 0.5 min were collected. The activity-containing fractions were stored at −80° C.

Example 5

Screening of Potential Prodrugs with Trouase and Human Blood

Based on HPLC analysis of digestion products, activation of prodrug to free toxin occurs via a series of enzyme catalyzed cleavage reactions. For example, the prodrug, Suc-βAla-Leu-Ala-Leu-Dox is converted to Leu-Dox in extracts of carcinoma cells or carcinoma cell conditioned media in two steps catalyzed by at least two enzymes. Initial endopeptidase cleavage occurs between the AA$^3$ (P1) and AA$^2$ (P1') amino acids to yield Ala-Leu-Dox. Subsequently, exopeptidase removes alanine to give leucyl-doxorubicin which is known to be taken up into cells where the active toxin, doxorubicin, is released.

A good candidate for a prodrug with improved therapeutic index is activated by cancer cells but relatively stable in whole human blood. Three different preparations of carcinoma were used to screen various N-capped peptidyl-toxins. These three preparations were as follows:

(a) MCF 7/6 (breast carcinoma) cell homogenate
(b) MCF 7/6 (breast carcinoma) conditioned media, and
(c) HeLa (cervical carcinoma) cell extract anion exchange fraction pool.

Compounds which could be hydrolyzed to a single amino acid toxin conjugate (i.e., AA$^1$-(optional linker)-therapeutic agent) were further tested for stability in whole human blood. The whole blood was collected using commercial acid buffered citrate whole blood collection tubes (Becton Dickinson).

Test compounds were incubated for 2 hr at 37° C. at a concentration of 12.5 μg/mL with the three different preparations of carcinoma enzyme and with whole blood. Following incubation, three volumes of acetonitrile were added to stop the reaction and remove protein from the mixture. The sample was centrifuged at 18,000 g for 5 minutes and 100 μL of supernatant was mixed with 300 μL of water prior to analysis by HPLC.

For HPLC analysis 50 μL of sample was injected on a 4.6×50 mm 2 TSK Super-ODS chromatography column at 40° C. and eluted with a 3 minute linear gradient from 26% to 68% acetonitrile in aqueous 20 mM ammonium formate pH 4.5 buffer at 2 mL/min. Detection was by fluorescence using an excitation wavelength of 235 nm and an emission wavelength of 560 nm.

The oligopeptide portions of test compounds that were cleaved by the trouase under the given conditions and were stable in human blood are shown in FIGS. 10A-10C. For all oligopeptides shown in FIGS. 10A-10C, the test compounds had a Succinyl stabilizing group and a Daunorubicin therapeutic agent. Additionally, the oligopeptide having SEQ ID NO: 1 was tested with Aminomethylbenzoic acid as a stabilizing group and Daunorubicin as the therapeutic agent. The oligopeptide having SEQ ID NO: 35 was also tested with Diglycolic acid and Malic acid as stabilizing groups and Daunorubicin as the therapeutic agent. The oligopeptide having SEQ ID NO: 38 was also tested with a number of additional stabilizing groups and therapeutic agents. Particularly, test compounds of the oligopeptide of SEQ ID NO: 38 included 1-Admantenecarbonyl-βAla-Leu-Ala-Leu-Dnr, Diphenyl-Acetyl-βAla-Leu-Ala-Leu-Dnr, Maleic-βAla-Leu-Ala-Leu-Dox, 4-Morpholinecarbonyl-βAla-Leu-Ala-Leu-Dnr, PEG-βAla-Leu-Ala-Leu-Dox, 2-Furoyl-βAla-Leu-Ala-Leu-Dnr, Acetyl-βAla-Leu-Ala-Leu-Dnr, Diglycolic-βAla-Leu-Ala-Leu-Dox, and Napth-βAla-Leu-Ala-Leu-Dox.

With few exceptions, results for carcinoma enzyme cleavage were the same for a partially purified fraction from HeLa cells, MFC 7/6 cell homogenate, or MCF 7/6 conditioned media.

Example 6

Rates of Hydrolysis

For comparison of rates of hydrolysis for different prodrugs or measurement of trouase and TOP activity after immunoprecipitation, enzyme test solution (as prepared in Examples 1-4 above) was incubated with 10 μg/mL substrate in pH 7.2 10 mM HEPES with 100 μM MnCl$_2$ at 37° C. for up to 2 hr. The reaction was stopped by adding three volumes of acetonitrile. Precipitated protein was removed by centrifugation and the supernatant was diluted into three volumes of water before HPLC analysis, as described in Example 5 above. The fraction of substrate hydrolyzed was calculated by dividing peak areas for products by total peak area for substrate and products.

Substrate specificity of partially purified HeLa cell trouase was essentially identical to that of recombinant rat TOP (rRTOP) produced in *E. coli* according to the method of Glucksman and Roberts. (Glucksman and Roberts, "Strategies for characterizing, cloning, and expressing soluble endopeptidases," *Methods in Neurosciences*, 23: 296-316 (1995)) Nine peptidyl test compounds were found to have similar rates of hydrolysis with HeLa cell F1 and rR-TOP (Table 1). For all of the peptidyl Dox substrates, the Dox linked reaction product was AA$^2$-AA$^1$-Dox. For example Suc-βAla-Leu-Ala-Leu-Dox was cleaved to Ala-Leu-Dox and presumably Suc-βAla-Leu.

TABLE 1

| Substrate | (F1) | TOP |
| --- | --- | --- |
| Suc-βAla-Leu-Ala-Leu-Dox | 1.0 | 1.0 |
| Suc-βAla-Ile-Ala-Leu-Dox | 0.025 | <0.03 |
| Suc-Leu-Ala-Leu-Dox | 0.78 | 0.67 |
| Suc-Met-Ala-Leu-Dox | 0.49 | 0.99 |
| Suc-Ile-Ala-Leu-Dox | 0 | 0 |
| Suc-Leu-Ala-Gly-Dox | 0.4 | 0.43 |
| Suc-Leu-NmAla-Leu-Dox | 0 | 0 |
| Suc-Ile-NmAla-Leu-Dox | 0 | 0 |
| Mcc-Pro-Leu-Gly-Pro-D-Lys(DNP) | 1.5 | 1.1 |

Nm = N-methyl
Mcc = 7-Methoxycoumarin-3-carboxyl
DNP—dinitrophenyl

Thus, carcinoma cell trouase and TOP have nearly identical substrate specificity.

Example 7

Hydrolysis by Purified CD10

Equal amounts of purified Porcine Kidney CD10 (Elastin Products Company) were incubated with 12.5 µg/mL of various peptidyl doxorubicin compounds for up to 10 hr at 37° C. in pH 7.4 50 mM Tris HCl, 150 mM NaCl, 0.1% Triton X-100. Reaction products were analyzed by HPLC with fluorescence detection. Rates were essentially linear over the incubation period. The observed product was Leu-doxorubicin. Table 1 provides the percent of each test compound that was hydrolyzed over the ten hour period. Further these results are expressed relative to a standard test compound, Suc-Ala-Leu-Ala-Leu-Dox.

TABLE 2

Hydrolysis by CD10

| Substrate | % hydrolysis/10 hr | Fraction hydrolyzed relative to standard |
| --- | --- | --- |
| Suc-βAla-Leu-Ala-Leu-Dox | 10.9 | 1.0 |
| Suc-βAla-Leu-Tyr-Leu-Dox | 0 | 0 |

Example 8

Inhibition and Inactivation of Top and HeLa Cell Trouase

As expected for a metalloenzyme, TOP is inactivated by exposure to metal chelating agents such as EDTA and 1,10 phenanthroline (Barrett, et al., "Thimet oligopeptidase and oligopeptidase M or neurolysin," *Methods Enzymol* 248: 529-556 (1995)). The peptide compound N-[1-(RS)-carboxypropyl-Ala-Ala-Phe-p-aminobenzoate (Cpp-AAF-pAB)] is a more selective and sensitive inhibitor (Knight and Barrett, "Structure/function relationships in the inhibition of thimet oligopeptidase by carboxyphenylpropyl-peptides," *FEBS Lett* 294: 183-186 (1991)). Although Cpp-AAF-pAB also inhibits the closely related metallopeptidase neurolysin, only neurolysin activity is inhibited by 5 mM of the dipeptide Pro-Ile (Serizawa, et al., "Characterization of a mitochondrial metallopeptidase reveals neurolysin as a homologue of thimet oligopeptidase," *J Biol Chem* 270:2092-2098 (1995)). In a study with MCF-7/6 cell homogenate trouase activity was inhibited 9-fold by 1 mM EDTA and 2 mM 1,10 phenanthroline while inhibitors of non-metallopeptidases were not effective. Thus, activity was not inhibited by 50 µM aminoethylbenzenesulfonylfluoride, 4 µg/mL aprotinin (both inhibit serine peptidase), 20 µM E-64 (inhibits cysteine peptidase), 1.5 µM pepstatin (inhibits aspartate peptidase), 20 µM leupeptin (inhibits serine and cysteine peptidase), or 1 µM CA-074 (inhibits cathepsin B). In tests with HeLa cell Fraction 1, 3 µM Cpp-AAF-pAB completely inhibited Suc-βAla-Leu-Ala-Leu-Dox hydrolysis while 5 mM Pro-Ile had no effect.

Barrett and Brown ("Chicken liver Pz-peptidase, a thiol-dependent metallo-endopeptidase," *Biochem J*, 271:701-706 (1990)) used purified chicken TOP to measure reactivation after dialysis against EDTA. At 50 µM concentration, $Zn^{2+}$ completely restored activity. Other divalent cations at the same concentration partially restored activity in the following order of effectiveness: $Mn^{2+}>Ca^{2+}>Co^{2+}>Cd^{2+}$. Other divalent cations such as $Cu^{2+}$ had no effect. An excess of $Zn^{2+}$ ($\geqq 100$ µM) was inhibitory. In reconstitution experiments with EDTA treated MCF-7/6 cell homogenate, activity was completely restored with 50 µM $Co^{2+}$ or $Mn^{2+}$, but not $Zn^{2+}$ or $Cu^{2+}$.

Example 9

Gel Filtration and Isoelectric Focusing

MCF-7/6 cell homogenate trouase had an approximate molecular weight of 68 KD based on the retention volume of active gel filtration chromatographic fractions. For these measurements, the MCF-7/6 cell homogenate and protein molecular weight standards were fractionated on a Superose S12, 10×300 column (Amersham-Pharmacia Biotech). Purified trouase from HeLa cells was separated by SDS polyacrylamide gel electrophoresis (PAGE) into two protein bands corresponding to 74 and 63 KD using methods described in example 11. Bands of about 74 and 63 KD were also observed in SDS PAGE western immunoblots of HeLa cell F1 stained with anti-thimet oligopeptidase antibody. The 74 KD band was also observed in SDS PAGE western blots of crude homogenates of MCF-7/6, MDS-MD-231, and EA hy926 cells. These results agree with the molecular weight of human, rat and porcine TOP which has been deduced from the DNA sequence as 78 KD and reported between 74-80 KD in various SDS PAGE determinations (Barrett, et al., "Thimet oligopeptidase and oligopeptidase M or neurolysin," *Methods Enzymol* 248: 529-556 (1995)).

An isoelectric point (pI) of 5.2 was determined for MCF-7/6 cell homogenate trouase by chromatofocusing on a Mono P HR 5/5, 5×40 mm column (Amersham-Pharmacia Biotech). This result agrees with pI value of 5.0±0.2 generally reported for TOP from various sources (Tisljar, "Thimet oligopeptidase—a review of a thiol dependent metallo-endopeptidase also known as Pz-peptidase endopeptidase 24.15 and endo-oligopeptidase," *Biol Chem Hoppe Seyler* 374: 91-100 (1993)).

Example 10

Thiol Activation

MCF-7/6 conditioned medium was pre-incubated for 30 minutes at room temperature with dithiothreitol (DTT) at indicated concentrations. Then 10 µg/mL Suc-βAla-Leu-Ala-Leu-Dox was added and incubated at 37° C. Hydrolysis products were extracted and analyzed on a Luna C18-3µ, 4.6×100 mm column (Phenomenex) as above. Residual Suc-βAla-Leu-Ala-Leu-Dox substrate was extracted using pH 3.0 citrate buffer rather than borate and N-succinyl doxorubicin as internal standard and analyzed on the Luna C18-3µ column as above.

Figure 13:
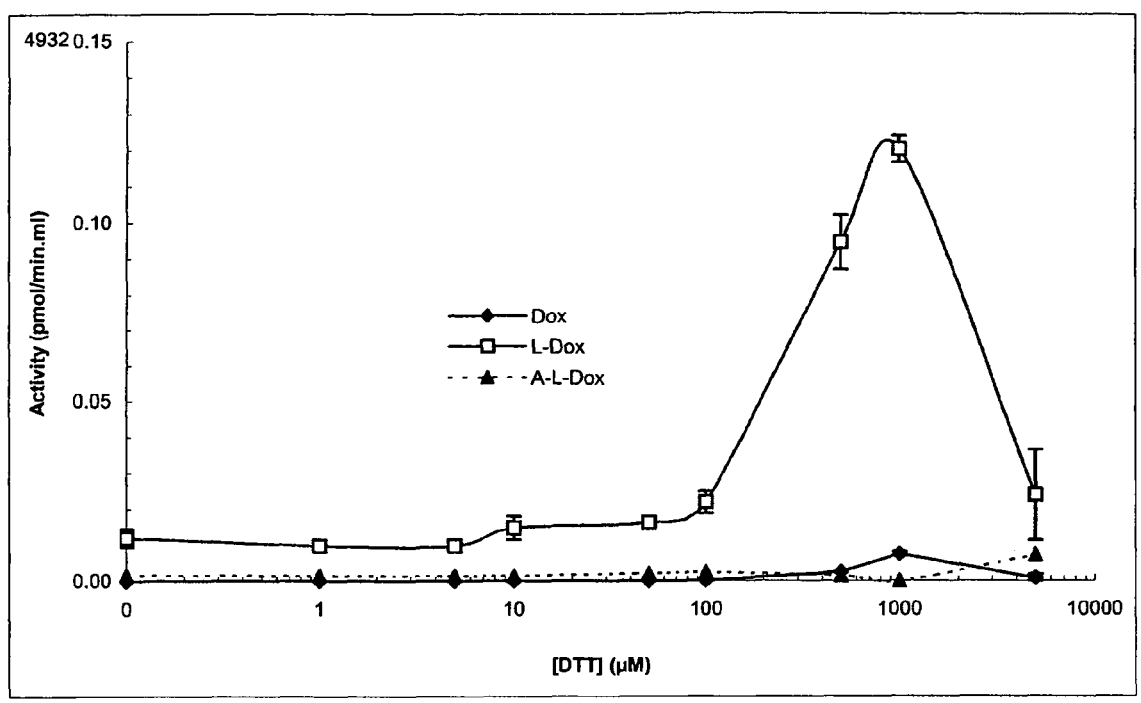
FIG. 13 is a graph of the activation and then inhibition of HeLa cell trouase by increasing concentrations of DTT.

Unlike most metallopeptidases, TOP is activated by low levels of thiol reducing agents such as 50 µM dithiothreitol (DTT) or 1 mM mercaptoethanol but inhibited at high concentrations such as 5 mM DTT (Orlowski, et al. "Endopeptidase 24.15 from rat testes. Isolation of the enzyme and its specificity toward synthetic and natural peptides, including enkephalin-containing peptides," Biochem J 261: 951-958 (1989); Tisljar and Barrett "Thiol-dependent metallo-endopeptidase characteristics of Pz-peptidase in rat and rabbit," Biochem J 267: 531-533 (1990); Lew, et al. "Substrate specificity differences between recombinant rat testes endopeptidase EC 3.4.24.15 and the native brain enzyme," Biochem Biophys Res Commun 209: 788-795 (1995)). Shrimpton, et al. "Thiol activation of endopeptidase EC 3.4.24.15. A novel mechanism for the regulation of catalytic activity," J Biol Chem 272: 17395-17399 (1997)) showed that the reducing agent activates by reversing formation of inactive disulfide linked dimers of the TOP enzyme protein. Similarly, DTT pretreatment experiments with MCF-7/6 cell conditioned media indicated tenfold activation of Suc-βAla-Leu-Ala-Leu-Dox hydrolysis at 1 mM DTT with inhibition at higher levels (FIG. 13). Thus both TOP and carcinoma cell trouase are activated by low levels of thiol reducing agents.

Example 11 pH Optimum

MFC-7/6 cell homogenate, as prepared in Example 1 above, was incubated with β-Ala-Leu-Ala-Leu-Cou at 37° C. in 100 mM triethanolamine buffered at various pH levels. The amount of Leu-Cou was determined by treatment of the reaction product with leucine aminopeptidase and measurement of the resulting aminomethylcoumarin concentration in a spectrofluorometer. TOP has a pH optimum of 7.8 for 10 minute assays with quenched fluorescent substrates (Barrett, 1995). Assay with the quenched fluorescent substrate Mcc-Pro-Leu-Gly-Pro-D-Lys(DNP) was as described in Barrett, et al. ("Thimet oligopeptidase and oligopeptidase M or neurolysin," Methods Enzymol 248: 529-556 (1995)). The MCF-7/6 cell homogenate trouase activity pH optimum was 7.2-7.7 for MCF-7/6 cell homogenate activity using the βAla-Leu-Ala-Leu-Cou assay. Thus, TOP and trouase activities are optimized at a similar pH.

Example 12

Mass Spectroscopy of Purified HeLa Cell Trouase Tryptic Digest

Purified HeLa trouase was lyophilized overnight, dissolved in 30 µL sample loading buffer at 90° C. for 1 minute, centrifuged to remove insoluble material and separated by SDS polyacrylamide gel electrophoresis on a small format gel. Running conditions were 30 mA, 300V for 45 minutes. After staining with coomassie blue R250, two bands, corresponding in molecular weight to 74 and 63 KD, were evident. A 2×2 mm piece of each band was transferred into small tubes and washed in 15 min steps with agitation with each of the following solutions: 25 mM bicarbonate (ammonium), 50% acetonitrile in water, 25 mM bicarbonate (ammonium). The samples were then dried in a centrifugal concentrator (Speedvac) and incubated 3 h at 37° C. with 10 µL of 25 mM ammonium bicarbonate solution containing 0.5 µg trypsin. For Nanospray-MS, a portion of the trypsin digest was extracted with acetonitrile, dried in a centrifugal vacuum concentrator (Speedvac) and purified with a ZipTip™ $C_{18}$ microextraction device before analysis.

The trypsin digested protein from the 74 KD band was analyzed by MALDI-tof (Matrix assisted laser desorbtion ionization-time of flight) mass spectrometry. Mass spectra of the tryptic digests were acquired on a Biflex (Bruker) MALDI-tof mass spectrometer equipped with delayed extraction operated in the reflector mode. 0.4 µL of each digest (in 25 mM ammonium bicarboante) was deposited directly on the sample probe in a dry thin layer α-cyano-4-hydroxy-cinnamic acid (CCA) matrix mixed with nitrocellulose (4:3 v:v saturated CCA: 5 ng/mL nitrocellulose in 1:1 isopropanol:acetone). The samples were washed with 0.1% TFA before analysis. The peptide mass fingerprint obtained for each digest was matched to predicted digest patterns from known protein sequences using MS-FIT (http://prospector.ucsf.edu/ucsfhtml3.2/msfit.htm). As shown in Table 3, comparison of the observed molecular ions to the expected human TOP trypsin fragmentation pattern resulted in 20 bands with predicted mass. These matches accounted for 33% of the known Human TOP sequence (Thompson, et al. "Cloning and functional expression of a metalloendopeptidase from human brain with the ability to cleave a beta-APP substrate peptide," Biochem Biophys Res Commun 213: 66-73 (1995)). MALDI-tof analysis of the 63 KD band after trypsin digest indicated that it shared the same sequence but with the absence of a small portion of the carboxy terminus.

TABLE 3

| $M_r$ (observed) | $M_r + H^+$ (calculated) | Start | end | Number |
|---|---|---|---|---|
| 1374.56 | 1374.66 | 25 | 35 | 11 |
| 2337.06 | 2337.07 | 46 | 65 | 20 |
| 1464.6 | 1464.76 | 66 | 78 | 13 |
| 1481.6 | 1481.77 | 79 | 91 | 13 |
| 1343.51 | 1343.59 | 104 | 114 | 11 |
| 915.58 | 915.52 | 121 | 127 | 7 |
| 1014.55 | 1014.53 | 131 | 139 | 9 |
| 806.62 | 806.46 | 151 | 157 | 7 |
| 1177.63 | 1177.63 | 220 | 228 | 9 |
| 2089.9 | 2090.01 | 268 | 285 | 18 |
| 1651.61 | 1651.85 | 286 | 300 | 15 |
| 1069.64 | 1069.59 | 301 | 309 | 9 |
| 785.67 | 785.51 | 310 | 316 | 7 |
| 1332.5 | 1332.58 | 338 | 347 | 10 |
| 932.46 | 932.46 | 400 | 409 | 10 |
| 1086.6 | 1086.55 | 410 | 417 | 8 |
| 1133.63 | 1133.60 | 543 | 552 | 10 |
| 2129.97 | 2129.97 | 559 | 577 | 19 |
| 1149.62 | 1149.62 | 626 | 635 | 10 |
| 921.56 | 921.5 | 667 | 674 | 8 |
| | | | Total | 224 |
| | | | % of all (688) | 33% |

Electrospray ionization (ESI) quadrupole time of flight (Q-tof) tandem mass spectrometry was performed using a Q-tof instrument (Micromass) with a Z-Spray ion source working in the nanospray mode. About 3-5 µL of purified sample was introduced into a sample needle (PROTANA Inc., Odense, DK) to run MS and MS/MS experiments. The average capillary potential was 1000 V and the sample cone was set to 50V. Human [Glu$^1$]-fibrinopeptide B was used to calibrate the instrument in the MS/MS mode. MS/MS spectra were transformed using MaxEnt3 and sequences were determined using PepSeq (Micromass BioLynx).

As further confirmation of structural identity, two of the HeLa cell 74 KD tryptic fragments were sequenced by electrospray ionization (ESI) quadrupole time of flight (Q-tof) tandem mass spectrometry. As shown in Table 4, both fragments completely matched the known sequence of human TOP (Thompson, et al. "Cloning and functional expression of a metalloendopeptidase from human brain with the ability to cleave a beta-APP substrate peptide," *Biochem Biophys Res Commun* 213: 66-73 (1995)). By comparison, the sequences were close but not identical to those of rat and pig TOP.

L-alanine compound versus the P2 β-alanine compound. However, with the partially purified trouase preparation, the extent of cleavage of the P2 L-alanine compound was only 0.6 fold that of the P2 β-alanine compound. These results suggest that the presence of L-alanine at P2 may have provided a second cleavage site for the cruder mixtures of enzymes; thus reducing the likelihood that, in vivo, release of the active drug would be localized to tumor tissue.

TABLE 4

| Fragment Ion Sequence (m/z) | Human TOP Residue | Human TOP Identity | Rat TOP Residue | Rat TOP Identity | Pig TOP Residue | Pig TOP Identity |
|---|---|---|---|---|---|---|
| A(I/L)ADVEVTYTVQR (1464.65) | 66-78 | 100% | 66-79 | 100%* | 66-78 | 92% |
| WDLSAQQIEER (1374.43) | 25-35 | 100% | 25-35 | 73% | 25-35 | 82% |

*extra amino acid inserted in Rat TOP sequence

Example 13

Immunoprecipitation

Immunoprecipitation was performed in two steps. In the first step 5 μL test enzyme was incubated 1 hr at 4° C. with 10 μL 1:250 diluted anti-TOP or irrelevant rabbit IgG in pH 7.2 10 mM hydroxyethylpiperazine (HEPES), 150 mM NaCl solution. In the second step, this mixture was added to 15 μL Protein A Sepharose (Amersham Pharmacia Biotech) equilibrated in the same buffer and incubated at 4° C. for 1 hr. After microcentrifugation, residual enzyme activity was determined in the supernatant.

Immunoprecipitation provided a further indication of structural identity. Partially purified HeLa trouase (F1) activity was completely removed from solution after incubation with rabbit anti-TOP followed by Sepharose® bead immobilized protein A. Similarly, MCF-7/6 cell homogenate trouase activity was 80% reduced by immunoprecipitation with the rabbit anti-TOP antibody. Control experiments showed that under the same conditions rR-TOP was completely immunoprecipitated but that incubation with irrelevant rabbit antibody did not precipitate either rR-TOP, HeLa cell trouase activity or MCF 7/6 trouase activity.

Example 14

Specificity for Trouase is Provided by a Non-Genetically Encoded Amino Acid at Position P2

Specificity is afforded by incorporation of a non-genetically encoded rather than a genetically encoded amino acid at position P2. Specifically, Suc-βAla-Leu-Ala-Leu-Dnr, which contains the non-genetically encoded amino acid β-alanine at position P2, was incubated, as described in Example 5, with each of the three preparations described in Examples 1-3. The extent of cleavage was then estimated by HPLC analysis of the resulting mixtures. These results were compared to results for the same incubations performed with the same compound except for a substitution of the genetically encoded amino acid L-alanine position at P2, e.g., Suc-βAla-Leu-Ala-Leu-Dnr vs. Suc-Ala-Leu-Ala-Leu-Dnr. The extent (rate) of cleavage by cell homogenate was 1.3 fold greater for the P2

Example 15

Prodrugs have Poor Cellular Uptake Prior to Cleavage

Promyelocytic leukemia cells, HL-60, were cultured in RPMI media containing 10% heat inactivated fetal calf serum (FCS). On the day of the study, the cells were collected, washed and resuspended at a concentration of $0.5 \times 10^6$ cells/ml in RPMI containing 10% FCS. 100 μl/well of cell suspension was added to 96 well plates. Serial dilutions (3-fold increments) of doxorubicin or test compounds were made and 100 μl of compounds were added per well. Finally, 10 μl of a 100 μCi/ml $^3$H-thymidine was added per well and the plates were incubated for 24 hours. The plates were harvested using a 96 well Harvester (Packard Instruments) and counted on a Packard Top Count counter. Four parameter logistic curves were fitted to the $^3$H-thymidine incorporation as a function of drug molarity using Prism software to determine $IC_{50}$ values.

TABLE 5

| | $IC_{50}$ (μM) in HL-60 cells |
|---|---|
| Doxorubicin | 0.075 |
| Leucyl-Doxorubicin | 0.222 |
| Suc-βAla-Leu-Ala-Leu-Dox | >50 |

Doxorubicin exhibits potent cytotoxic activity with an $IC_{50}$ of 0.075 μM in HL60 cells. In contrast, the prodrug Suc-βAla-Leu-Ala-Leu-Dox has poor cellular uptake and an $IC_{50}$ greater than 50 μM in the HL-60 proliferation assay. In vivo cleavage studies show that leucyl-doxorubicin was the intermediate formed after proteolytic cleavage of the prodrug Suc-βAla-Leu-Ala-Leu-Dox. Therefore, leucyl-doxorubicin was tested and shown to have an $IC_{50}$ of 0.222 μM. These data support the concept that leucyl-doxorubicin is taken up by cells, where it is cleaved to release active doxorubicin.

Example 16

Comparative Metabolism in Mice

Two groups of ICR normal female mice were administered a single IV bolus dose with approximately 100 μmol/Kg of Suc-βAla-Leu-Ala-Leu-Dox or 10 μmol/Kg of doxorubicin (Dox). Plasma was obtained from three individual animals in each group at 5 minutes, 1, 2, 4, or 6 hr. Parent, dipeptidyl-doxorubicin (AL-Dox), α-aminoacyl-doxorubicin (L-Dox) and doxorubicin concentrations were analyzed in extracts of the plasma samples using a reverse phase gradient HPLC method with fluorescence detection ($\lambda$ex=480 nm, $\lambda$em=560). Quantities were determined using a linear standard curve fit to measurements of 10 to 2000 ng/mL doxorubicin solutions in mouse plasma.

Based on the time couse up to six hours, L-Dox was the major metabolite over the first two hr while the dipeptidyl-conjugate AL-Dox was a more minor product that formed at about the same time as L-Dox. Doxorubicin appeared later with the plasma concentration decreasing more slowly over time than the other metabolites as expected from the current and previously measured doxorubicin pharmacokinetic profiles (Van der Vijgh, et al. "Comparative metabolism and pharmacokinetics of doxorubicin and 4'-epidoxorubicin in plasma, heart and tumor of tumor-bearing mice," *Cancer Chemother Pharmacol,* 26(1): 9-12 (1990); and Tabrizi-Fard, et al., "Evaluation of the Pharmacokinetic Properties of a Doxorubicin Prodrug in Female ICR(CD1®) Mice Following Intravenous Administration," *Proc. Amer. Assoc. Cancer Res,* 42:324 (2001)) and by the doxorubicin control group. This is consistent with subsequent sequential cleavage by exopeptidase activity. The area under the plasma concentration time curve for (AUC) doxorubicin (Table 6) shows that Suc-βAla-Leu-Ala-Leu-Dox produced equivalent doxorubicin exposure to doxorubicin alone. It should be noted that relative Doxorubicin exposure after dosing these compounds resembles relative safety expressed as maximum tolerated dose in a mouse safety study.

TABLE 6

Area under plasma concentration curve ($AUC_{0-8\ hr}$) following equitoxic dosage in normal mice

| Dosed Compound | Parent | AL-Dox ($\mu M \cdot hr$) | L-Dox | Dox |
|---|---|---|---|---|
| Suc-βAla-Leu-Ala-Leu-Dox | 806 | 3.2 | 40 | 3.4 |
| Doxorubicin (Dox) | N/A | N/A | N/A | 3.3 |

So, 10 times the dose of Suc-βAla-Leu-Ala-Leu-Dox produced similar exposure to doxorubicin. In this study, Suc-βAla-Leu-Ala-Leu-Dox was dosed at approximately twice its single dose (SD) and repeat dose (RD) MTD while doxorubicin was dosed at approximately 25% of its SD MTD, but at a dose which is equivalent to the RD MTD. The rapid clearance of non-cleaved Suc-βAla-Leu-Ala-Leu-Dox from plasma apparently results in higher relative tolerability of the Suc-βAla-Leu-Ala-Leu-Dox compound compared with doxorubicin. Doxorubicin is cleared relatively more slowly. Thus the prodrug is advantageous in repeat-dose treatments, such as those used in chemotherapy, as it allows doseing to effecting levels of doxorubicin exposure while safely clearing excess drug, shown by the relative difference in MTD.

Example 17

The Prodrug is Effective and Well-Tolerated in Tumor Xenograft Models

Figure 11:
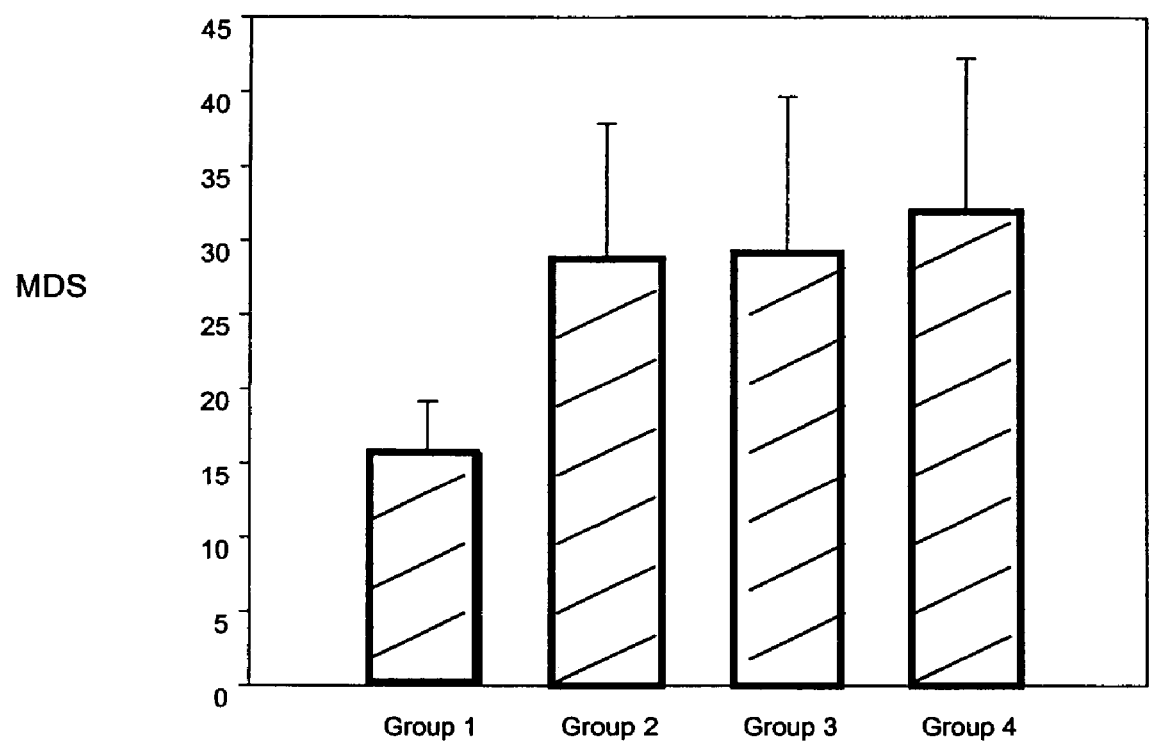
FIG. 11 is a graph of survival in a mouse xenograft model for animals given vehicle with or without drug.

Suc-βAla-Leu-Ala-Leu-Dox has proven to be efficacious in inhibiting the growth of human tumors in several nude mouse xenograft models, including the estrogen-dependent MCF-7/6 mammary tumor and the adriamycin-resistant colorectal carcinomas CXF280/10 and LS-174T. For example, when groups of 10 mice with subcutaneously-implanted LS174T tumors were treated with five weekly intravenous doses of Suc-βAla-Leu-Ala-Leu-Dox therapeutic agent, a significant, dose-dependent, replicable extension in the Mean Day of Survival (MDS) was observed, as well as decreased size of the tumor (tumor volume) compared with vehicle-treated controls (Group 1) at doses of 57 (Group 2), 64 (Group 3), and 71 (Group 4) mg/kg of Suc-βAla-Leu-Ala-Leu-Dox, with the highest dose being equivalent to 40 mg/kg of doxorubicin (See FIG. 11). The drug was safe and well-tolerated under repeat-dose levels and frequencies of dosing that demonstrated anti-tumor efficacy. Some dose-dependent body weight loss was observed. In supporting studies, kidney toxicity and myelosuppression were not observed at doses of up to 106.8 mg/kg of Suc-βAla-Leu-Ala-Leu-Dox.

Example 18

Suc-βAla-Leu-Ala-Leu-Dox is Better Tolerated in Vivo than Doxorubicin

Suc-βAla-Leu-Ala-Leu-Dox, an exemplary tetrapeptide prodrug of the invention, is well tolerated in mice. In a second single dose Maximum Tolerated Dose (SD-MTD) study, groups of five normal ICR mice were administered intravenous bolus doses of Suc-βAla-Leu-Ala-Leu-Dox. The mice were observed daily for 49 days and body weights measured twice weekly. Dose levels tested were 0, 50, 75 or 100 mg/kg, equivalent to 0, 28, 42 or 56 mg/kg of doxorubicin, respectively. There was no acute toxicity, within 24 hours, at any dose level. Dose and time dependent signs of toxicity were observed during the study. Toxicity, including partial hind-end paralysis and significant body weight loss (>20% of their initial weight) was observed in the 75 and 100 mg/kg dose groups. By Day 35 mortality was observed in 40% of the 75 mg/kg dose group. Based on survival and lack of signs of toxicity at Day 49, the SD-MTD for Suc-βAla-Leu-Ala-Leu-Dox was determined to be 50 mg/kg (equivalent to 28 mg/kg of doxorubicin). This dose was very well tolerated and no adverse effects were observed. Therefore, the SD-MTD was approximately 1.8-fold higher on a molar basis than the SD-MTD for doxorubicin alone (16 mg/kg). See Table 7. This is an approximate SD-MTD determination based on a range of doses at 14 mg/kg doxorubicin equivalents increments over the range tested.

Preliminary observations regarding the prodrug's toxicity profile indicated that it was generally consistent with that of doxorubicin, including later paralysis and wasting. However some differences were seen which could indicate a favorable shift in the toxicity profile, including lack of evidence of characteristic GI-toxicity, cardiotoxicity and myleosuppression of doxorubicin. No gross effects on the kidney were observed

TABLE 7

| Compound Name | SD-MTD (mg/kg) | SD-MTD (mg/kg Dox =) | SD-MTD Molar Ratio (Dox =) |
|---|---|---|---|
| Doxorubicin | 16 | 16 | 1 |
| Suc-βAla-Leu-Ala-Leu-Dox | 50 | 28 | 1.8 |

Example 19

The Prodrug is Safer and More Effective than Comparators

Figure 12:
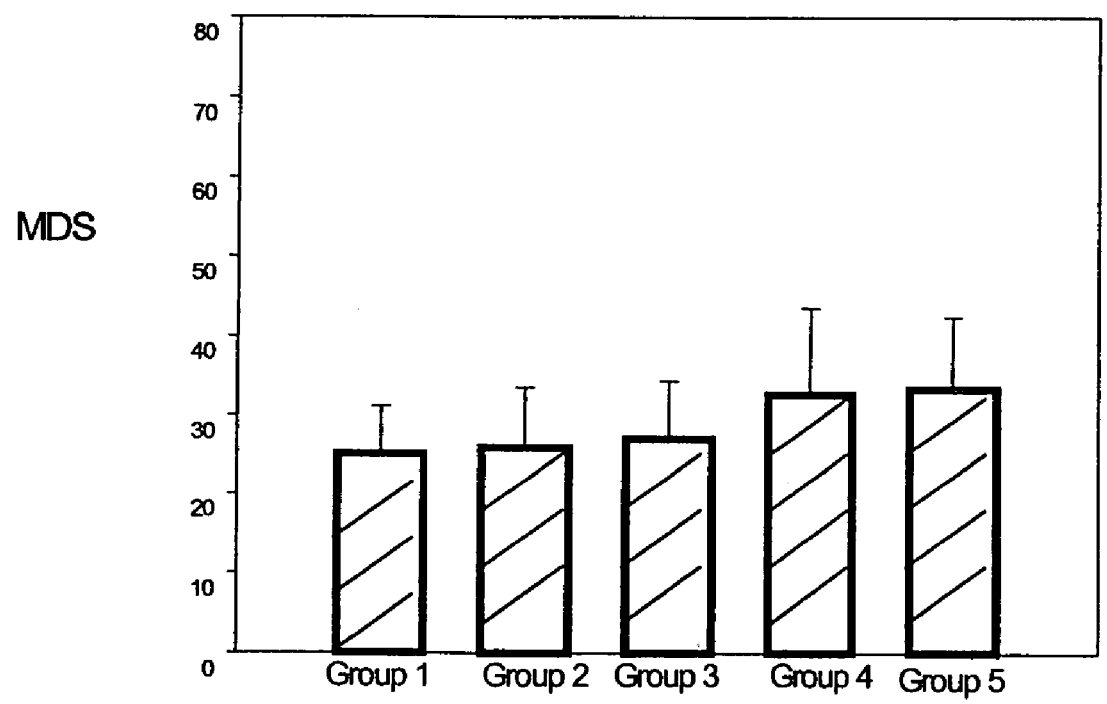
FIG. 12 is a graph of survival in a mouse xenograft model comparing a doxorubicin prodrug and doxorubicin.

Significantly higher doses of Suc-βAla-Leu-Ala-Leu-Dox could be administered compared with doxorubicin, achieving efficacy without significant toxicity in the LS-174T human colorectal carcinoma xenograft model. Suc-βAla-Leu-Ala-Leu-Dox, at well-tolerated doses of 49 (Group 3), 57 (Group 4), and 64 mg/kg (Group 5), showed superior efficacy compared to doxorubicin at 3.0 mg/kg (Group 2) and saline (Group 1) in inhibiting the rapidly-growing adriamycin-resistant LS-174T tumor (FIG. 5), and extending survival of tumor-bearing mice (FIG. 12). Dose limiting toxicity (cardiotoxicity and myelosuppression) has been observed with repeated administration of doxorubicin in humans. Thus we have demonstrated that higher doses of Suc-βAla-Leu-Ala-Leu-Dox than doxorubicin can be administered, favoring tumor inhibition over systemic toxicity.

Example 20

Prodrugs are Useful Against Moderately Doxorubicin Sensitive Tumors

MX-1 tumors which are moderately doxorubicin-sensitive, human breast carcinoma xenografts, were implanted subcutaneously (s.c.) and mice were weighed and tumors were measured (by caliper) at least once a week prior to start of dosing (Day 0), then twice a week during the study. Immediately before the start of dosing (Study Day −2 to Day 0), mice were randomized to various groups based on the weight of the tumors. Mice were euthanized after the tumors reached a cutoff weight of 1.5 g (cancer endpoint). Studies were terminated at Day 60.

Figure 18:
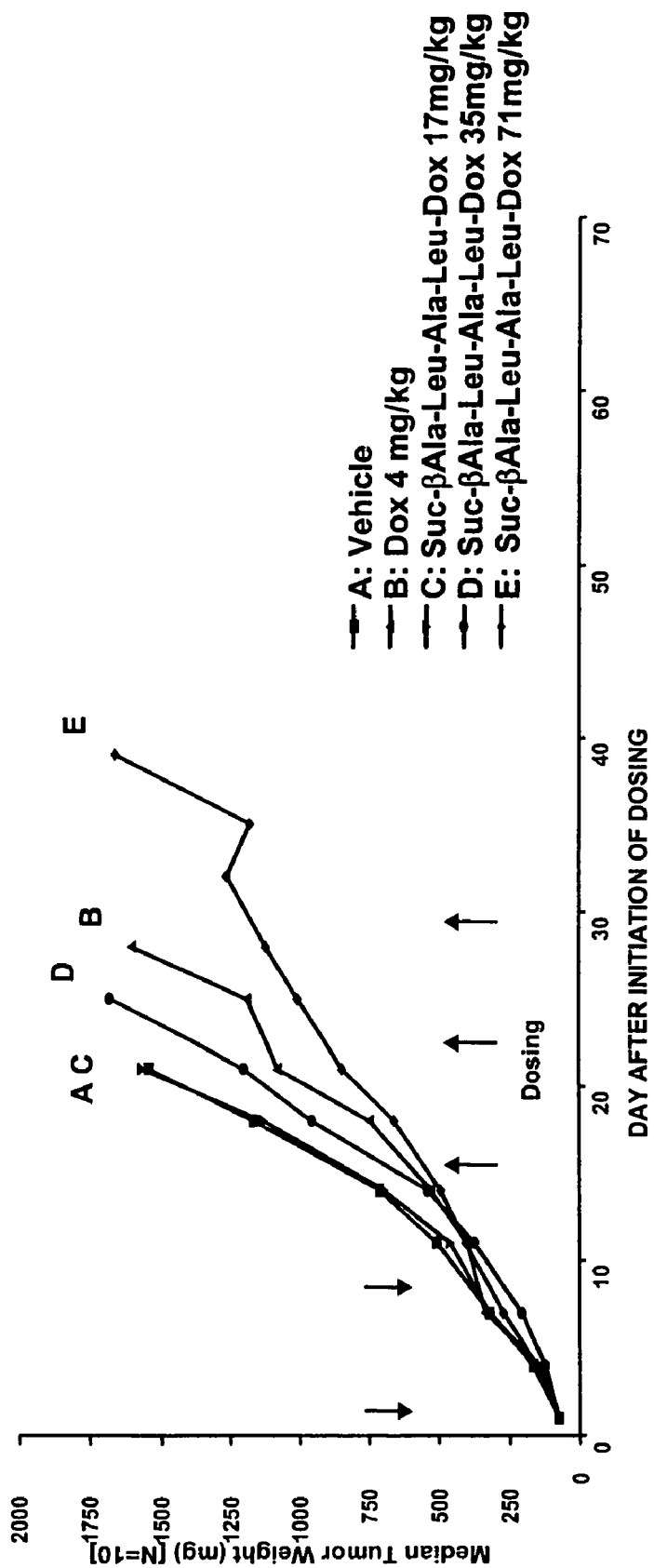
FIG. 18 is a comparison of the effects of Suc-bAla-Leu-Ala-Leu-Dox and doxorubicin compared with vehicle on the growth of MX-1 human breast tumors in female nude mice.

The control group tumors grew rapidly and all animals were terminated at the cancer endpoint by Day 24. The tumor exhibited relatively homogeneous growth characteristics, reaching the cancer endpoint ranging from Day 15-24. Doxorubicin was effective in significantly prolonging the survival of tumor-bearing mice (Table 8). A dose response was established for Suc-βAla-Leu-Ala-Leu-Dox both in inhibiting MX-1 tumor growth and prolonging mouse survival (FIG. 18 and Table 8). Suc-βAla-Leu-Ala-Leu-Dox at 71 mg/kg was significantly better than doxorubicin in inhibiting tumor growth and extending mouse survival (Table 8). All three dose regimens of Suc-βAla-Leu-Ala-Leu-Dox as well as doxorubicin were very well tolerated. Only one out of ten mice in the Suc-βAla-Leu-Ala-Leu-Dox 71 mg/kg group had up to 20% weight loss towards the end of the study (after Day 46).

Example 21

Prodrugs are Useful in Evasion of Multi-Drug Resistance Mechanisms

Suc-βAla-Leu-Ala-Leu-Dox has been shown to be much more active than free doxorubicin on MDR human cell lines implanted into mice in xenograft models. Doxorubicin delivered to the tumor in a modified form, specifically in prodrug form as Suc-βAla-Leu-Ala-Leu-Dox, shows activity in slowing tumor growth resulting in significant extension of survival in the dose group.

Figure 15:
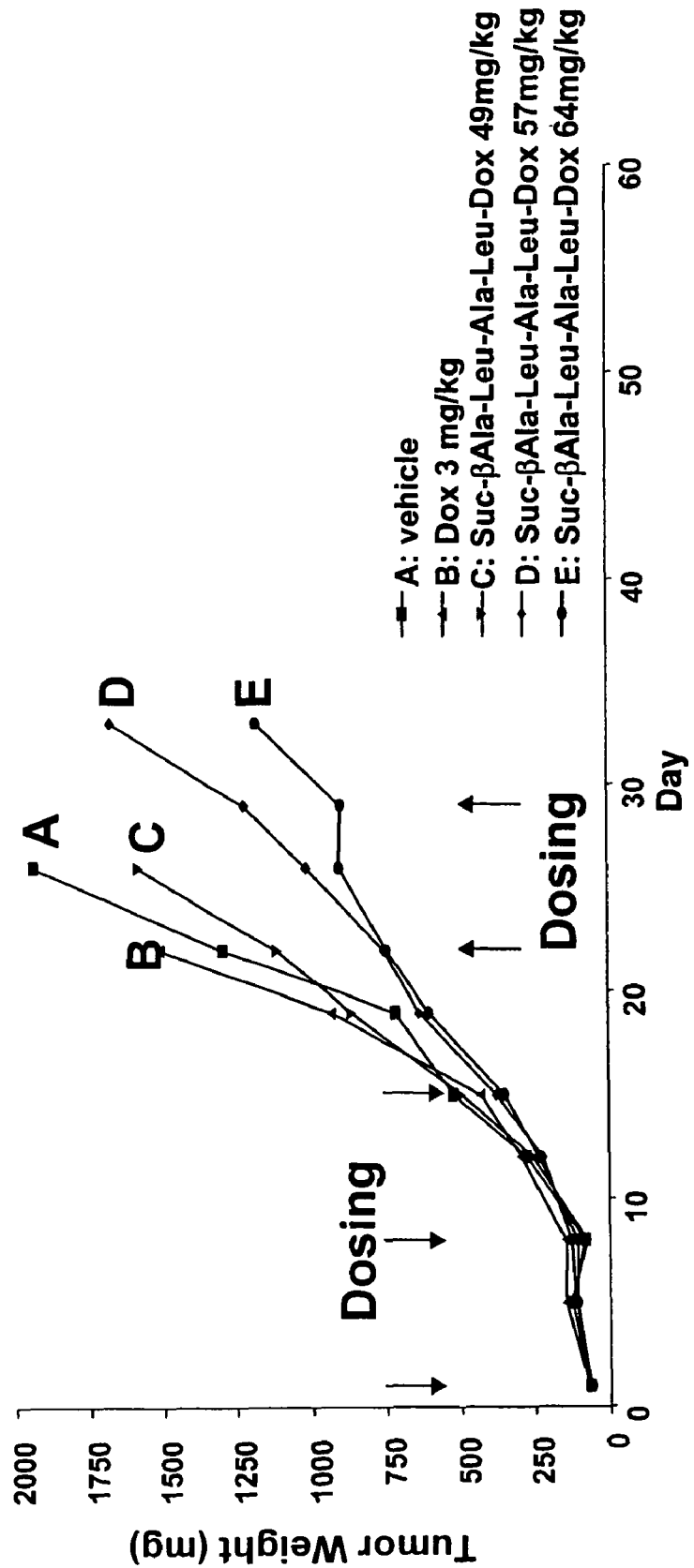
FIG. 15 is a graph of tumor growth inhibition in a mouse xenograft model.

Table 9 and FIG. 15 show that with Suc-βAla-Leu-Ala-Leu-Dox there is dose-dependent increase in survival in the MDR human colorectal carcinoma LS174-T. LS174T is a very aggressive and rapidly growing tumor that exhibits heterogeneous cell morphology with a necrotic center. It is very resistant to conventional chemotherapeutics, and there are always tumors in some animals that become so well established within a few days that they rapidly outgrow attempts to inhibit tumor growth, thus the animals reach the tumor endpoint despite treatment. Doxorubicin alone is completely inactive in this model, producing no effects on tumor growth or on survival.

TABLE 8

MX-1 Study Summary

| Cmpd | Dose# (mg/kg) | Tumor Weight (mg, Day 18) | TGI | MDS (day) | TGD (day) | Survival: MDS Extension over controls |
|---|---|---|---|---|---|---|
| Saline | — | 1158 ± 109 | — | 20.5 ± 0.8 | — | — |
| Doxorubicin | 3 | 906 ± 150 | 22 ± 16% | 27.3 ± 2.6 | 6.8 ± 2.7 | 33 ± 13%* |
| Suc-βAla-Leu-Ala-Leu-Dox | 17 | 1219 ± 90 | 0% | 20.0 ± 0.7 | 0.0 | 0% |
| Suc-βAla-Leu-Ala-Leu-Dox | 35 | 911 ± 84 | 21 ± 12% | 23.6 ± 1.0 | 3.1 ± 1.3 | 15 ± 6%* |
| Suc-βAla-Leu-Ala-Leu-Dox | 71 | 702 ± 69 | 39 ± 11%** | 37.1 ± 3.5 | 16.6 ± 3.5 | 81 ± 18%**$ |

Doses of all compounds were administered 5 times, one dose every 7 days
*Statistically different from the control at the p level of 0.05 (two-tailed unpaired t test)
**Statistically different from the control at the p level of 0.01 (two-tailed unpaired t test)
$Statistically different from the doxorubicin group at the p level of 0.05 (two-tailed unpaired t test)
TGI: % tumor growth inhibition over control at Day 18
MDS: Mean day of survival
TGD: Tumor growth delay over control

TABLE 9

LS174T Study Summary

| Compound | Dose (mg/kg) | Mean Tumor Weight (mg, Day 19) | TGI | MDS (day) | TGD (day) | MDS Extension over controls |
|---|---|---|---|---|---|---|
| Saline | — | 780 ± 199 | — | 25.0 ± 1.9 | — | — |
| Doxorubicin | 3 | 1035 ± 180 | 0% | 25.8 ± 2.5 | 0.8 ± 3.1 | 3 ± 13% |
| Suc-βAla-Leu-Ala-Leu-Dox | 49 | 838 ± 120 | 0% | 27.1 ± 2.3 | 2.1 ± 3.0 | 8 ± 12% |
| Suc-βAla-Leu-Ala-Leu-Dox | 57 | 646 ± 122 | 17 ± 30%* | 32.7 ± 3.5* | 7.7 ± 4.0 | 31 ± 16%* |
| Suc-βAla-Leu-Ala-Leu-Dox | 64 | 684 ± 127 | 12 ± 30% | 33.3 ± 2.9* | 8.3 ± 3.5 | 33 ± 14%**$ |

For all compounds 5 doses were administered, one dose every 7 days
*Statistically different from the control at the p level of 0.1 (two-tailed unpaired t test)
**Statistically different from the control at the p level of 0.05 (two-tailed unpaired t test)
$Statistically different from the doxorubicin group at the p level of 0.1 (two-tailed unpaired t test)
TGI: % tumor growth inhibition over control at Day 18
MDS: Mean day of survival
TGD: Tumor growth delay over control Specifically, Table 9 provides a summary of the effects of Suc-βAla-Leu-Ala-Leu-Dox at three dose levels as compared to doxorubicin in the LS174T colorectal carcinoma xenograft in nude mice (Q7Dx5). Parameters measured include the calculated Mean Day of Survival (MDS) determined by termination due to tumors reaching the predetermined cutoff size of 1500 mg (tumor death), number of Long Term Survivors (LTS), and tolerability of the dose regimen, by number of mice exhibiting toxic death (>20% body weight loss). The number of LTS at day 60 was zero in all groups. No toxic deaths were observed in any of the groups. Statistically significant from vehicle control group: *: p<0.05; **: p<0.01 (unpaired t-test).

The control group tumors grew rapidly and all animals were terminated at the cancer endpoint by Day 33. The tumor exhibited heterogeneous growth characteristics, reaching the cancer endpoint between Day 15 to Day 33. Doxorubicin (3 mg/kg) was ineffective in inhibiting LS174T tumor growth or prolonging survival. A dose response was established for Suc-βAla-Leu-Ala-Leu-Dox in prolonging mouse survival (Table 9). Suc-βAla-Leu-Ala-Leu-Dox at 64 mg/kg was significantly better than doxorubicin in extending mouse survival (Table 9). Suc-βAla-Leu-Ala-Leu-Dox at 57 mg/kg significantly inhibited LS174T tumor growth (FIG. 15 and Table 9). All three dose regimens of Suc-βAla-Leu-Ala-Leu-Dox and doxorubicin were very well tolerated, with no termination due to toxic endpoints.

In addition, Suc-βAla-Leu-Ala-Leu-Dox, dosed at three well-tolerated dose-levels (Q7dx5), but not doxorubicin, showed a dose dependent inhibitory effect on median tumor weight (FIG. 15).

FIG. 15 shows effects of Suc-βAla-Leu-Ala-Leu-Dox compared with doxorubicin on tumor growth of LS174T tumor colorectal carcinoma xenografts in nude mice and vehicle-control. Group D was statistically significantly different from the vehicle control group at Day 19 (p<0.05).

These results suggest that the local generation of the active cytotoxin at high concentrations in the tumor may be key to the prodrug form of the therapeutic agent overcoming MDR pathways.

Example 22

βAla-Leu-Ala-Leu-Dox Aggregation

Poorly soluble anthracycline drugs have been shown to form aggregates when prepared in aqueous buffers. Menozzi, et al., "Self-association of doxorubicin and related compounds in aqueous solutions," *J Pharmaceut. Sci.*, 73:766-770 (1984). Confalonieri, et al., "The use of new laser particle sizer and shape analyser to detect and evaluate gelatinous microparticles suspended in reconstituted anthracycline infusion solutions," *J Pharmaceut. Biomed. Anal.* 9:1-8 (1991). An estimation of βAla-Leu-Ala-Leu-Dox aggregate size in a 17.4 μMol/ml aqueous solution was made by attempting to filter these solutions through Amicon Centricon™ filter units. Doxorubicin (17.4 μMol/ml) and βAla-Leu-Ala-Leu-Dox (17.4 μMol/ml) were each dissolved in distilled water and placed into Centricon filters with 3,000, 10,000, 30,000 and 50,000 molecular weight cutoff (MWCO). Each filter unit was centrifuged for 2 hr at 1500 g force. The amount of the drug retained and passing through the filter was quantitated at λ475 nm and converted to a percent. Table 10 below shows that 81% of the doxorubicin passed through the 3,000 MWCO filter while only 5% of the conjugate, βAla-Leu-Ala-Leu-Dox passed through the 3,000 MWCO filter. The data also show that the 50,000 MWCO unit retains over 40% of the βAla-Leu-Ala-Leu-Dox. These data demonstrate that a significant percentage of βAla-Leu-Ala-Leu-Dox aggregates were larger that 50 kD (>50 molecules/aggregate). Thus, βAla-Leu-Ala-Leu-Dox may aggregate under some conditions.

TABLE 10

| | 3000 MWCO | | 10000 MWCO | | 30000 MWCO | | 50000 MWCO | |
|---|---|---|---|---|---|---|---|---|
| | Filt. | Ret. | Filt. | Ret. | Filt. | Ret. | Filt. | Ret. |
| Dox | 81% | 10% | 82% | 2% | n.d. | n.d. | 93% | 0.5% |
| Conj. | 4.9% | 89% | 10% | 76% | 36% | 64% | 53% | 43% |

Dox: doxorubicin;
Conj: β-Ala-Leu-Ala-Leu-Doxorubicin

Example 23

Intravenous Injection of βAla-Leu-Ala-Leu-Dox in Mice

It is known that acute toxicity likely occurs through the interaction of positively charged polymers, such as protamines, polylysine, or their aggregates, and the luminal surface of blood vessels. DeLucia, et al., "Efficacy and toxicity of differently charged polycationic protamine-like peptides for heparin anticoagulation reversal," *J Vasc. Surg.* 18:49-60 (1993). Ekrami, et al., "Carbamylation decreases the cytotoxicity but not the drug-carrier properties of polylysines," *J. Drug Targ.* 2:469-475 (1995). It has been further shown that heparin reduces the toxic effects of protamine sulfate on rabbit myocardium. Wakefield, et al., "Heparin-mediated reductions of the toxic effects of protamine sulfate on rabbit myocardium," *J Vasc. Surg.* 16:47-53 (1992). To test the hypothesis that the acute toxicity seen here was due to positively charged prodrug aggregates, βAla-Leu-Ala-Leu-Dox (174 μMol/ml) was given to mice following a 1 hr pretreatment with 4,000 I.U. heparin, intravenously, as compared to control. Table 12 shows that following heparin, a formerly acutely lethal dose of βAla-Leu-Ala-Leu-Dox was significantly less toxic.

These data support the hypothesis that the acute toxicity is due to a positively charged aggregate causing a similar effect to that seen for protamines or polylysine. Negatively and neutrally charged prodrugs of the invention overcome this undesirable side effect.

TABLE 12

| ROUTE OF Pretreatment | HEPARIN DOSE LEVEL (I.U.) | Survival time (days) [Proportion] | Acute toxicity (Proportion) |
|---|---|---|---|
| Control (iv) | 0 | 0 | 5/5 |
| i.p. | 4000 | >9 [5/8] | 3/8 |
|  | 8000 | >11 [3/3] | 0/3 |
| i.v. | 4000 | >11 [2/3] | 1/3 |

In agreement with the aforementioned hypothesis, capping the terminal amino group of βAla-Leu-Ala-Leu-Dox with a negatively charged moiety resulted in the complete disappearance of the acute toxicity effect at dose levels as high as 250 mg Dox-HCL, eq./Kg.

As evidence of this, in a related experiment, all animals survived up to 8 days when three to five mice per group were treated with an intravenous bolus of 250 mg/kg (Dox-HCl eq.) Suc-βAla-Leu-Ala-Leu-Dox or Gl-βAla-Leu-Ala-Leu-Dox.

Analytical Methods for the Remaining Examples

The peptide sequences, synthesized using either solid or solution phase approaches, were used without further purification if the analytical HPLC (methods A, B & D) showed the crude product to be greater than 80% pure. If not, the material was purified using preparative HPLC Method C.

HPLC Method A

Analytical HPLC analyses were performed on a Waters 2690 using a C-18 column (4 μm, 3.9×150 mm ID, flow rate 1 mL/min) eluting with a gradient of solvent A (0.1% TFA/H$_2$O) and solvent B (0.1% TFA/ACN) and the data was processed at λ 254 nm using the Waters Millennium system. Analytical HPLC gradient started with 90% of solvent A and ended with 100% of solvent B over a period of 14 minutes (linear). Purity of the compounds for this method and the following ones was assessed as the relative percentage area under the curve of the peaks.

HPLC Method B

Analytical HPLC analyses were performed on a Waters 2690 using a C-8 column (3.5 μm, 4.6×150 mm ID, flow rate 1 mL/min) eluting with a gradient of solvent A (80% 20 mM ammonium formate and 20% acetonitrile) and solvent B (20% 20 mM ammonium formate and 80% acetonitrile) and the data was processed at λ 254 nm using the Waters Millennium system. Analytical HPLC gradient started with 100% of solvent A to 100% of solvent B over a period of 30 minutes (linear).

HPLC Method C

Preparative purification of crude products was achieved using a Waters Delta Prep 4000 system using a C-4 column (15 μm, 40×100 mm ID, flow rate 30 mL/min) eluting with a gradient of solvent A (H$_2$O), and solvent B (MeOH). The preparatory HPLC gradient started with 80% of solvent A and goes to 100% of solvent B over a period of 70 minutes (linear). The data was processed at λ 254 nm using the Waters Millennium System.

HPLC Method D

Analytical HPLC was accomplished on a Hewlett Packard instrument using a TSK superODS column (TosoHaas); solvent A (TFA 0.1% in water); solvent B (TFA 0.1% in acetonitrile); gradient: 30 to 36% of B in 2 minutes, 36 to 41% of B in 10 minutes, 41 to 90% of B in 3 minutes, 5 minutes at 90% B, detection wavelength λ 254 nm.

NMR and MS

Additional structural determinations were done by NMR and MS techniques and the results supported the claimed compounds.

TLC Method

TLC analysis was carried out on silica gel 60F-254 nm-0.25 mm plates (Merck) with DCM/MeOH/H$_2$O/Formic acid 88% 85/15/1/2 for elution.

Ninhydrin Test

A few milligrams of product were introduced in a test tube, and two drops of Solution A (50 mg/mL ninhydrin in ethanol), two drops of Solution B (4 mg/mL phenol in ethanol), then two drops of Solution C (2 mL 0.01 M KSCN, aqueous in 100 mL pyridine) were added. The mixture was left in a boiling water bath for five minutes. In the presence of a free amine the solution becomes purple.

Specific Oligopeptide Synthetic Examples

Sources of Commercially Available Reagents

Doxorubicin and Daunorubicin were supplied by Meiji (Japan), Pd(PPh$_3$)$_4$ by Strem chem (Newburyport, Mass.), PEG by Shearwater (Huntsville, Ala.), solvents, HATU by Aldrich (Milwaukee, Wis.); all resins and amino acids were supplied by ABI (Foster City, Calif.), Novabiochem (San Diego, Calif.), Advanced ChemTech (Louisville, Ky.), Peptide International (Louisville, Ky.), or SynPep (Dublin, Calif.).

Example 24

Fmoc Form of βAla-Leu-Ala-Leu Benzyl Ester

The Fmoc form of βAla-Leu-Ala-Leu (24.34 g, 0.04 mol) was added into a round bottom flask with DMF (350 mL) and a magnetic stirrer. After the tetrapeptide was dissolved, benzyl bromide (4.76 mL, 0.04 mol), followed by cesium carbonate (13.04 g, 0.04 mol), was added to the solution with stirring. The reaction mixture was stirred at room temperature for 1.5 hrs. Then, the reaction mixture was slowly poured into a flask with 450 mL of iced water. A large amount of white solid precipitated out which was collected by suction filtration. The product was washed with water (2×200 mL) and placed in a vacuum desiccator. The product (24.2 g, 87%) was identified by HPLC (Purity: 95%). MS m/z calcd. for $C_{40}H_{50}N_4O_7$ 698.4. Found 699.5.

Example 25

βAla-Leu-Ala-Leu Benzyl Ester

In a round bottom flask (25 mL), Fmoc form of βAla-Leu-Ala-Leu benzyl ester (0.7 g, 1.0 mmol) was dissolved in 5 mL of anhydrous DMF. Piperidine (1.2 mL, 12.1 mmol) was added to the solution and the mixture was stirred at room temperature for 25 minutes. The reaction was quenched with water (6 mL) and extracted with ethyl acetate (2×10 mL). The combined organic layer was further washed by water (2×5 mL), brine (5 mL) and dried over sodium sulfate. A white solid (0.8 g) was obtained after removal of solvent. The purity of the product was only 67%. MS m/z calcd. for $C_{25}H_{40}N_4O_5$ 476.3. Found 477.2.

Example 26

Methyl Succinyl-N-Cap Form of βAla-Leu-Ala-Leu Benzyl Ester

In a round bottom flask (250 mL), methyl hemisuccinate (3.19 g, 24.2 mmol) was dissolved in anhydrous DMF (50 mL). DIEA (4.22 mL, 24.2 mmol) followed by HBTU (9.17 g, 24.2 mmol) were added into the solution. The mixture was stirred at room temperature for 45 minutes. To this mixture was added a solution of βAla-Leu-Ala-Leu benzyl ester (crude, containing 10.14 g, 21.3 mmol) in anhydrous DMF (150 mL). The mixture was continually stirred at room temperature for 2.5 hrs. Then, the reaction mixture was slowly poured into a flask with 200 mL of iced water while stirring. A large amount of white solid precipitated out which was extracted by ethyl acetate (3×200 mL). The combined organic layer was further washed by water (2×200 mL), brine (200 mL) and dried over sodium sulfate. A white solid was obtained after removal of solvent. Recrystallization of this crude product in ethyl acetate afforded 7.53 g of product (60%) with purity of 80%. MS m/z calcd. for $C_{30}H_{46}N_4O_8$ 591.4. Found 590.33.

Example 27

Methyl Succinyl-N-cap form of βAla-Leu-Ala-Leu

Methyl succinyl-N-cap form of βAla-Leu-Ala-Leu benzyl ester (1.0 g, 86% purity; 1.46 mmol) was added into an Erlenmeyer flask with 100 mL of methanol. The solution was cloudy after being stirred for a few minutes. 50 mL of methanol was added, but the solution was still not clear. The solution was transferred into a hydrogenation reaction vessel. To this vessel, Pd—C (90 mg, 10% wet, 50% water; 0.042 mmol) was added. After hydrogenation for 2 hours at room temperature, the reaction was stopped and the catalyst was filtered. A white solid (0.77 g, 78%) was yielded after removal of solvents. MS m/z calcd. for $C_{23}H_{40}N_4O_8$ 501.2. Found 500.3.

Example 28

Synthesis of N-cap Allyl-Hemisuccinate

This molecule was prepared according the procedure of Casimir, J. R., et. al. *Tet. Lett.* 36(19):3409, (1995). 10.07 g (0.1 mol) succinic anhydride and 5.808 g (0.1 mol) allyl-alcohol were refluxed in 100 mL toluene for 6 hours. The reaction mixture was concentrated under reduced pressure. 15.5 g; 98%. The resulting material was pure enough to use in subsequent reactions. The purity and identity of the semi-solid product was confirmed by $^1$HNMR and $^{13}$CNMR, by LC/MS.

Example 29

Synthesis of Allyl-Succinyl-βAla-Leu-Ala-Leu-Dox

In a round bottom flask (50 ml) N-Cap-Allylhemisuccinyl form of βAla-Leu-Ala-Leu (1 g, 1.9 mmol) and doxorubicin (1.1 g, 1.9 mmol) were dissolved in anhydrous DMF (50 ml). After the mixture was stirred for 5 minutes, DIEA (0.66 ml, 3.8 mmol) followed by HATU (0.76 g, 1.9 mmol) was added into the solution the mixture was stirred at room temperature for 2 hours. DMF was removed by a rotary evaporator and the residue was taken up in 4.0 ml 1:1, DCM:MeOH. To this solution, 100 ml of ether was slowly added while stirring. A red precipitate was formed and collected by suction filtration. The solid was washed with ether (2×2 ml) and dried in a vacuum desiccator to give the Allyl-Succinyl-βAla-Leu-Ala-Leu-Dox therapeutic agent with 90% HPLC purity by Method B.

Example 30

Preparation of Suc-βAla-Leu-Ala-Leu-Dox from allyl-Succinyl-βAla-Leu-Ala-Leu-doxorubicin To a stirred solution of 0.1 g (0.095 mmol) allyl-succinyl-βAla-Leu-Ala-Leu-doxorubicin in 2 mL THF, under nitrogen atmosphere 0.05 g (0.095 mmol) tetrakis(triphenylphosphine) palladium was added as a solid. After 10 minutes the precipitate formed during the reaction was filtered off, washed with THF. Dry weight: 0.1 g. The solids have been identified by HPLC, $^1$HNMR, LC/MS to be succinyl-β-Ala-Leu-Ala-Leu-Dox.

Example 31

Synthesis of Fmoc Form of βAla-Leu-Ala-Leu

Fmoc form of βAla-Leu-Ala-Leu was synthesized using solid-phase approach with standard Fmoc chemistry. A typical synthesis used Wang's alkoxy resin (0.60 mmol/gm loading). Fmoc-protected amino acids were used for solid-phase peptide synthesis. For a scale of 1 mM peptide on resin, 3 equivalents of amino acid were preactivated with HBTU as the activating agent for 5 minutes before being added to the resin together with 2 equivalents of DIEA. The coupling reaction was carried out for 2 h and then washed with DMF (25 mL×3) and DCM (25 mL×3). The coupling reaction was repeated using 2 equivalents of amino acid under similar conditions. The reaction progress was monitored using ninhydrin test and if the ninhydrin test indicated incomplete reaction after 2 h then the coupling step was repeated for a third time. Deprotection was accomplished using 20% piperidine in DMF for 15-20 minutes. The coupling step was repeated with the next amino acid until the desired peptide was assembled on resin. The final cleavage of peptide from the resin was accomplished by treating the resin with a solution of 95% TFA and 5% water. After stirring the reaction mixture for 2 h at rt, the resin was filtered under reduced pressure and washed twice with TFA. Filtrates were combined and the peptide was precipitated by adding 400 mL of cold ether. The peptide was filtered under reduced pressure and dried to yield Fmoc form of βAla-Leu-Ala-Leu (94% HPLC purity by method A). Crude peptide was used for the next step without any further purification.

Example 32

Synthesis of Fmoc Form of Thi-Tyr-Gly-Leu

Fmoc form of Thi-Tyr-Gly-Leu was synthesized using solid-phase approach with standard Fmoc chemistry and Wang's alkoxy resin (0.60 mmol/gm loading). Fmoc-protected amino acids and Fmoc-Thi-OH were used for solid-phase peptide synthesis. For a scale of 1 mM peptide on resin, 3 equivalent of amino acid was preactivated with HBTU as the activating agent for 5 minutes before being added to the resin together with 2 equivalent of DIEA. The coupling reaction was carried out for 2 h and then washed with DMF (25 mL×3) and DCM (25 mL×3). The coupling reaction was repeated using 2 equivalent of amino acid using similar conditions. The reaction progress was monitored using the ninhydrin test and if the ninhydrin test indicated incomplete reaction after 2 h then the coupling step was repeated for a third time. Deprotection was accomplished using 20% piperidine in DMF for 15-20 minutes. The coupling step was repeated with the next amino acid until the desired peptide was assembled on resin. The final cleavage of peptide from the resin was accomplished by treating the resin with a solution of 95% TFA and 5% water. After stirring the reaction mixture for 2 h at RT, the resin was filtered under reduced pressure and washed twice with TFA. Filtrates were combined and adding 400 mL of cold ether precipitated the peptide. The peptide was filtered under reduced pressure and dried to yield Fmoc form of Thi-Tyr-Gly-Leu (88% HPLC purity by method A). Crude Fmoc form of Thi-Tyr-Gly-Leu was used for the next step without any further purification.

Example 33

Synthesis of Fmoc Form of βAla-Leu-Ala-Leu-Dnr Therapeutic Agent

Daunorubicin.HCl (185 mg, 0.329 mmol) and Fmoc form of βAla-Leu-Ala-Leu (200 mg, 0.329 mmol) were dissolved at room temperature in anhydrous DMF (15 mL). To this rapidly stirred solution, DIEA (0.115 mL, 0.658 mmol) was added in one portion and the reaction mixture was stirred for 15 minutes at room temperature. The reaction mixture was cooled to 0° C. using an ice bath and 138 mg (0.362 mmol) of HATU was added slowly over 10 minutes. The reaction mixture was stirred for another 90 minutes at room temperature. Ice cold water (200 mL) was added to the reaction mixture which resulted in the formation of a red precipitate. The precipitate was collected over a coarse frit, washed with 3×50 mL water and 3×50 mL diethyl ether and dried under reduced pressure to yield Fmoc form of βAla-Leu-Ala-Leu-Dnr Therapeutic Agent (94% yield, 95% HPLC purity by method A). This product was used for the next step without any further purification.

Example 34

Synthesis of Fmoc Form of Thi-Tyr-Gly-Leu-Dnr Therapeutic Agent

Daunorubicin.HCl (90 mg, 0.16 mmol) and Fmoc form of Thi-Tyr-Gly-Leu (120 mg, 0.16 mmol) were dissolved at room temperature in anhydrous DMF (15 mL). To this rapidly stirred solution, DIEA (0.56 mL, 0.16 mmol) was added in one portion and the reaction mixture was stirred for 15 minutes at room temperature. The reaction mixture was cooled to 0° C. using an ice bath and 61 mg (0.16 mmol) of HATU was added slowly over 10 minutes. The reaction mixture was stirred for another 90 minutes at room temperature. Ice cold water (150 mL) was added to the reaction mixture which resulted in the formation of a red precipitate. The precipitate was collected over a coarse frit, washed with 3×50 mL water and 3×50 mL diethyl ether and dried under reduced pressure to yield Fmoc form of Thi-Tyr-Gly-Leu-Dnr Therapeutic Agent (94% yield, 91% HPLC purity by method A). This product was used for the next step without any further purification.

Example 35

Preparation of Fmoc-βAla-Leu-Ala-Leu-doxorubicin 3.0 g (5.17 mmol) doxorubicin hydrochloride and 3.15 g (5.17 mmol) Fmoc-βAla-Leu-Ala-Leu were dissolved at room temperature in 230 mL dry DMF under nitrogen. To this rapidly stirred solution, 1.798 mL (10.34 mmol) DIEA was added in one portion and the reaction mixture stirred at room temperature for 15 min. The reaction mixture was cooled to ≈−2° C. in an ice/brine bath and 2.56 g (6.73 mmol) HATU in 58 mL DMF was added dropwise over 12 minutes with rapid stirring. The reaction mixture was stirred another 30 minutes at −2° C. then 0.285 mL (1.64 mmol) DIEA was added in one portion. 580 mL water at 0° C. was immediately resulting in formation of a flocculent red precipitate. The precipitate collected over a coarse glass frit, washed with 3×50 mL water and 3×50 mL diethyl ether in water and air dried 16 hours to yield 5.21 g Fmoc-βAla-Leu-Ala-Leu-Dox, 89.7% physical yield, 90.23% HPLC purity by Method B.

Example 36

Preparation of Succinyl-β-Ala-Leu-Ala-Leu-Dox From Fmoc-β-Ala-Leu-Ala-Leu-dox

To a solution of 5.0 g (4.41 mmol) Fmoc-βAla-Leu-Ala-Leu in 230 mL dry DMF under nitrogen at room temperature, 21.8 mL (220 mmol) piperidine was added in one portion resulting in a color change from red to purple. The reaction mixture was stirred 5 minutes at room temperature then cooled to about −20° C. in a dry ice/acetone bath. 22.5 g (0.225 mol) succinic anhydride was then added in one portion with the reaction temperature maintained below −5° C. After about 2 minutes stirring at −10° C. to −5° C., the color changed from purple to red/orange. The cooling bath was removed and the reaction mixture stirred for 10 minutes. The reaction mixture volume was then reduced to ≈100 mL by rotary evaporation and then diluted with 125 mL chloroform. To this solution, 1400 mL diethyl ether was quickly added resulting in formation of a red precipitate. This precipitate was isolated on a medium glass frit and triturated with 5×200 mL diethyl ether to yield material of 89.13% HPLC purity. The precipitate was washed again with 1×20 mL diethyl ether and air dried to yield 3.62 g Suc-βAla-Leu-Ala-Leu-Dox (81% physical yield, 88.2% HPLC purity). This material was stirred in 30 mL water at 0° C. and 33.98 mL (0.95 eq.) 0.1 M aq. NaHCO₃ was added and the resulting suspension stirred until all solids had dissolved. This solution was lyophilized to yield 3.77 g Suc-βAla-Leu-Ala-Leu-Dox, 99% physical yield (89.06% HPLC purity by Method B).

Example 37

Synthesis of N-cap Succinyl Form of βAla-Leu-Ala-Leu-Dnr-Therapeutic

Piperidine (0.442 mL, 4.48 mmol) was added to a solution of Fmoc form of βAla-Leu-Ala-Leu-Dnr (100 mg, 0.089 mmol) in 5 mL of dry DMF. The reaction mixture was stirred for 5 minutes at room temperature and then cooled to −20° C. using a dry ice/acetone bath. Succinic anhydride (458 mg, 4.54 mmol) was added then to the cooled reaction mixture in one portion. The reaction was stirred rapidly at −5° C. for 5 minutes then at room temperature for another 90 minutes. Anhydrous diethyl ether, 250 mL, was added to the reaction mixture and the resulting red precipitate was isolated on a medium glass frit. The filter cake was washed with two successive 50 mL portions of diethyl ether and dried under reduced pressure to yield N-cap succinyl form of βAla-Leu-Ala-Leu-Dnr-therapeutic agent (80% yield, 88% HPLC purity by method B). The LC/MS gave a molecular weight of 995 (expected molecular weight 996).

Example 38

Synthesis of N-cap Succinyl Form of Thi-Tyr-Gly-Leu-Dnr Therapeutic Agent

To a solution of Fmoc form of Thi-Tyr-Gly-Leu-Dnr (100 mg, 0.079 mmol) in 5 mL of dry DMF, piperidine (0.391 mL, 3.95 mmol) was added in one portion resulting in a color change from red to purple. The reaction mixture was stirred for 5 minutes at room temperature and then cooled to −20° C. using a dry ice/acetone bath. 407 mg (4.02 mmol) of succinic anhydride was then added to the cooled reaction mixture in one portion. The reaction was stirred rapidly at −5° C. for 5 minutes then at room temperature for another 90 minutes. Anhydrous diethyl ether, 200 mL, was added to the reaction mixture which resulted in the formation of a red precipitate. This precipitate was isolated on a medium glass frit, washed with 3×50 mL of diethyl ether and dried under reduced pressure to yield N-cap succinyl form of Thi-Tyr-Gly-Leu-Dnr Therapeutic Agent (80% yield, 81% HPLC purity by method A). The LC/MS gave a molecular weight of 1141 (expected molecular weight 1142).

Example 39

Synthesis of Sodium Salt of N-cap Glutaryl Form of βAla-Leu-Ala-Leu-Dox Therapeutic Agent Piperidine (436 µL, 4.413 mmol) was added to a solution of Fmoc form of βAla-Leu-Ala-Leu-Dox (100 mg, 0.088 mmol) in DMF (4.5 mL). After stirring for 5 minutes at room temperature, the reaction mixture was cooled to −5° C. and glutaric anhydride (624 mg, 5.472 mmol) was quickly added. The cold bath was removed as soon as the color changed and the mixture was stirred at room temperature for another 10 min. The DMF was removed by rotary evaporation and the residue dissolved in chloroform (2.5 mL). Diethyl ether (14 mL) was added and the resulting precipitate filtered. The filter cake was washed with diethyl ether, air dried and then resuspended in water (14 mL). The sodium salt was formed by addition of 0.025 M NaOH (4 mL, 0.10 mmol) dropwise to the suspension until complete dissolution of the solid. This solution was then lyophilized to give the sodium salt of Gl-βAla-Leu-Ala-Leu-Dox in 97% yield with an HPLC purity of 87% by method D.

Example 40

"Urea Method" for Preparing the Conjugate. i.e. Precursor for Enzyme Route Coupling of Methyl Succinyl-N-Cap Form of βAla-Leu-Ala-Leu and Doxorubicin Under dry nitrogen atmosphere 26.04 g (52.0 mmol) methyl succinyl-N-cap form of βAla-Leu-Ala-Leu, 23.26 g (40.2 mmol) doxorubicin hydrochloride was suspended/dissolved in 800 mL dry, urea-saturated (about 30% w/v) DMF and 14.8 19.948 mL. 114.16 mmol DIEA. This mixture was cooled to 0-3° C. over ~25 minutes. At this point 21.2 g (56.0 mmol) HATU was added as a solution in about 100 mL urea saturated DMF over 10 minutes (the volume of this solution should be kept minimal). The reaction mixture was stirred for 10 minutes at −2 to 2° C. and poured into 4000 mL ice cold brine, containing 2% v/v acetic acid over approximately five minutes with vigorous stirring. The product was filtered off on a medium porosity fritted glass filter, washed generously with water and dried under reduced pressure. 43 g physical yield: 104.47%, 93.45% pure by HPLC method B.

Example 41

Synthesis of Methyl Succinyl-N-Cap Form of βAla-Leu-Ala-Leu-Dox Therapeutic Agent In a round bottom flask (50 mL), N-cap methyl hemisuccinyl form of βAla-Leu-Ala-Leu (0.25 g, 0.5 mmol) and doxorubicin (0.29 g, 0.5 mmol) were dissolved in anhydrous DMF (20 mL). After the mixture was stirred for 5 minutes, DIEA (0.17 mL, 1.0 mmol) followed by HBTU (0.19 g, 0.5 mmol) was added into the solution. The mixture was stirred at room temperature for 4 hrs. DMF was removed by a rotary evaporator and the residue was taken up in 4.0 mL 1:1 methylenechloride:methanol. To this solution, 40 mL of ether was slowly added while stirring. A red precipitate was formed and collected by suction filtration. The solid was washed with ether (2×10 mL) and dried in a vacuum desiccator. 0.50 g of product (98%) was produced with purity of 96%.

Example 42

Removal of Free Doxorubicin from MeOSuc-β-Ala-Leu-Ala-Leu-Dox

MeOSuc-β-Ala-Leu-Ala-Leu-Dox (200 mg, 0.194 mmol), DIEA (0.068 mL, 0.388 mmol) and anhydrous DMF (10 mL) were placed in a 50 ml flask equipped with a magnetic stir bar. When MeOSuc-β-Ala-Leu-Ala-Leu-Dox had completely dissolved, isocyanate resin (390 mg, 0.582, pre-swollen in 5 mL of dichloromethane for 5 minutes) was added and the resulting solution was stirred for 2 h at room temperature with periodic HPLC monitoring. HPLC chromatograms indicated that the Dox was completed removed within 45 minutes of the resin treatment. The reaction mixture was then filtered through a frit to remove the resin. The resin was washed with 10 ml DMF and the DMF washes were combined with the filtered reaction mixture. The filtered reaction mixture washes were then concentrated to a red gum on a rotary evaporator equipped with a high vacuum pump and a 30° C. water bath. The red gummy residue was suspended in 5 ml of DMF and the solution was then slowly added into a rapidly stirred anhydrous diethylether solution. A red product was formed which was then filtered over a frit and washed with diethylether and dried under reduced pressure to give MeO-Suc-β-Ala-Leu-Ala-Leu-Dox (176 mg, yield 86%).

Example 43

Hydrolysis of the Methyl Succinyl-N-Cap Form of βAla-Leu-Ala-Leu-Dox Therapeutic Agent Via Use of Cross Linked Enzyme Methyl succinyl-N-cap form of βAla-Leu-Ala-Leu-Dox therapeutic agent (1.0 g, 0.975 mmol) and 100 mL DMF are placed in a 500 mL flask. The suspension was vigorously agitated with a magnetic stirrer. When the methyl succinyl-N-cap form of βAla-Leu-Ala-Leu-Dox therapeutic agent had completely dissolved, 400 mL deionized water was added and the resulting solution stirred at 35° C. A slurry of 1 g washed CLEC-PC (Altus Biologics) immobilized enzyme was rinsed in three aliquots of deionized water then resuspended in 10 mL 20% aqueous DMF prior to use.) suspended in 10 mL of 20% aqueous DMF was then added and the resulting suspension was stirred at 35° C. with periodic HPLC monitoring. When all of the methyl succinyl-N-cap form of βAla-Leu-Ala-Leu-Dox therapeutic agent had been consumed (about 18 hours), the reaction mixture was filtered through a 0.45 µM nylon membrane filter to remove the CLEC-PC enzyme. The CLEC-PC cake was washed with 3×10 mL methanol and the methanol washes were combined with the filtered reaction mixture. The filtered reaction mixture plus methanol washes were then concentrated to a red gum on a rotary evaporator equipped with a high vacuum pump and a 30° C. water bath. The red gum was then suspended in 50 mL deionized water at room temperature and rapidly stirred via mechanical stirrer. To this suspension a solution of 77.8 mg sodium bicarbonate (0.926 mmol, 0.95 eq.) in 100 mL deionized water was added over 2 minutes. The suspension was stirred at room temperature 20 minutes. The reaction mixture was filtered through a 0.45 µM nylon membrane filter and lyophilized. 0.936 g sodium salt of succinyl-N-cap form of βAla-Leu-Ala-Leu-Dox therapeutic agent was isolated, about 100% yield, 84% pure HPLC method B. $^1$H and $^{13}$C NMR spectra were recorded on 600 and 150 MHz spectrometers, respectively, and the electrospray MS, were consistent with the desired structure.

Example 44

Hydrolysis of the Methyl succinyl-N-Cap Form of βAla-Leu-Ala-Leu-Dox Therapeutic Agent Via Use of Soluble Enzyme 11.0 g (10.72 mmol) methyl succinyl-N-cap form of βAla-Leu-Ala-Leu-Dox therapeutic agent was suspended in 800 mL HPLC-grade water and homogenized for 60 minutes with an Ultraturrax T8 homogenizer to yield a finely divided suspension. This suspension was stirred (500 rpm) at 35° C. and adjusted to pH=6.05 with aq. 76 mM NaHCO$_3$. 1.0 g *C. Antarctica* "B" lipase (Altus Biologics) was then added and the reaction mixture stirred at 35° C. for 48 hours. During the 48 hr reaction time, pH was maintained between 5.3 and 6.2 by periodic addition of 76 mM NaHCO$_3$ and the reaction was periodically monitored by HPLC. After 48 hours, the reaction was about 98% complete by HPLC. The reaction mixture was then adjusted to pH=7 with aq. 76 mM NaHCO$_3$ and filtered through a pad of Celite 521. The clarified reaction mixture was then acidified to about pH 3 with 5 mL glacial acetic acid resulting in the formation of a gummy red precipitate. The precipitate was isolated by Celite 521 filtration, subsequent rinsing of the Celite pad with methanol, filtration of the methanol solution through a 10-20 µM fritted glass filter and rotary evaporation of the filtered solution to yield 7.31 g of gummy red product. This product was converted to the sodium salt by dissolution in 70 mL 76 mM NaHCO$_3$ (0.95 eq.) and lyophilized to yield 7.30 g, 66.1% physical yield sodium salt of succinyl-N-cap form of βAla-Leu-Ala-Leu-Dox therapeutic agent, 84.5% pure by HPLC.

The product was identical to that of example 43.

Example 45

Immobilized *Candida Antarctica* "B" Lipase Hydrolysis Methyl Succinyl-N-cap Form of βAla-Leu-Ala-Leu-Dox Therapeutic Agent 30.0 g *Candida Antarctica* "B" lipase (Altus Biologics) was dissolved in 300 mL water and dialyzed against 3×4l of 50 mM aq. NaHCO$_3$ (pH=6.4). After dialysis, the volume of the dialyzed solution was about 300 mL. 360 mL of Pharmacia NHS-Activated Sepharose 4 Fast Flow was placed in a coarse glass fritted funnel and rinsed with 5×450 mL ice-cold 1 mM aq. HCl. The rinsed NHS-Activated Sepharose was then combined with the dialyzed enzyme solution. The resulting suspension was stirred at ambient temperature (about 22° C.) for 2.0 hours. The sepharose/enzyme conjugate was then isolated on a coarse fritted glass filter and then stirred in 1000 mL 100 mM aq. TRIS (pH=7.45) for 15 minutes. This suspension was filtered and incubated with another 100 mL 100 mM aqueous TRIS buffer (pH=7.45) at 4° C., overnight. The immobilized enzyme in the morning was filtered off and after washing with water, was placed into a 2000 mL three-necked, round-bottomed flask. 43 g methyl succinyl-N-cap form of βAla-Leu-Ala-Leu-Dox was added and the solids were suspended in 800 mL deionized water. The flask was fitted with an overhead stirrer, and a pH-stat set to keep the pH of the reaction mixture between 5.9-6.2 by controlling a syringe pump. The syringe pump was charged 0.1 M NaHCO$_3$. Progress of the reaction was followed by HPLC. After 6 days the immobilized enzyme was filtered off and the liquid phase was lyophilized. The dry solids were then suspended in about 11 mL dry THF and filtered off. 42.66 g, 98.34% physical yield, 93.43% (254 nm), 94.43% (480 nm) pure by HPLC by method B.

Example 46

Synthesis of the Lactate Salt of βAla-Leu-Ala-Leu-Dox Therapeutic Agent [β-Ala-Leu-Ala-Leu-Dox Lactate]

Piperidine (26 mL, 264 mmol) was added to a solution of Fmoc form of βAla-Leu-Ala-Leu-Dox therapeutic agent (6.00 g, 5.3 mmol) in DMF (265 mL). After stirring for 5 minutes at room temperature, the reaction mixture was placed in an ice-salt bath, and precooled (4° C.) 10% lactate buffer pH 3 (600 mL) was immediately added. The aqueous solution was extracted with DCM (3×500 mL) and excess salts were removed by solid phase extraction. C18 ODS-A silica gel (120 g) was conditioned (500 mL methanol, 2×500 mL water) in a glass frit and loaded with the aqueous solution of crude product lactate salt. After washing with water (2×500 mL) and drying, the filter cake was dissolved in methanol. The methanol was evaporated and the residue was dissolved in water. The resulting solution was lyophilized to give 3.54 g of lactate salt of βAla-Leu-Ala-Leu-Dox therapeutic agent (67% yield, HPLC purity method B: 89%).

Example 47

Synthesis of Succinyl-N-Cap Form of βAla-Leu-Ala-Leu-Dox Therapeutic Agent Starting From Lactate Salt of βAla-Leu-Ala-Leu-Dox Therapeutic Agent DIEA (417 µL, 2.40 mmol) was added to a solution of Lactate salt of βAla-Leu-Ala-Leu-Dox therapeutic agent (1.200 g, 1.20 mmol) in DMF (35 mL). After stirring for 15 minutes at room temperature, succinic anhydride 97% (0.144 g, 1.44 mmol) was added. The mixture was stirred for 2 h, and DMF was removed by rotary evaporation. The residue was dissolved in a mixture of $CHCl_3/CH_3OH$ 4/1 (6 mL), and 200 mL of a mixture of 1:1 $Et_2O$:hexane were added. After the mixture was stirred for 30 minutes, the precipitate was filtered on quantitative paper (Whatman 42), washed (1:1 $Et_2O$:hexane) and air-dried. The filter cake was suspended in water (150 mL), and 1M NaOH (±1.2 eq., 1.5 mL) was added dropwise until complete dissolution (pH=7.2). The solution was lyophilized to give 1.218 g of succinyl-N-cap form of βAla-Leu-Ala-Leu-Dox therapeutic agent (97% yield; HPLC purity method B: 80.2%).

Example 48

Synthesis of Succinyl-N-Cap Form of βAla-Leu-Ala-Leu-Dox Therapeutic Agent Starting with Fmoc Form of βAla-Leu-Ala-Leu-Dox Therapeutic Agent Piperidine (2180 µL, 22.06 mmol) was added to a solution of Fmoc form of βAla-Leu-Ala-Leu-Dox therapeutic agent (0.50 g, 0.44 mmol) in DMF (21.5 mL). After stirring for 5 minutes at room temperature, the reaction mixture was quickly cooled to −5° C. and succinic anhydride (2.25 g, 22.51 mmol) was added immediately. The cold bath was removed as soon as the color changed and the mixture was stirred at room temperature for 10 minutes. The DMF was removed by rotary evaporation and the residue was dissolved in chloroform (12.5 mL). Diethylether (360 mL) was quickly added. A precipitate immediately appeared. The precipitate was filtered on Whatman 42 paper and washed with $Et_2O$. The solid was suspended in water (120 mL; pH=4.1) and 0.025M NaOH (20 mL, 0.53 mmol) was added dropwise until complete dissolution (pH=7.4). This solution was then lyophilized to give succinyl-N-cap form of βAla-Leu-Ala-Leu-Dox therapeutic agent in 89% yield and 91% HPLC purity by Method D.

Example 49

Large Scale Synthesis of Methyl Succinyl-N-Cap form of βAla-Leu-Ala-Leu-Dox Therapeutic Agent 69.6 g Doxorubicin.HCl (120 mmol) and 100 g MeOSuc-bAla-Leu-Ala-Leu (199 mmol) were dissolved in anhydrous DMF (10 L) under nitrogen. 76 mL DIEA (434 mmol) was added to the reaction mixture and the reaction mixture was stirred for 10 minutes at room temperature under nitrogen. The reaction mixture was then cooled to 0° C. over 10 minutes. In a separate flask a solution of 864 g HATU (220 mmol) in DMF (500 mL) was prepared. The HATU solution was added slowly over 20 minutes to the reaction mixture while the reaction mixture was maintained at 0° C. The reaction mixture was stirred at 0° C. for 30 minutes.

A solution of NaCl (7.5 Kg, at least 30% w/v) in water (25 L) was prepared and cooled to 0° C. The reaction mixture was then slowly added to the cooled brine solution with vigorous stirring over 120 minutes. The color of the solution remained red, a blue solution would have indicated that the pH needed adjustment immediately to between 5.8-6.0 by adding acetic acid. The temperature was maintained at =approximately 5° C. The red precipitate was filtered off on a medium porosity fritted glass filter, washed with water and dried under vacuum pressure over $P_2O_5$ to yield 115 g of MeOSuc-βAla-Leu-Ala-Leu-Dox.

Example 50

Treatment of MeOSuc-βAla-Leu-Ala-Leu-Dox with Ps-Isocyanate Beads to Remove Traces of Doxorubicin 146.4 g PS-isocyanate beads (240 mmol; supplied by Argonaut Lab, San Carlos, Calif.) were dissolved in 1.5 L of anhydrous DMF and allowed to swell for 5-10 minutes at room temperature. The swelled beads were filtered through a glass-fritted funnel and washed with additional 500 mL of anhydrous DMF. 115 g MeOSuc-βAla-Leu-Ala-Leu-Dox (112 mmol) was dissolved in 1000 mL of anhydrous DMF and 2.1 mL DIEA (12 mmol) was added followed by the swelled PS-isocyanate beads. The reaction mixture was stirred at room temperature and was monitored using HPLC till the amount of doxorubicin peak was less than 0.1%. It takes anywhere from 2-12 h depending upon the size of the batch. Analytical HPLC analyses were performed using Water 2690 Column: Waters Symmetry Shield $C_8$ 3.5 µM 4.6×150 mm (cat #WAT094269), solvent: A-80% aqueous 20 mM ammonium formate (pH=4.5) 20% acetonitrile, solvent: B-20% aqueous 20 mM ammonium formate (pH=4.5) 80% acetonitrile. Column temperature: controlled room temperature, sample Temperature 4° C., Run time: 37.5 minutes, detector: 254 nm, Flow rate: 1.0 mL/min, Injection amount 10 µg (0.5 mg/mL×0.02 mL), Mobile Phase A and B. Gradient: 37.5 minute linear gradient from 100% mobile phase A to 100% mobile phase B with a 7.5 minute equilibration delay.

At six hours the amount of doxorubicin peak was less than 0.1%, the reaction mixture was filtered through a coarse sintered glass funnel to remove the beads. A brine solution (at least 30% w/v) of 1.1 kg NaCl in 3.5 L water was prepared and cooled to 0° C. The filtered reaction mixture was then slowly added to the cooled brine solution with vigorous stirring over 45 minutes. The color of the solution remained red, a blue solution would have indicated that the pH needed adjustment immediately to between 5.8-6.0 by adding acetic acid. The red precipitate was filtered through a medium sintered glass funnel, washed with water and dried under vacuum pressure over $P_2O_5$ to yield MeOSuc-βAla-Leu-Ala-Leu-Dox free of any residual doxorubicin.

MeOSuc-βAla-Leu-Ala-Leu-Dox was dissolved in 1 L MeOH and the methanol solution was then slowly added to 14 L of cooled ethyl ether with vigorous stirring over 60 minutes. The red precipitate was filtered through a medium sintered glass funnel, washed with ether (1 L) and dried under vacuum pressure to yield 110 g MeOSuc-βAla-Leu-Ala-Leu-Dox. The purity was determined to be 96.5% by HPLC, as described in Example 44. MS m/z calcd. for $C_{50}H_{67}N_5O_{18}$ 1025. Found 1048 ($M^+$+Na).

Example 51

Enzymatic Hydrolysis of MeOSuc-βAla-Leu-Ala-Leu-Dox to Yield Suc-βAla-Leu-Ala-Leu-Dox The CLEC-CAB (*Candida Antartica* "B" Lipase) enzyme was purchased (from Altus Biologics., Boston, Mass.) in solution form, where the concentration of the enzyme is defined by the weight of dry enzyme per milliliter of solution. The crude enzyme suspension was shaken for few minutes to obtain a homogenous solution. 504 mL (328 mmol) of this homogenous solution was aliquoted into a flask. 2.5 L of deionized water was added and the slurry was stirred for 10 minutes using a magnetic stirrer. The enzyme solution was filtered using a coarse glass flitted funnel, without taking the enzyme to dryness. The enzyme was transferred back into a flask. The enzyme is suspended in water and filtered three more times.

The enzyme cake was resuspended into 550 mL of deionized water and transferred into a RB flask. To this suspension, 109 g MeOSuc-βAla-Leu-Ala-Leu-Dox (106 mmol) was added and the reaction mixture was stirred at room temperature (25° C.). The pH of the reaction mixture was maintained between 5.8 and 6.1 by a pH-stat equipped with a syringe pump charged with 1 N $NaHCO_3$ solution. Progress of the reaction was followed with periodic HPLC monitoring, as described in Example 44. After 24 hours, the reaction seems to be 94% complete, as determined by HPLC.

To speed up the reaction, additional CLEC enzyme was required after 24 hours. 168 mL of the CLEC enzyme (homogenous solution) was washed in a column format as described above. The enzyme cake was resuspended into 1.1 L of deionized water and added to the reaction mixture. The reaction mixture was stirred at room temperature with periodic HPLC monitoring and the pH was maintained between 5.8 and 6.1. After 60 hours, the reaction was 99.9% complete, as monitored by HPLC.

The CLEC enzyme was removed from the reaction mixture by filtration through a 0.2 μM filter and rinsed with 500 mL of deionized water. The filtrate was then lyophilized to yield 95.2 g Suc-βAla-Leu-Ala-Leu-Dox.Na, 87% physical yield, MS m/z calcd. for $C_{49}H_{65}N_5O_{18}$ 1011. Found 1034 ($M^+ +Na$).

The prodrug compound, Suc-βAla-Leu-Ala-Leu-Dox, was fully characterized by mass spectrum analysis, FTIR, NMR.

Mass spectrum analysis of Suc-βAla-Leu-Ala-Leu-Dox clearly shows the presence of the molecular ion peak (m/z) at 1034 ($M^+ +Na$) which matches with the calculated m/z for Suc-βAla-Leu-Ala-Leu-Dox ($C_{49}H_{65}N_5O_{18}Na$) at 1033.

The sample of Suc-βAla-Leu-Ala-Leu-Dox was also analyzed by FTIR. The spectrum matched that of a reference standard of the above material. Assignments for major absorptions are as follow:

| | |
|---|---|
| Hydroxyl | 3379 $cm^{-1}$ |
| C—H | 3000-2700 |
| Carbonyls | 1650-1725 |

Figure 17:
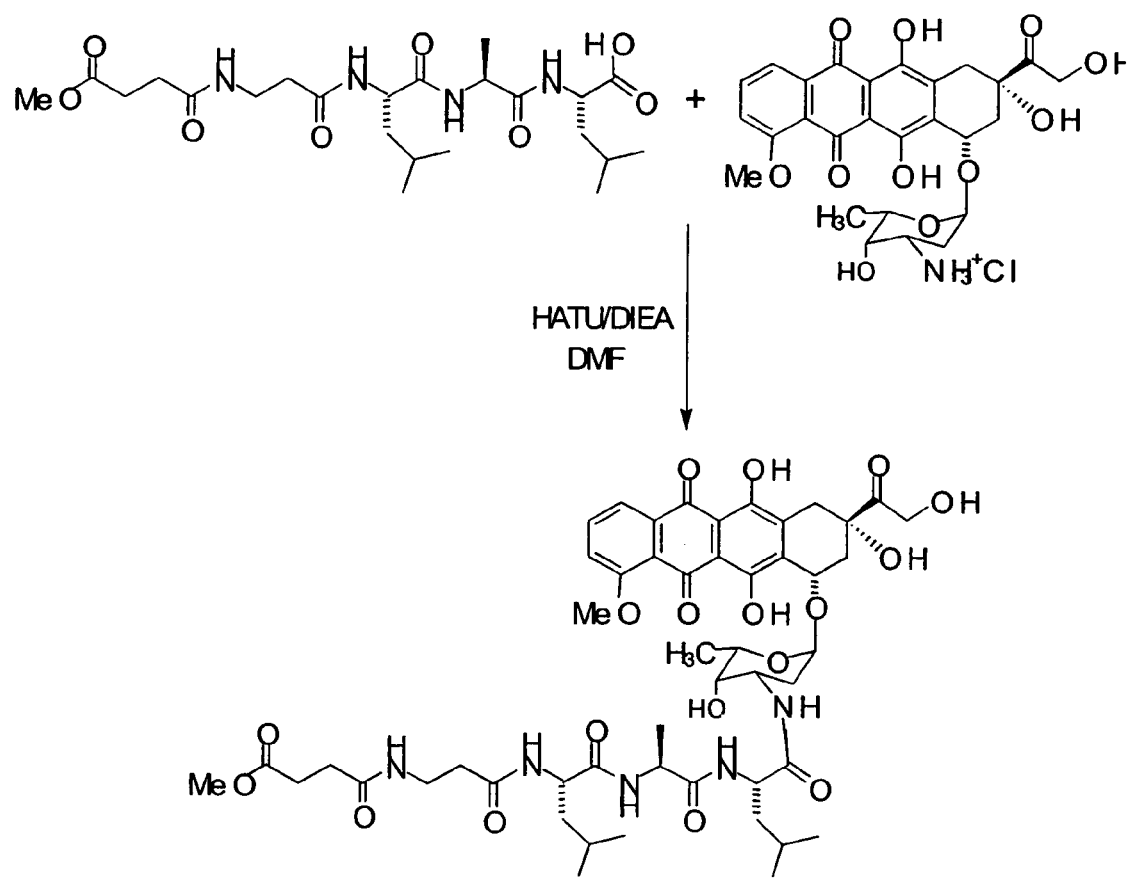
FIG. 17 illustrates the NMR assignment for MeOSuc-βAla-Leu-Ala-Leu-Dox, a typical compound of the invention.

Finally the sample was analyzed by NMR. The chemical shifts and assignments are listed in Table 13 and illustrated in FIG. 17. There are three carbons in the ketone region, at 215.2, 187.7, 187.4 ppm, consistent with the structure of Suc-βAla-Leu-Ala-Leu-Dox. The latter two have similar chemical shifts, so are assigned to (2) and (3), at 187.7 and 187.4 ppm. The remaining ketone is therefore (1). Further evidence from these assignments arise from the HMQC and HMBC spectra; none of these three show any HMQC peaks, so are nonprotonated, and only (1) has a long-range C—H coupling (HMBC), to the proton at 4.77 ppm, which is a two-proton singlet, which is therefore (4). From the HMQC spectrum, the carbon at 65.7 ppm is linked to these protons.

The $^1H$ NMR signal at 3.96 ppm has the chemical shift and the area of a methoxy group; these protons are coupled to the carbon at 57.2 ppm, and are assigned to the only methoxy in the structure (5). The $^{13}C$ chemical shift is also consistent with a methoxy. The long-range C—H coupling of the protons is to the carbon at 162.3 ppm, which must be (6).

The HMQC spectrum shows that there are three protonated aromatic carbons at 120.5, 120.3 and 137.2 ppm; the aromatic protons did not show any long-range C—H coupling, nor any coupling between adjacent protons. The aromatic protons signals are very broad, indicating a short $T_2$ relaxation time, which explains the lack of any observed coupling. Given this lack of coupling, it is not possible to assign these three sites uniquely, and are collectively assigned to (7), (8) and (9).

The two non-protonated aromatic carbons at 157.2 and 156.1 ppm have chemical shifts consistent with (10) and (11), i.e., aromatic carbons attached to oxygen. No long-range coupling is observed.

The $^{13}C$ NMR signals at 112.3 and 112.0 ppm are consistent with aromatic carbons ortho to oxygen substitution, and are assigned to (12) and (13). The $^{13}C$ NMR signal at 121.3 also shows this effect, so is assigned to (14). The remaining three non-protonated aromatic carbons are assigned to the last three carbons in the region, (15), (16) and (17).

The lack of any long-range C—H coupling to any of the aromatic carbons is unexpected, and indicates that the coupling is very small or non-existent, either due to short $T_2$ relaxation times or a planar configuration.

There are six carbonyl carbons at 181 to 174 ppm; of these, the one at 180.6 ppm is the only one with a chemical shift consistent with a sodium salt, so is assigned to (18). This peak shows long-range C—H coupling to the protons at 2.4 ppm, which are unresolved. The remaining five carbonyl carbons are all within a one ppm chemical shift range, and are not possible (19), (20), (21), (22), (23).

The carbon at 102.3 ppm has a chemical shift consistent with a carbon bound to two separate oxygen, so must be (24). This has long-range C—H coupling to the proton at 1.74 ppm, which is assigned to (25). This proton is coupled to the carbon at 30.6 ppm. Of the carbons in the C—O region (80 to 60 ppm), only one is protonated, at 77.4 ppm, so must be (26). This has no long-range C—H coupling, to either the proton or the carbon.

There are three carbons not yet assigned in the 80 to 60 ppm region, all methines attached to oxygen. They all have similar chemical shifts (71.2, 69.9 and 68.8 ppm), but it seems clear that the carbon at 68.8 ppm shows long-range coupling to the methyl to (28). The carbon at 69.9 also shows long-range coupling to the methyl at (28), so must be adjacent to (27), and is assigned to (29). The remaining methine is therefore (30).

The proton at 3.6 ppm (29) shows long-range C—H coupling to only one carbon, at 47.3 ppm. The only adjacent unassigned carbon must be (31). The protons of (31) overlap other protons and long-range correlations are not possible.

The remaining four methyls are in the isopropyl region, and one is at 1.25/1.34 ppm, and must correspond to the last remaining methyl, (32). The protons of this methyl show long-range coupling to only one carbon, at 51.3 ppm, which must be (33). The protons of (33) overlap severely with other protons and can not be used for any long-range correlations.

The remaining four methyls must all arise from the isopropyl methyls, collectively labeled (34). The protons of (34) show long-range coupling between the paired methyls, and to the carbons at 25.9/25.8 and 41.6/41.7 ppm; the methines are assigned (35)/(36) and the methylenes (37)/(38). All of these protons overlap at 1.5 to 1.8 ppm, but show long-range coupling to the methines at 54.7/53.5 ppm, which must be the ones adjacent to the amides, and are assigned (39)/(40).

The remaining five carbons, all methylenes, show long-range coupling to carbonyls, so must be adjacent to such, and are assigned (41), (42) and (43); the $^1$H NMR chemical shifts all overlap at 2.4 ppm, and correspondence to carbons at 37.2, 34.4 and 33.8 ppm. Since the carbon at 37.2 is the most difference, it is assigned to the sodium salt carbonyl (41), and the other two to the amide carbonyls (42), (43). The remaining two methylenes are too similar for specific assignment (44), (45).

There is one site unassigned. There are thirty protons in the 5.5 to 1.5 ppm region, consistent with the structure, including this assigned site. Therefore it is likely that the carbon signal is hidden under the solvent signal at about 50 ppm, which would be consistent for methylene adjacent to a nitrogen.

TABLE 13

| $^{13}$C and $^1$H Chemical Shifts | HMOC to $^1$H | Assignment |
|---|---|---|
| 215.2 | | 1 |
| 187.7 | | 2/3 |
| 187.4 | | 2/3 |
| 180.6 | | 18 |
| 176.1 | | 19-23 |
| 175.8 | | 19-23 |
| 175.4 | | 19-23 |
| 175.2 | | 19-23 |
| 174.1 | | 19-23 |
| 162.3 | | 6 |
| 157.2 | | 10/11 |
| 156.1 | | 10/11 |
| 137.2 | 7.68 | 7/8/9 |
| 136.1 | | 15/16/17 |
| 135.6 | | 15/16/17 |
| 135 | | 15/16/17 |
| 121.3 | | 14 |
| 120.5 | 7.68 | 7/8/9 |
| 120.3 | 7.42 | 7/8/9 |
| 112.3 | | 12/13 |
| 112 | | 12/13 |
| 102.3 | 5.34 | 24 |
| 77.4 | | 26 |
| 71.2 | 4.97 | 30 |
| 69.9 | 3.6 | 29 |
| 68.8 | 4.24 | 27 |
| 65.7 | 4.77 | 4 |
| 57.2 | 3.96 | 5 |
| 54.7 | 4.24 | 39/40 |
| 53.5 | 4.32 | 39/40 |
| 51.3 | 4.24 | 33 |
| 47.3 | 4.15/4.12 | 31 |
| 41.6 | 1.6 | 35/36 |
| 41.5 | 1.6 | 35/36 |
| 37.2 | 2.4 | 41 |
| 37 | 3.45 | 44/45 |
| 34.4 | 2.4 | 42/43 |
| 34 | 3-2.7 | 44/45 |
| 33.8 | 2.4 | 42/43 |
| 30.6 | 1.75 | 25 |
| 25.9 | 1.6 | 37/38 |
| 25.8 | 1.6 | 37/38 |
| 23.5 | 0.9 | 34 |
| 23.3 | 0.9 | 34 |
| 22.1 | 0.9 | 34 |
| 21.7 | 0.9 | 34 |
| 17.4 | 1.35/1.34 | 32 |
| 17.5 | 1.29/1.27 | 28 |

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

The invention claimed is:

1. A method for treating colorectal cancer, breast cancer and cervical cancer in a patient in need thereof, the method comprising administering a therapeutically effective amount of a compound comprising:

(1) a therapeutic agent capable of entering a target cell, wherein said therapeutic agent is an alkylating agent, antiproliferative agent, tubulin binding agent, vinca alkaloid, enediyne, podophyllotoxin, podophyllotoxin derivative, a member of the pteridine family of drugs, taxane, a dolastatin, topoisomerase inhibitor, or a platinum complex chemotherapeutic agent, (2) an oligopeptide of the formula $(AA)_n\text{-}AA^4\text{-}AA^3\text{-}AA^2\text{-}AA^1$, wherein: each AA independently represents an amino acid, n is an integer from 0 to 16, $AA^4$ represents β-alanine, thiazolidine-4-carboxylic acid, 2-thienylalanine, 2-naphthylalanine, D-alanine, D-leucine, D-methionine, D-phenylalanine, 3-amino-3-phenylpropionic acid, γ-aminobutyric acid, 3-amino-4,4-diphenylbutyric acid, tetrahydroisoquinoline-3-carboxylic acid, 4-aminomethylbenzoic acid, and aminoisobutyric acid, $AA^3$ represents any amino acid, $AA^2$ represents any amino acid, and $AA^1$ represents any amino acid, (3) a negatively charged stabilizing group, and (4) optionally, a linker group not cleavable by TOP, wherein the oligopeptide is directly linked to the stabilizing group at the amino terminus of the oligopeptide and the oligopeptide is directly linked to the therapeutic agent or indirectly linked through the linker group to the therapeutic agent at a second attachment site of the oligopeptide, wherein the stabilizing group reduces acute toxicity of the compound when administered in vivo, and wherein the compound is cleavable by TOP.

2. The method of claim 1 wherein the oligopeptide is selected from the group consisting of: D-AlaThiβAlaβAla-LeuAlaLeu (SEQ ID NO: 1), ThiβAlaβAlaLeuAlaLeu (SEQ ID NO: 2), βAlaβAlaLeuAlaLeu (SEQ ID NO: 3), βAlaLeu-TyrLeu (SEQ ID NO: 17), βAlaLeuThiLeu (SEQ ID NO: 18), βAlaLeuThrLeu (SEQ ID NO: 21), βAlaLeuSerLeu (SEQ ID NO: 22), βAlaLeuPyrLeu (SEQ ID NO: 23), βAla-LeuLeuLeu (SEQ ID NO: 24), βAlaLeuGlyLeu (SEQ ID NO: 28), βAlaLeuPheLeu (SEQ ID NO: 31), βAla-LeuAibLeu (SEQ ID NO: 32), and βAlaLeuAlaLeu (SEQ ID NO: 38).

3. The method of claim 1 wherein $AA^1$ of the oligopeptide is selected from the group consisting of Leucine, Phenylalanine, Isoleucine, Alanine, Glycine, Tyrosine, 2-Naphthylalanine, Serine, p-Cl-phenylalanine, p-Nitrophenylalanine, 1-Naphthylalanine, Threonine, Homoserine, Cyclohexylalanine, Thienylalanine, Homophenylalanine, Norleucine, and β-Alanine.

4. The method of claim 1 wherein $AA^2$ of the oligopeptide is selected from the group consisting of Alanine, Leucine, Tyrosine, Glycine, Serine, 3-Pyridylalanine, 2-Thienylalanine, Norleucine, Homoserine, Homophenylalanine, p-Cl-phenylalanine, p-Nitrophenylalanine, Aminoisobutyric Acid, Threonine, and Phenylalanine.

5. The method of claim 1 wherein $AA^3$ of the oligopeptide is selected from the group consisting of Leucine, Tyrosine, Phenylalanine, p-Cl-Phenylalanine, p-Nitrophenylalanine, Valine, Norleucine, Norvaline, Phenylglycine, Tryptophan, Tetrahydroisoquinoline-3-carboxylic acid, 3-Pyridylalanine, Alanine, Glycine, Thienylalanine, Methionine, Valine, and Proline.

6. The method of claim 1 wherein the stabilizing group is a dicarboxylic or higher order carboxylic acid.

7. The method of claim 1 wherein the stabilizing group is selected from the group consisting of: succinic acid, adipic acid, glutaric acid, phthalic acid, diglycolic acid, fumaric acid, naphthalene dicarboxylic acid, 1,8-naphthyl dicarboxylic acid, aconitic acid, carboxycinnamic acid, triazole dicarboxylic acid, butane disulfonic acid, and maleic acid.

8. The method of claim 1 wherein the stabilizing group is a non-genetically encoded amino acid having four or more carbons.

9. The method of claim 1 wherein the stabilizing group is one of aspartic acid linked to the oligopeptide at the β-carboxy group of the aspartic acid or glutamic acid linked to the oligopeptide at the γ-carboxy group of the glutamic acid.

10. The method of claim 1 wherein the therapeutic agent is selected from the group consisting of Doxorubicin, Daunorubicin, Vinblastine, Vincristine, Calicheamicin, Etoposide, Etoposide phosphate, CC-1065, Duocarmycin, KW-2189, Methotrexate, Methopterin, Aminopterin, Dichloromethotrexate, Docetaxel, Paclitaxel, Epithiolone, Combretastatin, Combretastatin A4 Phosphate, Dolastatin 10, Dolastatin 11, Dolostatin 15, Topotecan, Camptothecin, Mitomycin C, Porfiromycin, 5-Fluorouracil, 6-Mercaptopurine, Fludarabine, Tamoxifen, Cytosine arabinoside, Adenosine arabinoside, Colchicine, Cisplatin, Carboplatin, Mitomycin C, Bleomycin, Melphalan, Chloroquine, Cyclosporin A, and a derivative of any of the foregoing.

11. The method of claim 1 wherein the oligopeptide is directly linked to the therapeutic agent.

12. The method of claim 1 wherein the oligopeptide sequence is indirectly linked to the therapeutic agent at the second attachment site of the oligopeptide via a linker group, the linker group selected from the group consisting of amino caproic acid, a hydrazide group, an ester group, an ether group, and a sulphydryl group.

13. A method of claim 1 wherein the compound is selected from the group consisting of Suc-βAla-Leu-Ala-Leu-Dox, (Suc-(SEQ ID NO: 38), Suc-βAla-Leu-Ala-Leu-Dnr (Suc-(SEQ ID NO: 38)-Dnr) and Glutaryl-βAla-Leu-Ala-Leu-Dox (Glutaryl-(SEQ ID NO: 38)-Dox).

14. The method of claim 1 wherein n is an integer from 0 to 8.

15. The method of claim 1 wherein n is 0.

16. The method of claim 1 wherein the oligopeptide is βAla-Leu-Ala-Leu (SEQ ID NO: 38).

17. The method of claim 1 wherein the compound is Suc-βAla-Leu-Ala-Leu-Dox (Suc-(SEQ ID NO: 38)-Dox).

* * * * *

SEQUENCE LISTING

```
<160> NUMBER OF SEQ ID NOS: 105

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Alanine
<220> FEATURE:
<221> NAME/KEY: MOD_RES
<222> LOCATION: (2)
<223> OTHER INFORMATION: 2-Thienylalanine
<220> FEATURE:
<221> NAME/KEY: MOD_RES
<222> LOCATION: (3)..(4)
<223> OTHER INFORMATION: Beta-Alanine

<400> SEQUENCE: 1
```

```
Xaa Xaa Xaa Xaa Leu Ala Leu
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 2-Thienylalanine
<220> FEATURE:
<221> NAME/KEY: MOD_RES
<222> LOCATION: (2)..(3)
<223> OTHER INFORMATION: Beta-Alanine

<400> SEQUENCE: 2

Xaa Xaa Xaa Leu Ala Leu
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Beta-Alanine

<400> SEQUENCE: 3

Xaa Xaa Leu Ala Leu
1               5

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 4

Xaa Ala Ala Ile
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 5

Xaa Ala Ala Leu
1
```

```
<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 6

Xaa Phe Tyr Leu
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 7

Xaa Phe Thr Phe
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 8

Xaa Phe Gly Ile
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 9

Xaa Phe Gly Leu
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)
<223> OTHER INFORMATION: Beta-Alanine

<400> SEQUENCE: 10

Xaa Phe Phe Phe
 1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 11

Xaa Phe Phe Ile
 1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 12

Xaa Phe Phe Leu
 1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 13

Xaa Phe Ala Ile
 1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 14

Xaa Phe Ala Leu
 1
```

```
<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 2-Thienylalanine

<400> SEQUENCE: 15

Xaa Gly Ala Leu
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 2-Naphthylalanine

<400> SEQUENCE: 16

Xaa Gly Ala Leu
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 17

Xaa Leu Tyr Leu
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (3)
<223> OTHER INFORMATION: 2-Thienylalanine

<400> SEQUENCE: 18

Xaa Leu Xaa Leu
1

<210> SEQ ID NO 19
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 19

Xaa Leu Thr Phe
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 20

Xaa Leu Thr Ile
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 21

Xaa Leu Thr Leu
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 22

Xaa Leu Ser Leu
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
```

```
<223> OTHER INFORMATION: Beta-Alanine
<220> FEATURE:
<221> NAME/KEY: MOD_RES
<222> LOCATION: (3)
<223> OTHER INFORMATION: 3-Pyridylalanine

<400> SEQUENCE: 23

Xaa Leu Xaa Leu
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 24

Xaa Leu Leu Leu
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 25

Xaa Leu Gly Phe
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 26

Xaa Leu Gly Ile
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 2-Thienylalanine

<400> SEQUENCE: 27
```

```
Xaa Leu Gly Leu
1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 28

Xaa Leu Gly Leu
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aminoisobutyric acid

<400> SEQUENCE: 29

Xaa Leu Gly Leu
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 30

Xaa Leu Phe Ile
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 31

Xaa Leu Phe Leu
1

<210> SEQ ID NO 32
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (3)
<223> OTHER INFORMATION: Aminoisobutyric acid

<400> SEQUENCE: 32

Xaa Leu Xaa Leu
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 33

Xaa Leu Ala Ala
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (4)
<223> OTHER INFORMATION: Beta-Alanine

<400> SEQUENCE: 34

Xaa Leu Ala Xaa
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 35

Xaa Leu Ala Phe
1

<210> SEQ ID NO 36
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 36

Xaa Leu Ala Gly
1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 37

Xaa Leu Ala Ile
1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 38

Xaa Leu Ala Leu
1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Tetrahydroisoquinoline-3-carboxylic acid

<400> SEQUENCE: 39

Xaa Leu Ala Leu
1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Thiazolidine-4-carboxylic acid
```

-continued

```
<400> SEQUENCE: 40

Xaa Leu Ala Leu
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 2-Thienylalanine

<400> SEQUENCE: 41

Xaa Leu Ala Leu
1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 2-Naphthylalanine

<400> SEQUENCE: 42

Xaa Leu Ala Leu
1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 3-Amino-4,4-diphenylbutyric acid

<400> SEQUENCE: 43

Xaa Leu Ala Leu
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Leucine

<400> SEQUENCE: 44

Xaa Leu Ala Leu
1

<210> SEQ ID NO 45
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Alanine

<400> SEQUENCE: 45

Xaa Leu Ala Leu
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Methionine

<400> SEQUENCE: 46

Xaa Leu Ala Leu
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 3-Amino-3-phenylpropionic acid

<400> SEQUENCE: 47

Xaa Leu Ala Leu
1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 4-(Aminomethyl)benzoic acid

<400> SEQUENCE: 48

Xaa Leu Ala Leu
1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
```

-continued

```
<223> OTHER INFORMATION: Beta-Alanine
<220> FEATURE:
<221> NAME/KEY: MOD_RES
<222> LOCATION: (4)
<223> OTHER INFORMATION: 2-Naphthylalanine

<400> SEQUENCE: 49

Xaa Leu Ala Xaa
1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 50

Xaa Leu Ala Ser
1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 51

Xaa Leu Ala Tyr
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 52

Xaa Met Tyr Phe
1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 53
```

```
Xaa Met Tyr Leu
1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 54

Xaa Met Gly Ile
1

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 2-Thienylalanine

<400> SEQUENCE: 55

Xaa Met Gly Leu
1

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 56

Xaa Met Phe Phe
1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 57

Xaa Met Phe Ile
1

<210> SEQ ID NO 58
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Tetrahydroisoquinoline-3-carboxylic acid

<400> SEQUENCE: 58

Xaa Met Ala Leu
 1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 2-Naphthylalanine

<400> SEQUENCE: 59

Xaa Met Ala Leu
 1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 3-Amino-4,4-diphenylbutyric acid

<400> SEQUENCE: 60

Xaa Met Ala Leu
 1

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 61

Xaa Met Ala Leu
 1

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 3-Amino-3-phenylpropionic acid
```

-continued

```
<400> SEQUENCE: 62

Xaa Met Ala Leu
1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Norleucine

<400> SEQUENCE: 63

Xaa Xaa Tyr Ile
1

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Norleucine

<400> SEQUENCE: 64

Xaa Xaa Tyr Leu
1

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Norleucine

<400> SEQUENCE: 65

Xaa Xaa Thr Ile
1

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Norleucine

<400> SEQUENCE: 66

Xaa Xaa Thr Leu
1

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Norleucine

<400> SEQUENCE: 67

Xaa Xaa Gly Phe
1

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Norleucine

<400> SEQUENCE: 68

Xaa Xaa Gly Ile
1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Norleucine

<400> SEQUENCE: 69

Xaa Xaa Gly Leu
1
```

```
<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Norleucine

<400> SEQUENCE: 70

Xaa Xaa Phe Ile
1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Norleucine

<400> SEQUENCE: 71

Xaa Xaa Ala Ile
1

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Norleucine

<400> SEQUENCE: 72

Xaa Xaa Ala Leu
1

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
```

```
<223> OTHER INFORMATION: Norleucine

<400> SEQUENCE: 73

Xaa Xaa Ala Phe
1

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Norvaline

<400> SEQUENCE: 74

Xaa Xaa Ala Leu
1

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 75

Xaa Phe Tyr Ile
1

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 2-Thienylalanine

<400> SEQUENCE: 76

Xaa Pro Gly Leu
1

<210> SEQ ID NO 77
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 2-Thienylalanine

<400> SEQUENCE: 77
```

```
Xaa Pro Ala Leu
1

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 2-Naphthylalanine

<400> SEQUENCE: 78

Xaa Pro Ala Leu
1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 79

Xaa Pro Ala Leu
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Phe(Cl)

<400> SEQUENCE: 80

Xaa Xaa Ala Leu
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Phe(NO2)

<400> SEQUENCE: 81
```

Xaa Xaa Ala Ile
1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Phe(NO2)

<400> SEQUENCE: 82

Xaa Xaa Ala Leu
1

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Phenylglycine

<400> SEQUENCE: 83

Xaa Xaa Ala Leu
1

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: 3-Pyridylalanine

<400> SEQUENCE: 84

Xaa Xaa Ala Leu
1

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)

```
<223> OTHER INFORMATION: Tetrahydroisoquinoline-3-carboxylic acid

<400> SEQUENCE: 85

Xaa Thr Gly Leu
1

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: 2-Thienylalanine

<400> SEQUENCE: 86

Xaa Xaa Gly Ile
1

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: 2-Thienylalanine

<400> SEQUENCE: 87

Xaa Xaa Ala Leu
1

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Tetrahydroisoquinoline-3-carboxylic acid

<400> SEQUENCE: 88

Xaa Xaa Ala Ile
1

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)
<223> OTHER INFORMATION: Beta-Alanine
<220> FEATURE:
<221> NAME/KEY: MOD_RES
<222> LOCATION: (2)
<223> OTHER INFORMATION: Tetrahydroisoquinoline

<400> SEQUENCE: 89

Xaa Xaa Ala Leu
1

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 90

Xaa Val Ala Leu
1

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 91

Xaa Trp Ala Leu
1

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 92

Xaa Tyr Tyr Phe
1

<210> SEQ ID NO 93
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
```

<223> OTHER INFORMATION: Beta-Alanine

<400> SEQUENCE: 93

Xaa Tyr Tyr Ile
1

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 94

Xaa Tyr Tyr Leu
1

<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 95

Xaa Tyr Thr Leu
1

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 96

Xaa Tyr Phe Leu
1

<210> SEQ ID NO 97
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 97

Xaa Tyr Gly Ile
1

```
<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 2-Thienylalanine

<400> SEQUENCE: 98

Xaa Tyr Gly Leu
1

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 99

Xaa Tyr Gly Leu
1

<210> SEQ ID NO 100
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 100

Xaa Tyr Phe Ile
1

<210> SEQ ID NO 101
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 101

Xaa Tyr Ala Ile
1

<210> SEQ ID NO 102
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)
<223> OTHER INFORMATION: 2-Thienylalanine

<400> SEQUENCE: 102

Xaa Tyr Ala Leu
1

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Beta-Alanine

<400> SEQUENCE: 103

Xaa Tyr Ala Leu
1

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ile or Leu

<400> SEQUENCE: 104

Ala Xaa Ala Asp Val Glu Val Thr Tyr Thr Val Gln Arg
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Trp Asp Leu Ser Ala Gln Gln Ile Glu Glu Arg
1               5                   10
```